(12) United States Patent
Ivanova et al.

(10) Patent No.: US 7,371,542 B2
(45) Date of Patent: May 13, 2008

(54) GENE EXPRESSION SYSTEM

(75) Inventors: Lidia Ivanova, Schlieren (CH);
Philippe Saudan, Pfungen (CH)

(73) Assignee: Cytos Biotechnology AG,
Zurich-Schlieren (CH)

(*) Notice: Subject to any disclaimer, the term of this patent is extended or adjusted under 35 U.S.C. 154(b) by 391 days.

(21) Appl. No.: 10/888,961

(22) Filed: Jul. 12, 2004

(65) Prior Publication Data

US 2005/0064467 A1 Mar. 24, 2005

Related U.S. Application Data

(60) Provisional application No. 60/524,852, filed on Nov. 26, 2003, provisional application No. 60/486,238, filed on Jul. 11, 2003.

(30) Foreign Application Priority Data

Jul. 9, 2004 (WO) ............... PCT/EP2004/007556

(51) Int. Cl.
*C12P 1/02* (2006.01)
(52) U.S. Cl. ............... 435/69.1; 435/320.1; 435/235.1; 435/91.41; 435/325
(58) Field of Classification Search ............ None
See application file for complete search history.

(56) References Cited

U.S. PATENT DOCUMENTS

| | | |
|---|---|---|
| 4,686,186 A | 8/1987 | Sugden |
| 5,580,859 A | 12/1996 | Felgner et al. |
| 5,705,163 A | 1/1998 | Pastan et al. |
| 6,194,212 B1 | 2/2001 | Agarwal et al. |
| 6,410,314 B1 | 6/2002 | Baiker et al. |

FOREIGN PATENT DOCUMENTS

| | | |
|---|---|---|
| EP | 0 716 148 A2 | 9/1994 |
| EP | 0 716 148 A3 | 9/1994 |
| WO | WO 95/27020 A1 | 3/1995 |
| WO | WO 96/17072 A2 | 6/1996 |
| WO | WO 97/46687 | 12/1997 |
| WO | WO 98/13511 A1 | 4/1998 |
| WO | WO 99/50432 A1 | 3/1999 |
| WO | WO 2004/053137 A2 | 6/2004 |
| WO | WO 2004/053137 A3 | 6/2004 |

OTHER PUBLICATIONS

Agapov, E.V., et al., "Noncytopathic Sindbis virus RNA vectors for heterologous gene expression," *Proc. Natl. Acad. Sci. USA* 95:12989-12994, The National Academy of Sciences (1998).
Aiyar, A., et al., "The plasmid replicon of EBV consists of multiple *cis*-acting elements that facilitate DNA synthesis by the cell and a viral maintenance element," *EMBO J. 17*:6394-6403, Oxford University Press (1998).
Altman, A.L., and Fanning, E., "Defined Sequence Modules and an Architectural Element Cooperate To Promote Initiation at an Ectopic Mammalian Chromosomal Replication Origin," *Mol. Cell. Biol. 24*:4138-4150, American Society for Microbiology (May 2004).
Berglund, P., et al., "Alphaviruses as vectors for gene delivery," *Trends Biotechnol. 14*:130-134, Elsevier Science Ltd. (1996).
Blasey, H.D., et al., Mammalian Transient Gene Expression-Potential, Practical Application and Perspectives in: *Animal Cell Technology:Products from Cells, Cells as Products*, Bernard, A., et al., eds., Kluwer Academic Publishers, Norwell, MA, pp. 331-337 (1999).
Bode, J. et al., "The Hitchhiking Principle: Optimizing episomal vectors for the use in gene therapy and biotechnology," *Gene Ther. Mol. Biol. 6*:33-46, Gene Therapy Press (2001).
Bohl, D., et al., "Long-term control of erythropoietin secretion by doxycycline in mice transplanted with engineered primary myoblasts," *Nat. Med. 3*:299, Nature Publishing Company (1997).
Boorsma, M., et al., "A temperature-regulated replicon-based DNA expression system," *Nature Biotech. 18*:429-432, Nature America Inc. (2000).
Borrsma, M., et al., "Alphavirus cDNA-Based Expression Vectors: Effects of RNA Transcription and Nuclear Export," *Biotechnol. Bioeng. 81*:553-562, Wiley Periodicals Inc. (Mar. 2003).
Bredenbeek, P.J., et al., "Sindbis Virus Expression Vectors: Packaging of RNA Replicons by Using Defective Helper RNAs," *J. Virol. 67*:6439-6446, American Society for Microbiology (1993).
Brown, J.W., "The Ribonuclease P Database," *Nucleic Acids Res. 26*:351-352, Oxford University Press (1998).
Burge, B.W. and Pfefferkorn, E.R., "Complementation Between Temperature-sensitive Mutants of Sindbis Virus," *Virol. 30*:214-223, Academic Press (1966).
Burge, B.W. and Pfefferkorn, E.R.,"Isolation and Characterization of Conditional-lethal Mutants of Sindbis Virus," *Virol. 30*:204-213, Academic Press (1966).
Ceccarelli, D. F. and Frappier, L., "Functional Analyses of the EBNA1 Origin DNA Binding Protein of Epstein-Barr Virus," *J. Virol. 74*:4939-48, American Society for Microbiology (2000).
Chapman, K.B. and Szostak, J.W., "Isolation of a ribozyme with 5'-5' ligase activity," *Chem. Biol. 2*:325-333, Current Biology Ltd. (1995).

(Continued)

*Primary Examiner*—James S Ketter
(74) *Attorney, Agent, or Firm*—Sterne, Kessler, Goldstein & Fox P.L.L.C.

(57) ABSTRACT

The present invention relates to nucleic acid molecules and in particular to vectors, comprising at least one gene of interest, at least one scaffold/matrix attached region (S/MAR), at least one origin of replication, and at least one replication initiation factor, cells comprising these, processes for their propagation, and their use, in particular for the high level expression of proteins which can be used as medicaments.

98 Claims, 4 Drawing Sheets

OTHER PUBLICATIONS

Chomczynski P. and Sacchi, N., "Single-Step Method of RNA Isolation by Acid Guanidinium Thiocyanate-Phenol-Chloroform Extraction," *Anal. Biochem. 162*:156-159, Academic Press (1987).
Clark, H.F., et al., "Comparative Characterization of a C-type Virus-Producing Cell line (VSW) and a Virus-Free Cell Line (VH2) From *Vipera russelli,*" *J. Natl. Cancer Inst. 51*:645, Oxford University Press (1973).
Dang, Q., et al., "Human Beta Interferon Scaffold Attachment Region Inhibits De Novo Methylation and Confers Long-Term, Copy Number-Dependent Expression to a Retroviral Vector," *J. Virol. 74*:2671-8, American Society for Microbiology (2000).
Davis, N.L., et al., "In Vitro Synthesis of Infectious Venezuelan Equine Encephalitis Virus RNA from a cDNA Clone: Analysis of a Viable Deletion Mutant," *Virol. 171*:189-204, Academic Press (1989).
Doedens, J., et al., "Inhibition of Endoplasmic Reticulum-to-Golgi Traffic by Poliovirus protein 3A: Genetic and Ultrastructural Analysis," *J. Virol. 71*:9054-9064, American Society for Microbiology (1997).
Dryga, S.A., et al., "Identification of Mutations in a Sindbis Virus Variant Able to Establish Persistent Infection in BHK Cells: The Importance of a Mutation in the nsP2 Gene," *Virol. 228*:74-83, Academic Press (1997).
Dubensky, Jr., T.W., et al., "Sindbis Virus DNA-Based Expression Vectors: Utility for In Vitro and In Vivo Gene Transfer," *J. Virol. 70*:508-519, American Society for Microbiology (1996).
Durocher, Y., et al., "High-level and high-throughput recombinant protein production by transient transfection of suspension-growing human 293-EBNA1 cells," *Nucleic Acids Res 30*:E9, Oxford University Press (Jan. 2002).
Früh, K., et al., "Displacement of housekeeping proteasome subunits by MHC-encoded LMPs: a newly discovered mechanism for modulating the multicatalytic proteinase complex," *EMBO J. 13*:3236, Oxford University Press (1994).
Furth, P.A., et al., "Temporal control of gene expression in transgenic mice by a tetracycline-responsive promoter," *Proc. Natl. Acad. Sci. USA 91*:9302-9306, The National Academy of Sciences (1994).
Garoff, H. and Li, K.-J., "Recent advances in gene expression using alphavirus vectors," *Curr. Opin. Biotechnol. 9*:464-469, Current Biology Ltd. (1998).
Gossen, M. and Bujard, H., "Tight control of gene expression in mammalian cells by tetracycline-responsive promoter," *Proc. Natl. Acad. Sci. USA 89*:5547-51, The National Academy of Sciences (1992).
Grignani, F., et al., "High-Efficiency Gene Transfer and Selection of Human Hematopoietic Progenitor Cells with a Hybrid EBV/Retroviral Vector Expressing the Green Fluorescence Protein," *Cancer Res 58*:14-19, American Association for Cancer Research (1998).
Hennighausen, L., et al., "Conditional Gene Expression in Secretory Tissues and Skin of Transgenic Mice Using the MMTV-LTR and the Tetracycline Responsive System," *J. Cell. Biochem. 59*:463-472, Wiley-Liss Inc.(1995).
Herweijer, H., et al., "A Plasmid-Based Self-Amplifying Sindbis Virus Vector," *Hum. Gene Ther. 6*:1495-1501, Mary Ann Liebert Inc. (1995).
Hirt, B., "Selective extraction of polyoma DNA from infected mouse cell cultures," *J. Mol. Biol. 26*:365-369, Academic Press (1967).
Hoffmann, A., et al., "A novel tetracycline-dependent expression vector with low basal expression and potent regulatory properties in various mammalian cell lines," *Nucleic Acids Res. 25*:1078-1079, Oxford University Press (1997).
Holowaty, M., et al., "Protein Profiling with Epstein-Barr Nuclear Antigen-1 Reveals an Interaction with the Herpesvirus-associated Ubiquitin-specific Protease HAUSP/USP7," *J Biol Chem. 278*:29987-94, The American Society for Biochemistry and Molecular Biology, Inc. (Aug. 2003).
Howe, J.R., et al., "The Responsiveness of a Tetracycline-sensitive Expression System Differs in Different Cell Lines," *J. Biol. Chem. 23*:14168-14174, The American Society for Biochemistry and Molecular Biology, Inc. (1995).
Hung, S.C., et al., "Maintenance of Epstein-Barr virus (EBV) *oriP*-based episomes requires EBV-encoded nuclear antigen-1 chromosome-binding domains, which can be replaced by high-mobility group-I or histone H1," *Proc. Natl. Acad. Sci. USA 98*:1865-1870, The National Academy of Sciences (2001).
Jordan, M., et al., "Calcium-phosphate mediated DNA transfer into HEK-293 cells in suspension: control of pyhsicochemical parameters allows transfection in stirred media," *Cytotechnol. 26*:39-47, Kluwer Academic Publishers (1998).
Kanda, T., et al., "Coupling of Mitotic Chromosome Tethering and Replication Competence in Epstein-Barr Virus-Based Plasmids," *Mol. Cell. Biol. 21*:3576-3588, American Society for Microbiology (2001).
Kistner, A., et al., "Doxycycline-mediated quantitative and tissue-specific control of gene expression in transgenic mice," *Proc. Natl. Acad. Sci. USA 93*:10933-10938, The National Academy of Sciences (1996).
Koons, M.D., et al., "The Replicator of the Epstein-Barr Virus Latent Cycle Origin of DNA Replication, *oriP*, Is Composed of Multiple Functional Elements," *J. Virol. 75*:10582-92, American Society for Microbiology (2001).
Kuhn, R.J., et al., "Chimeric Sindbis-Ross River Viruses To Study Interactions between Alphavirus Nonstructural and Structural Regions," *J. Virol. 70*:7900-7909, American Society for Microbiology (1996).
Kusano, S., et al., "Epstein-Barr Virus Nuclear Antigen-1-Dependent and —Independent *oriP*-Binding Cellular Proteins," *Intervirology 44*:283-290, S. Karger AG (2001).
Lavrovsky, Y., et al., "Therapeutic Potential and Mechanism of Action of Oligonucleotides and Ribozymes," *Biochem. Mol. Med. 62*:11-22, Academic Press (1997).
Leake, C.J., et al., "Cytopathic Effect and Plaque Formation by Arboviruses in a Continuous Cell Line (XTC-2) from the Toad *Xenopus laevis,*" *J. Gen. Virol. 35*:335-339, Society For General Microbiology (1977).
Lee, A.H., et al., "Comparison of Various Expression Plasmids for the Induction of Immune Response by DNA Immunization," *Mol. Cells. 7*:495-501, The Korean Society for Molecular Biology (1997).
Lee, K. H., et al., "Two-Dimensional Electrophoresis of Proteins as a Tool in the Metabolic Engineering of Cell Cycle Regulation," *Biotech. Bioeng.* 50:336-340, Jonh Wiley & Sons, Inc.(1996).
Lemm, J.A., et al., "Mutations Which Alter the Level of Structure of nsP4 Can Affect the Efficiency of Sindbis Virus Replication in a Host-Dependent Manner," *J. Virol. 64*:3001-3011, American Society for Microbiology (1990).
Liebich, I., et al., "S/MARt DB: a database on scaffold/matrix attached regions," *Nucleic Acids Res. 30*:372-374, Oxford University Press (Jan. 2002).
Liljeström, P., "Alphavirus expression systems," *Curr. Opin. Biotechnol. 5*:495-500, Current Biology Ltd (1994).
Liljeström, P., and Garoff, H., "A New Generation of Animal Cell Expression Vectors Based on the Semliki Forest Virus Replicon," *Bio/Technology 9*:1356-1361, Nature Publishing Company (1991).
Lundstrom, K., "Alphaviruses as expression vectors," *Curr. Opin. Biotechnol. 8*:578-582, Current Biology (1997).
Lundstrom, K., et al., "Semliki Forest virus vectors: efficient vehicles for in vitro and in vivo gene delivery," *FEBS Lett. 504*:99-103, Elsevier Science B.V. (2001).
Lundstrom, K., et al., "Semliki Forest virus vectors for in vitro and in vivo applications," *Gene Ther. Mol. Biol. 4*:23-31, Gene Therapy Press (1999).
Máthé, E., et al., "The *Tomaj* mutant alleles of α*Tubulin67C* reveal a requirement for the encoded maternal specific tubulin isoform in the sperm aster, the cleavage spindle apparatus and neurogenesis during embryonic development in *Drosophila*," *J. Cell Sci. 111*:887-896, The Company of Biologists Limited (1998).
Meissner, P., et al., "Transient Gene Expression: Recombinant Protein Production with Suspension-Adapted HEK293-EBNA Cells," *Biotechnol. Bioeng. 75*:197-203, John Wiley & Sons, Inc. (2001).
Miller, A.D. and Rosman, G.J., "Improved Retroviral Vectors for Gene Transfer and Expression," *Biotechniques 7*:980-982, (1989).
Moore, J.C., et al., "Strategies for the in vitro Evolution of Protein Function: Enzyme Evolution by Random Recombination of Improved Sequences," *J. Mol. Biol. 272*:336-47, Academic Press (1997).
Patterson, B., et al., "Cold-sensitive Mutants G680V and G691C of *Dictyostelium* Myosin II Confer Dramatically Different Biochemical Defects," *J. Biol. Chem.* 272:27612-27617, The American Society for Biochemistry and Molecular Biology, Inc. (1997).

Piechaczek, C., et al., "A vector based on the SV40 origin of replication and chromosomal S/MARs replicates episomally in CHO cells," *Nucleic Acids Res* 27:426-8, Oxford University Press (1999).

Poljak, L., et al., "SARs stimulate but do not confer position independent gene expression," *Nucleic Acids Res.* 22:4386-4394, Oxford University Press (1994).

Rawlins, D.R., et al., "Sequence-Specific DNA Binding of the Epstein-Barr Virus Nuclear Antigen (EBNA-1) to Clustered Sites in the Plasmid Maintenance Region," *Cell* 42:859-68, MIT (1985).

Reisman, D., et al., "A Putative Origin of Replication of Plasmids Derived from Epstein-Barr Virus Is Composed of Two cis-Acting Components," *Mol. Cell. Biol.* 5:1822-1832, American Society for Microbiology (1985).

Renner, W., et al., "Recombinant Cyclin E Expression Activates Proliferation and Obviates Surface Attachment of Chinese Hamster Ovary (CHO) Cells in Protein-Free Medium," *Biotech. Bioeng.* 47:476-82, John Wiley & Sons Inc. (1995).

Rikkonen, M., "Functional Significance of the Nuclear-Targeting and NTP-Binding Motifs of Semliki Forest Virus Nonstructural Protein nsP2," *Virol.* 218:352-361, Academic Press, Inc. (1996).

Saez, E., et al., "Inducible gene expression in mammalian cells and transgenic mice," *Curr. Opin. Biotechnol.* 8:608-616, Current Biology Ltd. (1997).

Schlesinger, S., "Alphavirus Expression Vectors," *Adv. Virus Res.* 55:565-577; Academic Press (2000).

Schlesinger, S., "Alphavirus vectors: development and potential therapeutic applications," *Exp. Opin. Biol. Ther.* 1:177-191, Ashley Publications Ltd. (2001).

Schlesinger, S., "Alphaviruses—vectors for the expression of heterologous genes," *Trends Biotechnol.* 11:18-22, Elsevier Science (1993).

Schwer, B., et al., "Effects of deletion mutations in the yeast Ces1 protein on cell growth and morphology and on high copy suppression of mutations in mRNA capping enzyme and translation initiation factor 4A," *Nucleic Acids Res.* 26:803-809, Oxford University Press (1998).

Sena-Estevez, M., et al., "Single-Step Conversion of Cells to Retrovirus Vector Producers with Herpes Simplex Virus-Epstein-Barr Virus Hybrid Amplicons," *J. Virol.* 73:10426-10439, American Society for Microbiology (1999).

Shockett, P., et al., "A modified tetracycline-regulated system provides autoregulatory, inducible gene expression in cultured cells and transgenic mice," *Proc. Natl. Acad. Sci. USA* 92:6522-6526, The National Academy of Sciences (1995).

Shockett, P.E., and Schatz, D.G., "Diverse strategies for tetracycline-regulated inducible gene expression," *Proc. Natl. Acad. Sci. USA* 93:5173, The National Academy of Sciences (1996).

Smith, S.M., et al., "Efficient Expression by an Alphavirus Replicon of a Functional Ribozyme Targeted to Human Immunodeficiency Virus Type 1," *J. Virol.* 71:9713-9721, American Society for Microbiology (1997).

Smyth, J., et al., "Efficient Multiplication of a Semliki Forest Virus cCimera Containing Sindbis Virus Spikes," *J. Virol.* 71:818-823, American Society for Microbiology (1997).

Strauss, J.H. and Strauss, E.G., "The Alphaviruses: Gene Expression, Replication, and Evolution," *Microbiol. Rev.* 58:491-562, American Society for Microbiology (1994).

Takebe, Y. et al., "SRα Promoter: an Efficient and Versatile Mammalian cDNA Expression System Composed of the Simian Virus 40 Early Promoter and the R-U5 Segment of Human T-Cell Leukemia Virus type 1 Long Terminal Repeat," *Mol. Cell. Biol.* 8:466-472, American Society for Microbiology (1988).

Tan, B.T., et al., "An Adenovirus-Epstein-Barr Virus Hybrid Vector That Stably Transforms Cultured Cells with High Efficiency," *J. Virol.* 73:7582-7589, American Society for Microbiology (1999).

Wang, S. and Vos, J.M., "A Hybrid Herpesvirus Infectious Vector Based on Epstein-Bar Virus and Herpes Simplex Virus Type 1 for Gene Transfer into Human Cells In Vitro and In Vivo," *J Virol.* 70:8422-30, American Society for Microbiology (1996).

Weaver, S.C., et al., "Recombinatorial History and Molecular Evolution of Western Equine Encephalomyelitis Complex Alphaviruses," *J. Virol* 71:613-623, American Society for Microbiology (1997).

Weiss, B., et al., "Establishment and Maintenance of Persistent Infection by Sindbis Virus in BHK Cells," *J. Virol.* 33:463-474, American Society for Microbiology (1980).

Wimmel, A., et al., "Inducible acceleration of $G_1$ progression through tetracycline-regulated expression of human cyclin E," *Oncogene* 9:995-997, Macmillan Press Ltd (1994).

Wu, A.M., "In vivo veritas: Live phage display panning," *Nature Biotech.* 14:429-431, (1996).

Wu, H., et al., "Separation of the DNA Replication, Segregation, and Transcriptional Activation Functions of Epstein-Barr Nuclear Antigen 1," *J. Virol.* 76:2480-90, American Society for Microbiology (Mar. 2002).

Wurm, F. and Bernard, A., "Large-scale transient expression in mammalian cells for recombinant protein production," *Current Opinion in Biotechnology* 10:156-159, Elsevier Science (1999).

Xie, Y., et al., "A ribozyme-mediated, gene "knockdown" strategy for the identification of gene function in zebrafish," *Proc. Natl. Acad. Sci. USA* 94:13777-13781, The National Academy of Sciences (1997).

Xiong, C., et al., "Sindbis Virus: An Efficient, Broad Host Range Vector for Gene Expression in Animal Cells," *Science* 243:1188-1191, The American Association for the Advancement of Science (1989).

Yates, J. L., et al., "Stable replication of plasmids derived from Epstein-Barr virus in various mammalian cells," *Nature* 313:812-815, Nature Publishing Group (1985).

Yates, J.L., et al., "The Minimal Replicator of Epstein-Barr Virus oriP," *J. Virol.* 74:4512-22, American Society for Microbiology (2000).

Yu, H., et al., "Inducible Human Immunodeficiency Virus Type 1 Packaging Cell Lines," *J. Virol.* 70:4530-4537, American Society for Microbiology (1996).

Zang, M., et al., "Production of Recombinant Proteins in Chinese Hamster Ovary Cells Using a Protein-Free Cell Culture Medium," *Bio/Technology* 13:389-92, Nature Publishing Company (1995).

Jankelevich, S., et al., "A nuclear matrix attachment region organizes the Epstein-Barr viral plasmid in Raji cells into a single DNA domain," *The EMBO Journal* 11:1165-1176, Oxford University Press (1992).

Klehr, D., et al., "Scaffold-Attached Regions from the Human Interferon β Domain Can Be Used To Enhance the Stable Expression of Genes under the Control of Various Promoters," *Biochemistry* 30:1264-1270, American Chemical Society (1991).

Lipps, H.J, et al., "Chromosome-based vectors for gene therapy," *Gene* 304:23-33, Elsevier Science B.V. (Jan. 2003).

Lipps, H.J., et al., "Exploiting chromosomal and viral strategies: The design of safe and efficient non-viral gene transfer systems," *Curr. Opin. Mol. Ther.* 3:133-141, Current Drugs (2001).

Mearini, G., et al., "Interaction of EBV latent origin of replication with the nuclear matrix: identification of S/MAR sequences and protein components," *FEBS Lett* 547:119-124, Elsevier Science B.V. (Jun. 2003).

Wendelburg, B.J, and Vos, J.-M.H., "An enhanced EBNA1 variant with reduced IR3 domain for long-term episomal maintenance and transgene expression of oriP-based plasmids in human cells," *Gene Therapy* 5:1389-1399, Nature Publishing Group (1998).

Tsukamoto, H., et al., "Enhanced expression of recombinant dystrophin following intramuscular injection of Epstein-Barr virus (EBV)-based mini-chromosome vectors in mdx mice," *Gene Therapy* 6:1331-1335, Nature Publishing Group (1999).

International Search Report for International Application No. PCT/EP2004/007556, European Patent Office, Netherlands, mailed on Oct. 26, 2004.

GENE EXPRESSION SYSTEM

CROSS-REFERENCE TO RELATED APPLICATIONS

This application claims the benefit of International Patent Application No. PCT/EP2004/007556, filed on Jul. 9, 2004 by Cytos Biotechnology AG, under the same title and naming the same inventors as the present application. This application also claims the benefit of U.S. Provisional Patent Application Nos. 60/486,238, filed Jul. 11, 2003 and 60/524,852, filed Nov. 26, 2003, the contents of which are relied upon and incorporated by reference in their entireties.

BACKGROUND OF THE INVENTION

1. Field of the Invention

The present invention relates to compositions and methods for high level expression of polypeptides. The invention provides nucleic acid molecules, expression systems, host cells, methods and kits that are useful for the production of polypeptides and/or untranslated RNA molecules. Due to the improved expression levels of polypeptides or untranslated RNA molecules the invention is particularly useful for the rapid production of large quantities of recombinant proteins such as monoclonal antibodies which can be used as drugs.

2. Related Art

Process development for biopharmaceuticals, and hereby in particular the expression of polypetides used in these biopharmaceuticals, is governed by the economy of the manufacturing process. The classical approach for the production of recombinant polypetides is the use of stable expression systems. These systems are based on chromosomal integration of an expression plasmid into the genome of the host cell. The sites of gene integration, however, are random, and the number and ratio of genes integrating at any particular site are unpredictable. As a result, it is normally necessary to screen many clonal cell populations to obtain a cell line in which the desired genes are expressed at an appropriate level. This procedure of transfection, selection and analysis of numerous clonally derived cell lines expressing the multiple genes is costly and time-consuming.

An alternative to stable expression systems for gene expression are transient expression systems. The expression of the latter systems is based on non-integrated plasmids, and hence the expression is typically rapidly lost as the cell undergoes division. Thus, transient expression systems typically do not lead to sufficient expression over time implying that repeated processes would be necessary which might be not desirable.

Another way of performing expression is by transfection of an episomal vector which replicates extra-chromosomally in a host cell such as in a mammalian host cell. Episomal replicating vectors provide certain advantages over classical expression systems since they do not integrate into the host genome, but replicate episomally in a host cell. Most of the described episomally replicating vectors are based on viral components from viruses like Papovaviridae (e.g. SV40, BPV) or Herpesviridae (e.g. EBV). Episomal replicating vectors derived from these viruses generally contain a replication origin and at least one viral trans-acting factor, e.g., an initiator protein. Examples of such initiator proteins are large T-antigen for SV40, E1/E2 for BPV, and EBNA-1 for EBV. The process of episomal replication typically involves both host cell replication machinery and virus trans-acting factors.

To increase expression, retrovirus vectors stably integrated in transduced resting cells have been described using a chromosomal scaffold/matrix attached regions (S/MAR) element derived from human INF-beta gene (U.S. Pat. No. 6,194,212 B1). It has further been shown for stably integrated retrovirus vectors that human INF-beta SAR inhibits de novo methylation, alleviates methylation-mediated transcriptional repression and allows for higher level gene expression (Dang et al., (2000) J Virol 74, 2671-2678). Episomal vectors having a S/MAR element were described for delivery in gene therapy. However, to avoid any type of cell transformation induced by viral trans-acting factors, the viral trans-acting factor was replaced by S/MAR (U.S. Pat. No. 6,410,314 B1; Piechaczek et al., NAR, 1999, Vol 27, No. 2; Bode et al., 2001 Gene Ther Mol Biol, Vol. 6, 33-46).

However, the enhancing effect of S/MAR on promoter functions and gene expression has been reported to be restricted to the integrated state of transfected templates. Thus, in transient expression systems for the expression of proteins, and therefore in expression systems based on plasmids which are not integrated in the genome of the host cell, the effect of S/MAR on the expression levels of proteins has been reported to have an antagonizing effect (Klehr et al., (1991) Biochemistry, 30(5):1264-70; Poljak et al., (1994) Nucleic Acid Res., 22(21):4386-94; Wu et al., (2001) Sheng, 33(1):59-64).

A need remains in the art for compositions and methods other than stable expression systems that allow rapid production of large quantities of polypeptides and untranslated RNA molecules, and in particular for compositions and methods that allow increased expression levels of a desired protein compared to compositions and methods known in the art.

BRIEF SUMMARY OF THE INVENTION

The present invention solves this need and provides compositions and methods for the production of polypeptides and/or untranslated RNA molecules that result in expression of polypeptides and/or untranslated RNA molecules at very high rates and amounts. In particular, the present invention provides compositions and methods for episomal replication in a transient or semi-stable expression system which results in increased expression of proteins.

Thus, the present invention provides nucleic acid molecules, expression systems, recombinant host cells that permit the production of polypeptides and/or untranslated RNA molecules. Also provided are methods for making the nucleic acid molecules, expression systems and host cells of the invention. The invention further provides methods for producing polypeptides and/or untranslated RNA molecules.

In a general aspect, the present invention provides for a nucleic acid molecule comprising (a) at least one, preferably one or two, genes of interest (A1, A2, A3 . . . ); (b) at least one, preferably one, scaffold/matrix attached region (S/MAR) (B1, B2, B3 . . . ); (c) at least one, preferably one or two, origin of replication (ORI) (C1, C2, C3 . . . ); and (d) at least one, preferably one or two, replication initiation factor (D1, D2, D3 . . . ) capable of recognizing said at least one origin of replication. Thus, the at least one replication initiation factor preferably recognizes the at least one origin of replication leading to replication of the at least one origin of replication. The S/MAR element is preferably originating from the 5'region of the interferon beta gene (SEQ ID NO: 3).

In a preferred aspect, the invention provides a nucleic acid molecule, wherein the first of the at least one gene of interest (abbreviated as A1), the first of the at least one scaffold/matrix attached region (S/MAR) (abbreviated B1), the first of the at least one origin of replication (ORI) (abbreviated C1), and the first of the at least one replication initiation factor (abbreviated D1) capable of recognizing the origin of replication are positioned on said nucleic acid molecule in a consecutive order selected from (a) the consecutive order of A1-B1-C1-D1; and (b) the consecutive order of A1-C1-D1-B1.

In a preferred embodiment, the nucleic acid molecule of the invention is an episomally replicating expression vector. Thus, the inventive nucleic acid molecules, expression systems and vector systems of the present invention allow for transient transfection, selection, and generation of semi-stable cell populations, and very rapid production of polypeptides eliminating the need of isolating stably transformed high producing cell clones.

In a further general aspect, the present invention provides an expression system comprising one or more nucleic acid molecules, wherein said one or more nucleic acid molecules comprises (a) at least one, preferably one or two, genes of interest (A1, A2, A3 . . . ); (b) at least one scaffold/matrix attached region (S/MAR) (B1, B2, B3 . . . ); (c) at least one origin of replication (ORI) (C1, C2, C3 . . . ); and (d) at least one replication initiation factor (D1, D2, D3 . . . ) capable of recognizing said at least one origin of replication. Thus, preferably the at least one replication initiation factor recognizes the at least one origin of replication leading to replication of the origin of replication.

Moreover, according to a further aspect, the present invention provides an expression system comprising (a) at least one, preferably one or two, genes of interest (A1, A2, A3 . . . ); (b) at least one scaffold/matrix attached region (S/MAR) (B1, B2, B3 . . . ); (c) at least one origin of replication (ORI) (C1, C2, C3 . . . ); and (d) at least one replication initiation factor (D1, D2, D3 . . . ) capable of recognizing said at least one origin of replication. Preferably the at least one gene of interest, the at least one S/MAR, and the at least one origin of replication (ORI) are present on a first nucleic acid molecule, and the at least one replication initiation factor is present on a second nucleic acid molecule.

In another preferred embodiment, the expression system comprises a first and a second origin of replication and a first and second replication initiation factor, wherein the first replication initiation factor is capable of recognizing the first origin of replication and wherein the second replication initiation factor is capable of recognizing the second origin of replication. Preferably, the first origin of replication is the EBV OriP, the first replication initiation factor is the EBNA1 gene, the second origin of replication is the SV40 ori, and the second replication initiation factor is SV40 large T-antigen.

The nucleic acid molecules of the expression systems of the invention may be maintained at, or accumulated to, multiple copies in the nuclei of recombinant host cells, preferably of transfected mammalian cells. The nucleic acid molecules and expression systems of the invention are particularly useful for transient transfection, selection, and the generation of semi-stable cell populations leading to high expression levels of proteins at early and late-time points as well as to high proliferation rates in cells.

In one aspect, the at least one gene of interest (GOI) of the invention encodes one or more cytokine, light and/or heavy chain of an antibody, lymphokine, tumor necrosis factor, interferon, toxic protein, prodrug converting enzyme, or other polypeptide.

In yet another aspect, the at least one gene of interest of the invention encodes an untranslated RNA molecule, such as an antisense RNA molecule, tRNA molecule, rRNA molecule, or ribozyme.

The invention also provides methods for making recombinant host cells comprising introducing nucleic acid molecules of the invention into host cells. Further provided are recombinant host cells produced by the introduction of nucleic acid molecules of the invention. In one embodiment, one, some or all of these recombinant host cells contain one or more nucleic acid molecules comprising (a) at least one, preferably one or two, genes of interest (A1, A2, A3 . . . ); (b) at least one scaffold/matrix attached region (S/MAR) (B1, B2, B3 . . . ); (c) at least one origin of replication (ORI) (C1, C2, C3 . . . ); and (d) at least one replication initiation factor (D1, D2, D3 . . . ) capable of recognizing said at least one origin of replication. The at least one replication initiation factor, in certain embodiments, may be stably integrated into the genome of the one, some or all host cells.

In a very preferred embodiment, the recombinant host cell of the invention comprises (a) at least one, preferably two genes of interest (A1, A2), (b) at least one S/MAR (B1), (c) a first and a second origin of replication (C1, C2), and (d) a first and second replication initiation factor (D1, D2), wherein the first replication initiation factor is capable of recognizing the first origin of replication and wherein the second replication initiation factor is capable of recognizing the second origin of replication. Preferably, the first origin of replication is the EBV OriP, the first replication initiation factor is the EBNA1 gene, the second origin of replication is the SV40 ori, and the second replication initiation factor is SV40 large T-antigen. Preferably the at least one gene of interest, the at least one S/MAR, the first and second origin of replication, and the first replication initiation factor are present on a first nucleic acid molecule, and the second replication initiation factor, preferably the SV40 large T-antigen is stably integrated into the genome of the at least one recombinant host cell.

The present invention also provides methods for producing polypeptides and untranslated RNA molecules in recombinant host cells, said methods comprising introducing a nucleic acid molecule of the invention into a host cell to produce a recombinant host cell, and culturing the recombinant host cell under conditions suitable for expression of said polypeptide or untranslated RNA molecule. The methods of the invention may further comprise recovering said polypeptide or untranslated RNA molecule.

Methods are also provided for the expression of polypeptides, including cytokines, lymphokines, tumor necrosis factors, interferons, toxic polypeptides, light and/or heavy chain of an antibody, and prodrug converting enzymes.

In certain embodiments, the methods of the invention involve introducing the nucleic acid molecules of the invention into prokaryotic or eukaryotic host cells to produce a recombinant host cell, and then culturing said recombinant host cell under suitable culture conditions. The recombinant host cells may be cultured, e.g., in a serum-free or protein-free medium.

The present invention also provides pharmaceutical compositions comprising nucleic acid molecules of the invention and a pharmaceutically acceptable carrier.

Also included within the invention are kits comprising the nucleic acid molecules of the invention. Kits of the invention may additionally or alternatively comprise one or more expression systems of the invention and one or more recombinant host cells of the invention.

DETAILED DESCRIPTION OF THE INVENTION

Figure 1A:
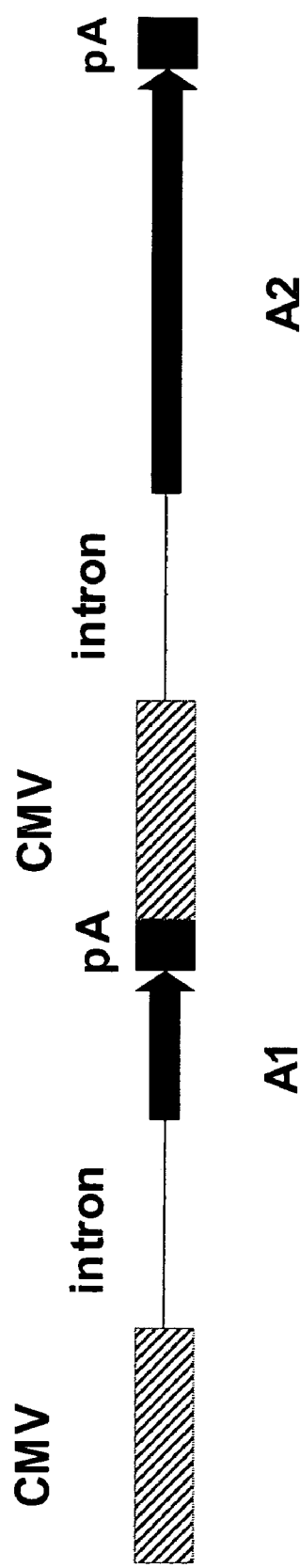
FIG. 1A shows a schematic representation of the expression cassette (A1A2) used for the testing of the novel expression vectors. This expression cassette leads to the expression of a complete antibody. CMV promoters are shown as hatched boxes, the introns are shown as lines, the polyadenylation signals (pA) are shown as black boxes, the cDNA of the light chain (A1) and the genomic sequence of the heavy chain (A2) are shown as black arrows. The complete cassette was introduced into the different expression vectors.

As used herein, the term "purified" used in reference to a molecule means that the concentration of the molecule being purified has been increased relative to molecules associated with it in its natural environment. Naturally associated molecules include polypeptides, nucleic acids, lipids and sugars but generally do not include water, buffers, and reagents added to maintain the integrity or to facilitate the purification of the molecule. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

As used herein, the term "gene of interest" refers to a nucleic acid sequence comprising the coding sequence for the gene of interest which can be either spaced by introns or which is a cDNA encoding the open reading frame. Typically and preferably, the term "gene of interest", as used herein, refers to a nucleic acid sequence further comprising a promoter, preferably a promoter that activates the gene of interest, and even more preferably, to a nucleic acid sequence further comprising a promoter and a polyadenylation signal sequence. This nucleic acid sequence may again further comprise an enhancer.

As used herein, the term "at least one gene of interest" of the inventive nucleic acid molecule refers to one, two, or more genes of interest. Preferred nucleic acid molecules of the invention comprise one or two genes of interest. The nucleic acid molecule of the invention preferably comprises a first gene of interest. In another preferred embodiment, the inventive nucleic acid molecule comprises two genes of interest, a first gene of interest and a second gene of interest. Preferably, the first gene of interest and the second gene of interest are positioned adjacent to each other. Alternatively, the first gene of interest and second gene of interest are not positioned adjacent to each other. In a further alternative embodiment, the nucleic acid molecule of the invention further comprises, in addition to the first and second gene of interest, a third gene of interest, a fourth gene of interest, or even more genes of interest. The third gene of interest, the fourth gene of interest or the even more genes of interest may be positioned adjacent to the first and/or second gene of interest or anywhere on the inventive nucleic acid molecule.

As used herein, the term "isolated" used in reference to a molecule means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need to be "purified."

As used herein, the phrase "individual" with respect to the administration of a pharmaceutical composition refers to multicellular organisms and includes both plants and animals. Preferred multicellular organisms are animals, more preferred are vertebrates, even more preferred are mammals, and most preferred are humans.

As used herein, the term "transcription" refers to the synthesis of RNA molecules from DNA templates in 5' to 3' direction catalyzed by RNA polymerases.

As used herein, the term "vector" refers to a polynucleotide construct, typically a plasmid or a virus, used to transmit genetic material to a host cell. Preferably, the term "vector" as used herein refers to an agent such as a plasmid, and even more preferably to a circular plasmid. A vector as used herein may be composed of either DNA or RNA. Preferably, a vector as used herein is composed of DNA.

As used herein, the term "episomally replicating vector" or "episomal vector" refers to a vector which is typically and very preferably not integrated into the genome of the host cell, but exists in parallel. An episomally replicating vector, as used herein, is replicated during the cell cycle and in the course of this replication the vector copies are distributed statistically in the resulting cells depending on the number of the copies present before and after cell division. Preferably, the episomally replicating vector may take place in the nucleus of the host cell, and preferably replicates during S-phase of the cell cycle. Moreover, the episomally replicating vector is replicated at least once, i.e. one or multiple times, in the nucleus of the host cell during S-phase of the cell cycle. In a very preferred embodiment, the episomally replicating vector is replicated once in the nucleus of the host cell during S-phase of the cell cycle.

As used herein, the phrase "untranslated RNA" refers to an RNA sequence or molecule which does not contain an open reading frame or encodes an open reading frame, or portion thereof, but in a format in which an amino acid sequence will not be produced (e.g., no initiation codon is present). Examples of such molecules are tRNA molecules, rRNA molecules, and ribozymes. Antisense RNA may be untranslated but, in some instances antisense sequences can be converted to a translatable sense strand from which a polypeptide is produced.

As used herein, the term "replication initiation factor" refers to a protein or a nucleic acid sequence comprising the coding sequence for such a protein or the coding sequence of the protein which can be spaced by introns, which replication initiation factor is able to recognize an origin of replication leading to replication of plasmids containing this origin of replication. Typically and preferably, the term "replication initiation factor", as used herein, refers to a nucleic acid sequence further comprising a promoter, preferably a promoter that activates the replication initiation factor, and even more preferably, to a nucleic acid sequence further comprising a promoter and a polyadenylation signal sequence. This nucleic acid sequence may again further comprise an enhancer. The nucleic acid molecule or expression vector, respectively, of the invention preferably comprises a first replication initiation factor. Alternatively, the nucleic acid molecule or expression vector, respectively, of the invention further comprises, in addition to the first replication initiation factor, a second replication initiation factor, a third replication initiation factor or even more replication initiation factors. The second or more replication initiation factors may be positioned adjacent to the first replication initiation factor or anywhere on the inventive nucleic acid molecule, or even on a separate nucleic acid molecule or stably integrated into the genome of a host cell. The second or more replication initiation factors may be the same or different from the first replication initiation factor. The second or more replication initiation factor recognizes an origin of replication leading to replication of plasmids containing this origin of replication. Typically and preferably, the second or more replication initiation factor recognizes the second or more origin of replication of the invention.

As used herein the term "functional variant of the at least one replication initiation factor" shall refer to a protein which has at least one amino acid exchange, i.e. substitution, deletion, insertion or truncation as compared to the wildtype, i.e. non-mutant, sequence of the protein and which is capable of recognizing the at least one origin of replication. Moreover, the term "functional variant of the at least one replication initiation factor", as used herein, shall refer to a protein which is capable of replicating plasmids containing the at least one origin of replication and which is capable of operating as a plasmid maintenance factor. Preferably, the term "functional variant of the at least one replication initiation factor" shall refer to a protein which display at least 20%, preferably at least 30%, more preferably at least 40%, even more preferably at least 50%, again more preferably at least 60%, again more preferably at least 70%, again more preferably at least 80%, again more preferably at least 90%, and again more preferably at least 100% of the replication activity or the episome maintenance activity, preferably of the replication activity and the episome maintenance activity, as compared to the wildtype protein in a specific cell line. Even more preferably, the term "functional variant of the at least one replication initiation factor" shall refer to a protein which display at least 150%, preferably at least 200%, more preferably at least 400%, even more preferably at least 600%, again more preferably at least 800%, and again more preferably at least 1000% of the replication activity or the episome maintenance activity, preferably of the replication activity and the episome maintenance activity, as compared to the wildtype protein in a specific cell line. Tests to determine the replication activity and the episome maintenance of a replication initiation factor are well known in the art and have been described in detail (Wu et al., Journal of Virology, 76 (2002), 2480-2490). Typically a plasmid containing the respective origin of replication is generated, and the corresponding wildtype or functional variant of the replication initiation, factor is provided on the same plasmid or in trans on another plasmid or integrated into the host cell chromosome. Then the replication activity and plasmid maintenance activity is measured as described in Wu et al. in the specific cell line, in which the replication activity and the maintenance of episomes is to be determined. In order to determine the relative replication and relative episome maintenance, these two parameters are measured for the wildtype replication initiation factor as well as for the respective functional variant under exactly the same, i.e. identical, conditions. The exact same conditions shall mean, in the same cell line, under the same transfection conditions, using the same medium and the same temperature of cultivation.

As used herein, the term "origin of replication" refers to a DNA sequence that is recognized by a replication initiation factor or a DNA replicase leading to replication of a plasmid containing the origin of replication. The expression "recognized by a replication initiation factor" is intended to mean that a replication initiation factor can physically interact with all or a portion of an origin of replication sequence, thereby causing or stimulating molecular mechanisms that ultimately cause all or a portion of the DNA molecule comprising the origin of replication to be replicated. The origin of replication, thus, typically comprises functionally required elements. One example for such functionally required elements are the family of repeats (FR) element or the dyad symmetry (DS) element of the EBV origin of replication (OriP). Further origin of replications comprising functionally required elements are well known in the art and are described for example in Bode J. et al. (2001, Gene Ther Mol Biol, v6, 33-46). The nucleic acid molecule or expression vector, respectively, of the invention preferably comprises a first origin of replication. Alternatively, the nucleic acid molecule or expression vector, respectively, of the invention further comprises, in addition to the first origin of replication, a second origin of replication, a third origin of replication or even more origin of replications. The second or more origin of replications may be positioned adjacent to the first origin of replication or anywhere on the inventive nucleic acid molecule or expression vector, respectively.

As used herein, the term "scaffold/matrix attached region (S/MAR)" refers to sequences of nucleic acids which attach chromatin loop domains to the nuclear matrix fiber, forming the boundaries for these DNA loops (Gasser et al. (1989) Int. Rev. Cytol. 119:57-96), and thus have importance for structure and function. The terms "scaffold/matrix attached region or scaffold/matrix attachment region (S/MAR)", "S/MAR", "S/MAR element", "matrix attachment region (MAR)", and "scaffold attachment region (SAR)", are used interchangeably. The S/MAR sequence of the present invention can be inserted in either of the two orientations into the nucleic acid molecule or expression vector, respectively, of the present invention. The nucleic acid molecule or expression vector, respectively, of the invention preferably comprises a first S/MAR. Alternatively, the nucleic acid molecule or expression vector, respectively, of the invention further comprises, in addition to the first S/MAR, a second S/MAR, a third S/MAR or even more S/MAR elements. The second, the third and/or more S/MAR element may be positioned adjacent to the first S/MAR or anywhere on the inventive nucleic acid molecule or expression vector, respectively.

The term "consecutive order", as used herein and referring to the positioning of the first of the at least one gene of interest (abbreviated as A1), the first of the at least one S/MAR (abbreviated as B1), the first of the at least one origin of replication (abbreviated as C1), and the first of the at least one replication initiation factor (abbreviated as D1) on the inventive nucleic acid molecule or expression system, respectively, means that A1, B1, C1 and D1 are positioned consecutively in a defined order. Preferred consecutive orders of the present invention are A1-B1-C1-D1 or A1-C1-D1-B1.

Moreover, the term "consecutive order", as used herein and referring to the positioning of A1, B1, C1 and D1 on the inventive nucleic acid molecule or expression system, respectively, should typically not be limited by the way such a consecutive order is identified with respect to a certain direction. In particular in the case of the very preferred embodiment, wherein said inventive nucleic acid is a cyclic expression vector, and preferably an episomally replicating cyclic expression vector, the consecutive order can be read in either direction which means, e.g. referring to a two dimensional illustration of the preferred inventive vector, in clockwise or anti-clockwise direction, so that the consecutive order of A1-B1-C1-D1 is the same as A1-D1-C1-B1 or D1-C1-B1-A1.

Unless specified otherwise, the promoter end of a polynucleotide sequence in sense orientation is the 5' end and the end of the polynucleotide sequence with the polyadenylation signal sequence is the 3' end. The 5' direction is herein also referred to as upstream of the polynucleotide sequence in sense orientation, while the 3' direction is also referred to as downstream of the polynucleotide sequence in sense orientation.

The term "CHO derived cell" or "293 derived cell" as used herein should refer to a CHO cell or a 293 cell that can be e.g. cells obtained from originating CHO or 293 cell lines by genetic engineering, cell fusion, extended passaging and medium-adaptation process and the like. More preferably the term "CHO derived cell" or "293 derived cell" as used herein should refer to a CHO cell or a 293 cell in which genome at least one gene have been added or removed. More preferably the term "CHO derived cell" or "293 derived cell" as used herein should refer to a CHO cell or a 293 cell in which genome at least one gene and preferably at most 6 genes, more preferably at most 5 genes, even more preferably at most 4 genes, again more preferably at most 3 genes, again more preferably at most 2 genes have been added or removed. Further preferred the term "CHO derived cell" or "293 derived cell" as used herein should refer to a CHO cell or a 293 cell in which genome one gene has been added or removed.

When the terms "one," "a," or "an" are used in this disclosure, they mean "at least one" or "one or more," unless otherwise indicated.

In a general aspect, the present invention provides for a nucleic acid molecule comprising (a) at least one gene of interest (A1, A2, A3 . . . ); (b) at least one scaffold/matrix attached region (S/MAR) (B1, B2, B3 . . . ); (c) at least one origin of replication (ORI) (C1, C2, C3 . . . ); and (d) at least one replication initiation factor (D1, D2, D3 . . . ) capable of recognizing said origin of replication. Thus, the replication initiation factor preferably recognizes the origin of replication leading to replication of the origin of replication.

The S/MAR element is preferably originating from the 5'region of the human interferon beta gene (SEQ ID NO: 3). Further S/MAR elements within the scope of the invention are any eukaryotic DNA elements which are involved in the generation of the loop structure found in chromatin. Such elements are typically A/T rich, in the range of 70% and show high affinity binding to the nuclear matrix. Methods for the identification of such S/MAR elements have been described (Sumer et al. Genome Res. 2003 July;13(7):1737-43). A comprehensive listing of S/MAR elements is found in the S/MAR t database, currently under http://transfac.gbf.de/SMARtDB/ and has been described by Liebich, I., Bode, J., Frisch,M. and Wingender, E.: S/MARt DB: A database on scaffold/matrix attached regions. Nucleic Acids Res. 30, 312-374 (2002).

Within the scope of the present invention are S/MAR elements that originate from mammals selected from the group consisting without limitation of human, simian, sheep and rodents, and herein typically mouse, rat, rabbit or hamster. Other S/MAR elements that can be used for the present invention are of chicken origin, of yeast, *Caenorhabditis elegans, Drosophila melanogaster* or virus origin and herein typically of EBV, SV40 or papilloma virus origin. In yet another embodiment, the S/MAR element is of plant origin, typically of tomato, *Arabidopsis thaliana*, tobacco, rice, pea, maize, potato, soybean, *petunia hybrida*, or *sorghum bicolour* origin. Preferred S/MAR elements useful in the present invention are of mammalian origin and herein in particular of human origin, most preferably originating from the 5'region of the human interferon beta gene.

In a preferred embodiment, the invention provides a nucleic acid molecule or expression vector, respectively, wherein the first of said at least one gene of interest (A1), the first of said at least one scaffold/matrix attached region (S/MAR) (B1), the first of said at least one origin of replication (ORI) (C1), and the first of said at least one replication initiation factor (D1) are positioned on said nucleic acid molecule or expression vector, respectively, in a consecutive order selected from (a) the consecutive order of A1-B1-C1-D1; and (b) the consecutive order of A1-C1-D1-B1. In a most preferred embodiment, A1, B1, C1, and D1 are in the consecutive order of A1-B1-C1-D1. In another most preferred embodiment, A1, B1, C1, and D1 are in the consecutive order of A1-C1-D1-B1. Alternatively, A1, B1, C1, and D1 are in the consecutive order of A1-C1-B1-D1.

In a further preferred embodiment, the first of the at least one gene of interest (A1) comprises a promoter (prom) and a stop signal sequence, preferably a polyadenylation signal sequence (pa), and the consecutive order is promA1pa-B1-

C1-D1. Such a consecutive order indicates that the first gene of interest (A1) comprising the promoter (prom) and the polyadenylation signal sequence (pa) is positioned on the nucleic acid molecule, and preferably on the episomally replicating expression vector, in such a way that the first scaffold/matrix attached region (S/MAR) (B1) is closer to the polyadenylation signal sequence (pa) and more distant to the promoter (prom) of the gene of interest. In another preferred embodiment, the first of the at least one replication initiation factor (D1) comprises a promoter (prom) and a stop signal sequence, preferably a polyadenylation signal sequence (pa), and the consecutive order is A1-B1-C1-paD1prom. In a particularly preferred embodiment, the first gene of interest and the first replication initiation factor comprise a promoter (prom) and a stop signal sequence, preferably a polyadenylation signal sequence (pa) and the consecutive order is promA1pa-B1-C1-paD1prom. Typically, the promoter end of a nucleic acid sequence, and herein typically the promoter end of the gene of interest or of the replication initiation factor, is to be understood as the 5' end of the mentioned nucleic acid sequence, whereas the polyadenylation signal sequence end of the nucleic acid sequence is to be understood as the 3' end of the nucleic acid sequence.

Each of the at least one gene of interest (A1, A2, A3 . . . ), the at least one S/MAR (B 1, B2, B3 . . . ), the at least one origin of replication (C1, C2, C3 . . . ), and the at least one replication initiation factor (D1, D2, D3 . . . ) can be positioned on the nucleic acid molecule or expression vector, respectively, in either orientation. Hence, a consecutive order of A1-B1-C1-D1 in accordance with this invention should include that the first of the at least one gene of interest (A1) may be in the orientation of promA1pa (which is the same as 5'(A1)3') or paA1prom (which is the same as 3'(A1)5') followed by 5'(B1)3' or 3'(B1)5' followed by 5'(C1)3' or 3'(C1)5' followed by 5'(D1)3' or 3'(D1)5'. In a preferred embodiment, A1 and D1 are in opposite orientation on the nucleic acid molecule or expression vector, respectively, which means that the first of the at least one replication initiation factor (D1) is positioned on the inventive nucleic acid molecule or expression vector, respectively, such that the direction of transcription of the first of the at least one replication initiation factor (D1) is in opposite direction as compared to the direction of transcription of the first of the at least one gene of interest (A1).

In the case of the very preferred embodiment, wherein said inventive nucleic acid is a cyclic expression vector, and preferably an episomally replicating cyclic expression vector, the consecutive order of the first and/or second of said at least one gene of interest (A1)(A2), the first of said at least one scaffold/matrix attached region (S/MAR) (B1), the first of said at least one origin of replication (ORI) (C1), and the first of said at least one replication initiation factor (D1) shall be understood, herein, as not to be limited to the direction of the consecutive order. Thus, the consecutive order, as referred herein can be read in either direction which means, e.g. referring to a two dimensional illustration of the preferred inventive vector, in clockwise or anti-clockwise direction so that the consecutive order of A1-B1-C1-D1 is the same as A1-D1-C1-B1 or D1-C1-B1-A1 or that the consecutive order of A1-C1-D1-B1 is the same as A1-B1-D1-C1. Further polynucleotides of any size which may confer additional functional characteristics such as selection markers or the like or which may not confer additional functional characteristics such as introns or the like can be inserted before and after of each of A1, B1, C1, and/or D1 positioned on the inventive nucleic acid molecule or expression vector, respectively.

In one embodiment, the distance between the first S/MAR element and the polyadenylation signal sequence of the first gene of interest is less than 30,000 base pairs (bp), less than 20,000 bp, less than 10,000 base pairs (bp), more preferably less than 5000 bp, more preferably less than 2000 bp, more preferably less than 1000 bp, even more preferably less than bp, less than 100bp, and most preferably less than 50 bp or even more preferably 6 bp or even zero base pairs. In another preferred embodiment, the distance between the S/MAR element (B1) and the first origin of replication is less than 30,000 base pairs (bp), less than 20,000 bp, less than 10,000 base pairs (bp), less than 5000 bp, less than 2000 bp, less than 1000 bp, less than 500 bp, 320 bp, less than 100 bp, or even zero base pairs.

In a most preferred embodiment, the distance between the first S/MAR element and the polyadenylation signal sequence of the first gene of interest is less than 500 bp, more preferably less than 100 bp. Most preferably, the distance between the first S/MAR element and the polyadenylation signal sequence of the first gene of interest is less than 50 bp. The preferred distance between the first S/MAR element and the first origin of replication (ORI) is less than 1000 bp, more preferably less than 500 bp.

In a further preferred embodiment of the present invention, A1, B1, C1, and D1 are in the consecutive order of A1-C1-D1-B1 on the nucleic acid molecule or expression vector, respectively. Preferably, the first replication initiation factor (D1) comprises a promoter (prom) and a stop signal sequence, preferably a polyadenylation signal sequence (pa), and the consecutive order A1-C1-paD1prom-B1. In another preferred embodiment, the first gene of interest (A1) comprises a promoter (prom) and a stop signal sequence, preferably a polyadenylation signal sequence (pa), and the consecutive order is promA1pa-C1-D1-B1. In a particularly preferred embodiment, the first gene of interest and the first replication initiation factor comprise a promoter (prom) and a stop signal sequence, preferably a polyadenylation signal sequence (pa), and the consecutive order is promA1pa-C1-paD1prom-B1. Thus, in this preferred embodiment, the first replication initiation factor, the first replication initiation factor is positioned interspersed between the first origin of replication (C1) and the first S/MAR element (B1) and in the orientation origin of replication-3'replication initiation factor5'-S/MAR. In case that the vector is a cyclic plasmid vector, the more preferred embodiment is to be understood as applying to the respective shorter interspersing distance in between S/MAR element and origin of replication.

In a further, particularly preferred embodiment, the distance between the first S/MAR element and the promoter, typically and preferably the 5' end of the promoter, of the first replication initiation factor on the nucleic acid molecule or expression vector, respectively, is less than 20,000 base pairs (bp), more preferably less than 10,000 bp, even more preferably less than 5000 bp, again even more preferably less than 2000 bp, again even more preferably less than 1000 bp, again even more preferably less than 500 bp, again even more preferably less than 100 bp, more preferably less than 50 bp, most preferably is equal to or less than 31 bp. Preferably, the distance between the first S/MAR element and the promoter of the first replication initiation factor is less than 500 bp, more preferably less than 100 bp, and most preferably less than 50 bp. In a most preferred embodiment, the distance between the first S/MAR element and the promoter of the first replication initiation factor on the vector, is less than 50 bp.

Further preferred is in relation to the above limits for the applicable distance between the first S/MAR element (B1) and the promoter of the first replication initiation factor (D1) that at the same time the first S/MAR element is spaced less than 30,000 base pairs (bp), more preferably less than 15,000 base pairs (bp), most preferably less than 8000 bp apart from at least either end of the first origin of replication (C1). Preferably, the distance between the S/MAR element (D1) and the first origin of replication (C1) is less than 4000 bp, preferably less than 3000 bp.

Typically and preferably, the location of the first scaffold/matrix attached region (S/MAR) on the nucleic acid molecule or expression vector, respectively, does not disrupt any coding sequence (does not destroy the protein function), in particularly not the replication initiation factor reading frame.

In a further embodiment of the invention, the nucleic acid molecule or expression vector, respectively, comprises at least one further scaffold/matrix attached region (S/MAR) (B2) and the consecutive order is A1-B1-C1-D1-B2 or A1-B2-C1-D1-B1, respectively. In case that the inventive nucleic acid molecule or expression vector, respectively comprises two genes of interest (A1 and A2) and one further S/MAR (B2), the preferred consecutive order is (A1-A2-B1-C1-D1-B2, or A1-A2-B2-C1-D1-B1, respectively. The at least one further scaffold/matrix attached region (S/MAR) (B2) may be the same or different from the at least one first scaffold/matrix attached region (S/MAR) (B1).

Preferred nucleic acid molecules or expression vectors, respectively, of the invention comprise at least one or two genes of interest. Thus, in a preferred embodiment, the inventive nucleic acid molecule or expression vector, respectively, comprises at least two genes of interest, a first gene of interest (A1) and a second gene of interest (A2) of said at least one or two genes of interest. Thus, with respect to the consecutive order, the first of the at least one gene of interest (A1), the second of the at least one gene of interest (A2), the first of the at least one scaffold/matrix attached region (S/MAR) (B1), the first of the at least one origin of replication (ORI) (C1), and the first of the at least one replication initiation factor (D1) are positioned on the inventive nucleic acid molecule or expression vector, respectively, in a consecutive order selected from (a) the consecutive order of A1-A2-B1-C1-D1; and (b) the consecutive order of A1-A2-C1-D1-B1. In one preferred embodiment, the consecutive order is A1-A2-B1-C1-D1, preferably, promA1pa-promA2pa-B1-C1-D1, more preferably promA1pa-promA2pa-B1-C1-paD1prom. In another preferred embodiment, the consecutive order is A1-A2-C1-D1-B1, preferably A1-A2-C1-paD1prom-B1, more preferably promA1pa-promA2pa-C1-paD1prom-B1. Preferably, the first gene of interest and the second gene of interest are selected from (a) the light chain of an antibody, and (b) the heavy chain of an antibody. Thus, in one specifically preferred aspect, the first gene of interest (A1) comprises the light chain of an antibody and the second gene of interest (A2) comprises the heavy chain of an antibody. Preferably, the light chain (A1) and the heavy chain (A2) are from the same antibody.

In another preferred embodiment, wherein the nucleic acid molecule or expression vector, respectively, of the invention comprises two genes of interest, the distance between the first S/MAR element and the polyadenylation signal sequence of the gene of interest is to be understood as the distance between the first S/MAR element (B1) and the polyadenylation signal sequence of the second gene of interest (A2). Thus, in a specific embodiment, the distance between the first S/MAR element and the 3' end of the second gene of interest, or alternatively the polyadenylation signal sequence, is less than 30,000 base pairs (bp), less than 20,000 bp, less than 10,000 base pairs (bp), more preferably less than 5000 bp, more preferably less than 2000 bp, more preferably less than 1000 bp, even more preferably less than bp, less than 100 bp, and most preferably less than 50 bp or even more preferably 6 bp or even zero base pairs. Preferably, the distance between the first S/MAR element and the polyadenylation signal sequence of the second gene of interest is less than 500 bp, more preferably less than 100 bp. Most preferably, the distance between the first S/MAR element and the polyadenylation signal sequence of the second gene of interest is less than 50 bp.

In a preferred embodiment, the nucleic acid molecule of the invention is an expression vector, preferably an episomally replicating expression vector. Preferably, the present invention provides an episomally replicating expression vector comprising at least one gene of interest (abbreviated as A1, A2, A3 . . . ), at least on S/MAR (abbreviated as B1, B2, B3 . . . ), at least one origin of replication (abbreviated as C1, C2, C3 . . . ), and at least one replication initiation factor (abbreviated as D1, D2, D3 . . . ). In a very preferred embodiment, the expression vector of the invention comprises (a) at least one, preferably two genes of interest (A1, A2), (b) at least one S/MAR (B 1), (c) a first and a second origin of replication (C1, C2), and (d) a first and second replication initiation factor (D1, D2), wherein the first replication initiation factor (D1) is capable of recognizing the first origin of replication (C1) and wherein the second replication initiation factor (D2) is capable of recognizing the second origin of replication (C2). Preferably, the first origin of replication is the EBV OriP, the first replication initiation factor is the EBNA1 gene, the second origin of replication is the SV40 ori, and the second replication initiation factor is SV40 large T-antigen.

In a further embodiment, the at least one gene of interest, the at least on S/MAR, the at least one origin of replication, and the at least one replication initiation factor are all present on a single nucleic acid molecule or expression vector, respectively. In another embodiment, the at least one gene of interest, the at least one S/MAR, and the at least one origin of replication (ORI) are present on a first nucleic acid molecule or expression vector, respectively, and the at least one replication initiation factor is present on a second nucleic acid molecule or expression vector, respectively. In a very preferred embodiment, the at least one replication initiation factor, preferably the second of the at least one replication initiation factor, is stably integrated into the genome of the host cell in which the episomally replicating expression vector is introduced.

In a further preferred embodiment, if the nucleic acid molecule or expression system, respectively, of the invention comprises a first and a second origin of replication, the second origin of replication either be present on the first nucleic acid molecule (in cis) or on another nucleic acid molecule (in trans). Preferably the second origin of replication is on the first nucleic acid molecule, that is on the same nucleic acid molecule as the at least one gene of interest, the at least one S/MAR, the first origin of replication and/or the first and/or second replication initiation factor. Preferably, the second origin of replication is SV40 ori.

In a further preferred embodiment, the nucleic acid molecule or expression system, respectively, of the invention further comprises a second replication initiation factor, typically and preferably a second replication initiation factor recognizing the second origin of replication. The second replication initiation factor may be the same or different from the first replication initiation factor. The second replication initiation factor may either be present on the first nucleic acid molecule (in cis) or on another nucleic acid molecule (in trans). In a preferred embodiment, the second replication initiation factor is stably integrated into the genome of the host cell in which the expression system is introduced. Preferably, the second replication initiation factor is SV40 large T-antigen.

The episomally replicating expression vector of the invention provides certain advantages over classical expression systems. Some DNA viruses, such as Adeno-, Papilloma-, Polyoma-, Hepadna-, and Herpesviruses, typically do not integrate into the host genome, but replicate episomally (extrachromosomally) in the nucleus of a host cells such as in a mammalian host cell. This process involves both virus trans-acting factors and the host cell replication machinery.

The episomally replicating expression vector of the invention is semi-stable and retains in the transfected cell typically at least 5 generations, more preferably over at least 8 generations, more preferably over at least 10 generations, more preferably over at least 12 generations, even more preferably over at least 15 generation, over at least 20 generations or even 30 generations.

The nucleic acid molecule or expression system, respectively, of the present invention comprise, inter alia, at least one gene of interest. A wide variety of genes of interest can be expressed by the nucleic acid molecules and expression systems of the invention. These genes of interest include, but are not limited to, sequences encoding toxins, enzymes, prodrug converting enzymes, antigens which stimulate immune responses, single chain antibodies, polypeptides which stimulate or inhibit immune responses, tumor necrosis factors, light and/or heavy chain of an antibody, lymphokines (e.g. beta-interferon), cytokines, and various proteins with therapeutic applications (e.g., growth hormones and regulatory factors). Hematopoiesis is regulated by lymphokines and cytokines which stimulate the proliferation and/or differentiation of various hemopoietic cells. Representative examples of cytokines and lymphokines include interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-16 (IL-16), interleukin-17 (IL-17), granulocyte colony stimulating factor (G-CSF), granulocyte-macrophage colony stimulating factor (GM-CSF), macrophage colony stimulating factor (M-CSF), and interferons.

In a preferred embodiment, the nucleic acid molecule or expression system, respectively, of the invention comprises two genes of interest, preferably a first gene of interest and a second gene of interest for example for the expression of antibodies. Alternatively, the nucleic acid molecule or expression vector, respectively, may comprise several genes of interest like for example for the expression of multi subunit proteins such as ion channels. The individual polypeptides will be expressed by different promoters or by one promoter in the presence of internal ribosomal entry sites. The different promoters can be of the same or different origins. In a preferred embodiment, the nucleic acid molecule or expression vector, respectively, comprises a first gene of interest encoding the light chain of an antibody, and a second gene of interest encoding the heavy chain of an antibody. Preferably, the light chain and heavy chain are of the same antibody. Thus, in certain embodiments, the gene of interest of the invention may encode an antibody. The complete antibody may be expressed from two different promoters, for example light chain from a first CMV promoter and the heavy chain from a second CMV promoter. Additionally single chain antibodies may be expressed.

In certain embodiments, the gene of interest of the invention may encode secreted enzymes (e.g., secreted alkaline phosphatase), cytoplasmic enzymes (e.g., green fluorescent protein), or any number of other proteins with therapeutic applications (e.g., human insulin, human coagulation Factor VIII).

The nucleic acid molecules and expression systems of the invention can also be used to express virtually any polypeptide, including ones which have not as yet been identified but are encoded by nucleotide sequences contained in, for example, cDNA libraries or host cell chromosomes. Examples of such polypeptides include secreted proteins and proteins from various cellular compartments.

The gene of interest may alternatively or additionally comprise a nucleotide sequence encoding an untranslated RNA molecule or complement thereof. Exemplary untranslated RNA molecules include, e.g., antisense sequences, RNase P targeted sequences which induce gene downregulation, and ribozymes. For example, RNA molecules directly produced by transcription of a DNA sequence of the invention may encode RNA sequences which are neither translated nor present in an antisense orientation. Examples of such untranslated RNA molecules include tRNA molecules, rRNA molecules, and ribozymes. A considerable number of ribozyme sequences with defined catalytic activities are known in the art (see, e.g., Brown, J., *Nucleic Acids Res.* 26:351-352 (1998); Xie, Y. et al., *Proc. Natl. Acad. Sci. USA* 94:13777-13781 (1997); Lavrovsky. Y et al., *Biochem. Mol. Med.* 62:11-22 (1997); Chapman, K. and Szostak, J., *Chem. Biol.* 2:325-333 (1995)). Further, ribozymes have been used to "knockout" the expression of a specific gene in eukaryotic cells as part of a ribozyme-mediated, message deletion strategy (Xie, Y. et al., *Proc. Natl. Acad. Sci. USA* 94:13777-13781 (1997)). Additionally, alphaviral replicons have been used to express a functional ribozyme in mammalian cells (Smith S. et al., *J. Virol.* 71:9713-9721 (1997)). The expression of such ribozymes, and other untranslated RNA molecules, is thus within the scope of the present invention.

Nucleotide sequences may be added to the nucleic acid molecules and vectors of the invention which result in the production of a fusion protein. For example, such sequences can encode amino acids sequences which are fused to a protein encoded by a gene of interest and confer one or more functional characteristics upon the expression product. These amino acid sequences include sequences which will target the gene product for export from the cell (e.g., a secretory sequence) or to a subcellular compartment (e.g., the nucleus). Such amino acid sequences further include sequences which facilitate purification (e.g., a six His "tag"). Depending on the amino acid sequence and the function imparted by the fused sequence, the added amino acid sequences may or may not be cleaved from the translation product.

Fusion proteins also include proteins which have domains or regions derived from various different proteins. Examples of such a fusion protein are those containing domain II of *Pseudomonas* exotoxin, a domain or amino acid sequence which has binding affinity for a cell surface receptor associated with a particular cell type, and another amino acid sequence with a preselected biological activity. Domain II of *Pseudomonas* exotoxin will translocate across cell membranes. Using this system, fusion proteins can be designed which will bind to specific cells types, will translocate across the cytoplasmic membranes of these cells, and will catalyze predetermined intracellular biological reactions. A system of this type is described in Pastan et al., U.S. Pat. No. 5,705,163. Methods for identifying amino acid sequences, which bind to specific cell types are described in Wu, A., *Nature Biotech.* 14:429-431 (1996).

The at least one origin of replication, preferably the first and/or second and/or third origin of replication, that is included in, or used with, the compositions and methods of the invention is derived from a prokaryotic organism, a eukaryotic organism (e.g., a yeast, insect or mammal, preferably hamster, e.g. origins as described by Amy L. et al, (2004), MCB, 24, 4138-4150), and/or a virus. Preferably, the at least one origin of replication is derived from a virus that allows for episomal replication. Preferably the origin of replication is derived from a DNA virus, more preferably from a DNA virus that allows for episomal replication. Most preferably, the at least one origin of replication is derived from a DNA virus selected from the group consisting of Herpesviridae (e.g. Epstein-Barr virus, Herpes simplex virus, *Herpesvirus Saimiri*, Murine *Gammaherpesvirus* 68, Human *Cytomegalovirus*, Mouse *Cytomegalovirus, Pseudorabiesvirus*), Papovaviridae (e.g. Simian Virus 40, Polyoma virus, human BK virus, Bovine Papiloma virus), Parvoviridae (Adeno-associated virus), Adenoviridae, and Hepadnaviridae. In a particularly preferred embodiment, the at least one origin of replication, preferably the first of the at least one origin of replication is from Epstein-Barr virus (EBV), such as, e.g., oriP, or is assembled from EBV sequences, and comprises EBNA-1 binding sites; examples for such EBV-type of functional origins are described in Aiyar et al., (1998) THE EMBO Journal, 17, pp. 6394-6403. In another preferred embodiment, the at least one origin of replication, preferably the first of the at least one origin of replication is derived from Murine *Gammaherpesvirus* 68 (MHV68). Further examples for suitable origins of replication (ORI) that may be included in, or used with, the compositions and methods of the invention are known in the art and described for example without limitation in Bode J. et al. (2001, Gene Ther Mol Biol, v6, 33-46), Yates, J. L. et al. (2000, J Virol. 74(10):4512-22), Kanda T. et al. (2001, Mol Cell Biol., 21(10):3576-88), Kusano S. et al. (2001, Intervirology. 44(5):283-90), or Koons M. et al. (2001, J Virol. 75(22):10582-92). It may of course be possible to generate, by the means of genetic engineering mentioned in the preceding sections in this regard, non-natural or functional variants of such origins of replication. Again, such functional variants are encompassed in the meaning of origin of replication according to the present application.

In a particularly preferred nucleic acid molecule or expression system of the invention, the at least one origin of replication, preferably the first of the at least one origin of replication, is an EBV origin of replication (OriP). The EBV origin of replication (OriP) is composed of 2 main elements and multiple cis-acting elements that facilitate DNA synthesis by the cell and a viral maintenance element. The first of the two main elements contains a family of repeats (FR), which serves the function of a maintenance element. The second element contained in OriP contains a so called dyad symmetry (DS) and its function is to serve as an origin recognition element (ORE) which is recognised by the origin recognition complex (ORC). In addition it serves as a DNA unwinding element (DUE). Altogether OriP contains several, typically 24 binding sites for the replication initiation and maintenance factor EBNA1. These sites are located on one hand in the family of repeats and on the other hand in the dyad symmetry. Those two functional elements are spaced by several base pairs, typically 1000 bp. The relative orientation of OriP, and in particular of DS and FR, can be altered without affecting OriP function. Moreover, the OriP function is also barely affected by yet another locus, BamHI-Q, with two additional low-affinity EBNA1 binding sites (Rawlins et al., (1985), Cell 42, 859-868). Therefore, the orientation of OriP, and in particular of DS and FR, relative to the other elements positioned on the inventive nucleic acid molecules and expression vectors, respectively, can be altered without affecting OriP function. In a preferred embodiment of the invention, wherein the origin of replication is an EBV origin of replication (OriP), and wherein the OriP comprises a family of repeats (FR) and a dyad symmetry (DS), the consecutive order is such that the DS element is between the gene of interest and the FR element, whereas the FR element is between the DS element and the replication initiation factor. In a further preferred embodiment, the at least one origin of replication, typically and preferably the second origin of replication is SV40 ori. In a further embodiment, the first origin of replication is OriP, the second origin of replication is SV40 ori, and the third origin of replication is MHV68 ori.

The nucleic acid molecules and expression systems of the invention also comprise a replication initiation factor. The replication initiation factor, and herein preferably the first replication factor, that is included in, or used with, the compositions and methods of the invention is, in certain embodiments, capable of recognizing the first origin of replication that is included within the nucleic acid molecule or expression system. Moreover, the replication initiation factor is capable of operating as a plasmid maintenance factor. As used herein, the term "plasmid maintenance factor" is intended to mean a factor, which supports the distribution of the episomes to the daughter cells upon cell division.

The replication initiation factor, and herein preferably the first and/or second and/or third of the at least one replication initiation factor of the invention may be a protein or a DNA sequence encoding the open reading frame of such a protein or a coding sequence which can be separated by introns encoding for such a protein. Any functional variants of the replication initiation factor may also be used for the compositions and methods of the present invention. Such variants can be generated e.g. by substitutions, deletions, insertions or truncations of the amino acids of the replication initiation factor and its encoding DNA sequence, respectively. Methods for such are well known in the art and usually comprise specific site directed mutagenesis or generation of diversity by random mutagensis of which is then followed by selecting desired variants by means of functional assays. Routine methods employed for mutagenesis may be e.g. exposure to alkylating agents or UV irradiation, error-prone PCR or related gene shuffling PCR techniques and are usually performed in microorganisms (Miller, J., Experiments in Molecular Genetics, Cold Spring Harbor Laboratory 1972; Ling et al., 1997, Approaches to DNA Mutagenesis, Analytical biochemistry 254, 15 7-178; Cadwell et al., 1992, Randomization of genes by PCR mutagenesis in:PCR Methods, Cold Spring Harbor Laboratory Press 1992; Moore et al., 1997, Strategies for the in vitro evolution of protein function, J. Mol. Biol. 272, 336347).

Preferred functional variants of the at least one replication initiation factor of the present invention are those displaying at least 50%, preferably at least 80%, more preferably at least 100%, even more preferably at least 150%, and again more preferably at least 200%, of the replication activity or the episome maintenance activity, preferably of the replication activity and the episome maintenance activity, as compared to the wildtype protein in a specific cell line.

Examples of such functional variants and methods how to test such functional variants are known in the art. For example, increased replication activity has been observed in EBNA1 mutants with a deletion in the ubiquitin-specific protease (USP-7) binding region (amino-acids 395-450) (M. Holowaty et al., 2003, *JBC*, 29987-29994). Another example for a functional variant of the replication initiation factor of the invention has been described by Hung S. C. et al. (2000, *PNAS*, v98, 4, 1865-1870) where the HMG-1 (high mobility group-1) amino-acids 1-90 could substitute for EBNA-1 aminoacids 1-378 in mediating more efficient accumulation of replicated oriP plasmids, association with mitotic chromosomes, nuclear retention and episome maintenance. A further example for an improved functional variant of the replication initiation factor EBNA1, where amino acids 61-83 have been deleted, has been described by Wu H. et al (2002, *JV*, 2480-2490).

The replication initiation factor of the invention is derived from a prokaryotic organism, an eukaryotic organism (e.g., yeasts, insects, and/or mammals) or a virus. Preferably, the replication initiation factor is derived from a virus that allows for replication. Preferably, the replication initiation factor is derived from a DNA viruses, preferably a DNA virus selected from the group of Herpesviridae (e.g. Epstein-Barr virus, Herpes simplex virus, *Herpesvirus Saimiri*, Murine *Gammaherpesvirus 68*, Human *Cytomegalovirus*, Mouse *Cytomegalovirus*, *Pseudorabiesvirus*), Papovaviridae (e.g. Simian Virus 40, Polyoma virus, human BK virus, Bovine Papilloma virus), Parvoviridae (Adeno-associated virus), Adenoviridae, and Hepadnaviridae. Preferably, the replication initiation factor that is used with the present invention is a replication initiation factor from a DNA virus such as, e.g., a *Herpesvirus, Polyomavirus* or a *Papillomavirus* which are episomally replicating viruses. More preferably, the replication initiation factor that is used with the invention is capable of operating as an episomal plasmid maintenance factor in the presence of the origin of replication. Most preferably, the replication initiation factor is a replication initiation factor from a DNA virus selected from the group consisting of Herpesviridae (e.g. EBNA-1 for Epstein-Barr virus (EBV)), Papovaviridae (e.g. the E1/E2 replication initiation factor for *Papillomavirus* such as BPV or HPV or e.g. large T-antigen replication initiation factor for Polyoviridae such as SV40), Adenoviridae, and Hepadnaviridae.

In a particularly preferred embodiment, the first of the at least one replication initiation factor of the invention is from Epstein-Barr virus (EBV), such as, e.g., the EBNA-1 protein, most preferably it is EBNA-1 protein or a functional variant thereof. The term 'functional variants' is used in its above meaning here. In the case of EBNA-1, this effect of enhanced episomal plasmid maintenance is achieved by the binding of the protein to the episome and, at the same time, to the chromosome, thereby leading to proper distribution of the episomes to the daughter cells. In a further particularly preferred embodiment, the second replication initiation factor of the invention is from Polyomaviridae, such as the SV40 large T-antigen replication initiation factor. In yet a further embodiment, the first of the at least one replication initiation factor is derived from MHV68, such as e.g. the LANA1 protein, and the second replication initiation factor is the SV40 large T-antigen. In another embodiment, the first replication initiation factor is EBNA-1, the second replication initiation factor is SV40 large T-antigen, and the third replication initiation factor is LANA1.

The at least one replication initiation factor of the present invention, typically and preferably the first, second or more replication initiation factor, may comprise a promoter or a promoter and an enhancer, preferably a promoter only, the coding sequence of the replication initiation factor which can be either spaced by introns or which is a cDNA encoding the open reading frame, and a polyadenylation signal sequence. The promoter may be any sequence which enables transcription initiation from a downstream DNA sequence in mammalian cells and may be of viral or non-viral origin. In one preferred embodiment, the promoter is natural EBV-derived promoter driving expression of the EBNA-1 coding sequence in the EBV genome. In another preferred embodiment, the promoter of the at least one replication initiation factor and the at least one replication initiation factor are derived from different viruses.

Assays to measure replication properties conferred by a sequence are well-known in the art and can be found e.g. in Aiyar et al., (1998) THE EMBO Journal, 17, pp. 6394-6403. Origins of replication share common features. First an initiator protein such as dnaA in *E. coli*, large T in SV40 and EBNA1 in Epstein-Barr virus is responsible for the formation of a large complex containing several initiator protein molecules. Additionally AT rich sequences are found which undergo strand separation (Bode J. et al. (2001, Gene Ther Mol Biol, v6, 33-46)).

The at least one replication initiation factor (e.g., a nucleotide sequence that encodes the at least one replication initiation factor) and the at least one origin of replication that are included in, or used with, the nucleic acid molecules, expresseion vectors and methods of the invention may, in certain embodiments, be derived from the same organism or the same virus. Alternatively, the at least one origin of replication and the at least one replication initiation factor may be derived from different organisms or viruses.

Thus, in a preferred embodiment of the present invention, the at least one origin of replication and the at least one replication initiation factor are derived from a DNA virus. Even more preferably, the at least one, preferably the first origin of replication may be derived from a herpes virus and the replication initiation factor may be the Epstein-Barr virus nuclear antigen 1 (EBNA1). However, replication initiation factors may also derive from other viruses or be cellular factors, which are capable of recognizing or recognize viral origins of replication.

Thus, in a preferred embodiment, the present invention provides a hybrid vector and vector system combining the advantages of EBV episomal replication with the advantages of the S/MAR element, wherein the replication takes place entirely in the cytoplasm.

In a specific embodiment, the invention includes the combination of a *Herpesvirus* mini-replicon unit, i.e. the cis-acting replication origin OriP (Origin of replication P) and the cis- or trans-acting gene product—EBNA-1 (Epstein-Barr virus nuclear antigen 1, a replication triggering factor) with the S/MAR element. Due to the presence of OriP and EBNA-1 the introduced novel vector is maintained episomally (extrachromosomally) in the form of one or more DNA copies in the cell nuclei.

In a further embodiment, the nucleic acid molecule or expression vector, respectively, of the invention comprises more than one origin of replication (ORI). The at least one further origin of replication that may be included in addition to the first origin of replication (ORI) may be the same or different from the first origin of replication (ORI). In a specific embodiment, the first origin of replication is the EBV origin of replication (OriP) and the at least one further origin of replication is from another DNA virus than EBV, e.g. from SV40 or BPV, preferably the SV40 Ori. In another specific embodiment, both the first origin of replication and the at least one further origin of replication are EBV origins of replication (OriP).

In a particularly preferred embodiment of the vector, one or more "origin of replication" will be contained for propagation in eukaryotes and one or more for propagation in prokaryotes, preferably at least one for propagation in the eukaryote and at least one for propagation in the prokaryote. The advantage of this embodiment is that, on the one hand, the vector can easily be replicated in prokaryotes and, on the other hand, the same vector can be stably maintained in eukaryotes. Thus, nucleic acid molecules and expression systems according to the invention in which the origin of replication is used for propagation in prokaryotes, in this case preferably the pUC-ORI, are also part of the invention. A vector equipped in this way has the advantage that it can be utilized for the replication of the vector in prokaryotes and thus can be replicated comparatively simply in high yields. In a preferred embodiment, the recombinant host cell of the invention is a eukaryotic or prokaryotic cell selected from the group of cells consisting of a bacterial, yeast, insect, amphibian, fish, and mammalian cell and the inventive nucleic acid molecule or expression vector, respectively, comprises at least two origins of replication, wherein at least one of the at least two origins of replication is capable of propagating in a eukaryote and wherein at least one of the at least two origins of replication is capable of propagating in a prokaryote.

In an exemplary embodiment of the invention, nucleic acid molecules are provided that are constructed by introducing defined Epstein-Barr virus (EBV) sequences into vectors. The resulting exemplary nucleic acid molecules of the invention are capable of replicating as non-integrated autonomous episomal molecules in the host cells.

In a preferred embodiment, the defined sequences, which may be introduced into the vectors comprise, e.g., at least one gene of interest, at least one scaffold/matrix attached region (SMAR), either one or two elements of Epstein-Barr virus, (OriP alone or together with EBNA-1 gene) which permit plasmid maintenance. The at least one origin of replication OriP is a cis-acting sequence and needs to be inserted into the plasmid vector sequence. Plasmids containing this origin of replication are able to be maintained in cells expressing the replication initiation factor which recognizes the origin of replication; one of these factors is EBNA-1 or SV40 large T-antigen. EBNA-1 gene function or SV40 large T-antigen function can be provided in cis by introducing the sequence into the same plasmid as the OriP or the SV40 ori or can be provided in trans by co-transfection with a second replicating or non-replicating plasmid as well as by providing it from stably transduced cell lines expressing EBNA-1 gene and/or the SV40 large T-antigen from integrated copy. Furthermore, in certain embodiments, more than one copy of the sequence expressing the replication initiation factor, e.g. EBNA-1 or SV40 large T-antigen, is provided. For example, EBNA-1 gene function or SV40 large T-antigen function may be provided on one or more plasmids, wherein none, some or all of those plasmids may additionally comprise the origin of replication, and which plasmids are used for transfecting cell lines, preferably cell lines that have the sequence of EBNA-1 or SV40 large T-antigen stably integrated within its genome. The presence of both OriP and EBNA1 sequences in the same plasmid renders replication less dependent on the host cell type. (Reisman, D. et al., *Mol. Cell Biol.* 5: 1822-1832 (1985); Yates, J. L. et al., *Nature* 313:812-815 (1985); U.S. Pat. No. 4,686,186).

Cell lines which have stably integrated replication initiation factor within the genome have the advantage of stable long-term expression of the replication initiation factor and durable support of replication and maintenance of the origin of replication containing plasmids. Commercially available cell lines expressing EBNA-1 are (ATCC: 293HEK-EBNA1 and CV1-EBNA1). Specific cell lines overexpressing the at least one replication initiation factor, preferably the EBNA1 protein or the SV40 large T-antigen, can be generated by transfection and selection of stable cell clones.

In a further general aspect, the present invention provides an expression system comprising (a) at least one gene of interest, (b) at least one scaffold/matrix attached region (S/MAR); (c) at least one origin of replication (ORI); and (d) at least one replication initiation factor capable of recognizing said origin of replication. Thus, the at least one replication initiation factor recognizes the at least one origin of replication leading to replication of the DNA element comprising the at least one origin of replication. In a preferred embodiment, the expression system comprises one or more inventive nucleic acid molecules, preferably one or more inventive episomally replicating expression vectors, wherein said one or more nucleic acid molecules or expression vectors, respectively, comprise (a) at least one gene of interest, (b) at least one scaffold/matrix attached region (S/MAR); (c) at least one origin of replication (ORI); and (d) at least one replication initiation factor.

The invention further provides single- and multiple-vector expression systems for producing a polypeptide or untranslated RNA molecule. In a single-vector system, the at least one gene of interest, the at least one scaffold/matrix attached region (S/MAR), the at least one origin of replication (ORI), and the at least one replication initiation factor are all present on a single nucleic acid molecule. In a multiple-vector system, the first scaffold/matrix attached region (S/MAR), the first origin of replication (ORI), and the first replication initiation factor are present on one or more separate nucleic acid molecules. These multiple-vector systems thus may comprise two or more nucleic acid molecules. For example, the replication initiation factor and the gene of interest can each be encoded by different nucleic acid molecules. In certain embodiments, the S/MAR element and origin of replication (ORI)s will be on a single nucleic acid molecule while the replication initiation factor and the gene of interest are on a different nucleic acid molecule. In another preferred embodiment, the at least one gene of interest, the at least one S/MAR, and the at least one origin of replication (ORI) are present on a first nucleic acid molecule or expression vector, respectively, and the at least one replication initiation factor is present on a second nucleic acid molecule or expression vector, respectively. In such a multiple vector system, at least one, preferably some or more preferably all vectors contain an origin of replication. In addition, in such a multiple vector system, the expression vector or plasmid, respectively, containing the S/MAR element contains at least one origin of replication. Therefore, in preferred embodiments of the invention, the replication initiation factor and the origin of replication recognizing the replication initiation factor may be on the same nucleic acid molecule and expression vector, respectively, as it is the replication initiation factor or on a separate nucleic acid molecule and expression vector, respectively.

In a further aspect of the invention, the nucleic acid molecule or expression vector, respectively, of the invention further comprises one or more promoter or activator sequences and/or one or more effectors. Promoters are understood as meaning nucleic acid sequences which usually lie 5' from the sequence to be read and regulate the transcription rate of a gene such as, for example, the at least one gene of interest, the at least one replication initiation factor and the selection marker. "Enhancers" can be counted among the activators and differ from other regulation elements in that they usually lie at a greater distance from the promoter 5' or 3' and can increase the transcription activity in a position-independent manner, e.g. from human *cytomegalovirus* (EP 0 173 177), CMV immediate-early polypeptide (Pos. 216-809/Genbank Accession No.: K03104). Thus, the promoter may be any sequence which enables transcription initiation from a downstream DNA sequence in host cells, typically and preferably in mammalian cells. The promoter can be of viral or non-viral origin. Promoters are usually selected from the group of promoters consisting of constitutive promoters, cell cycle-specific promoters, tissue-specific promoters, metabolically regulated promoters, and inducible promoters. While any functional promoter can be used to drive the transcription of mRNA from the nucleic acid molecule or expression vector, respectively, of the invention, the promoter is preferably a constitutive RNA polymerase II promoter (e.g., EF1α, Rous Sarcoma Virus (RSV), *cytomegalovirus* (CMV) (human or mouse CMV), simian virus 40 (SV40) early or late promoter, myeloproliferative sarcoma virus (MPSV), glucocorticoid, metallothionein, Herpes simplex virus thymidine kinase (HSVTK), human immune deficiency (HIV), mouse mammary tumor virus (MMTV), human *polyomavirus* BK (BKV), the elongation factor alpha promoter and the like or Moloney murine leukemia virus (MuLV) promoter) or a constitutive, engineered hybrid promoter such as, preferably, SRα which is a fusion of SV40 early promoter to RU5' region of a human retrovirus such as HTLV-1 LTR (Takebe et al, Mol. Cell Biol. 8 (1988), 466-472). Additional promoters suitable for use in the practice of the present invention are known in the art (see, e.g., Lee, A. et al., *Mol. Cells.* 7:495-501 (1997)). Typically and preferably, the promoter of the replication initiation factor of the invention is of viral or non-viral origin. Preferably, the promoter of the replication initiation factor is a constitutively active promoter thus allowing of permanent stable expression of the replication initiation factor which in turn supports stable episomal maintenance of vector. In a further preferred embodiment, the promoter of the at least one, and preferably the first of said at least one, replication initiation factor is a constitutive promoter, and preferably a CMV, SRα or an EF1α promoter, even more preferably an EF1α promoter. Typically and preferably, the promoter of the at least gene of interest of the invention is of viral or non-viral origin. Preferably, the promoter of the at least one gene of interest is a constitutively active promoter thus allowing of permanent stable expression of the at least one gene of interest. In a further preferred embodiment, the promoter of the at least one gene of interest is a constitutive promoter, and preferably a CMV or an EF1α promoter, even more preferably a CMV promoter.

The promoter may be combined with an enhancer element. The combination of promoter and enhancer element(s) can be selected by one skilled in the art to improve expression levels. Different enhancer elements can be used to produce a desired level of transgene transcription and/or expression in a wide variety of tissue and cell types. For example, the human CMV immediate early promoter-enhancer element can be used to produce high level transgene transcription and expression in many different tissues in vivo.

In another aspect of the invention, the nucleic acid molecule or expression vector, respectively, further comprises an activator sequence selected from the group consisting of constitutive activators, cell cycle-specific activators, tissue-specific activators, metabolically regulated activators, and/or inducible activators or activator sequences. On the whole, these have the advantage, depending on choice, of being appropriate to the cell situation, so that particular metabolic conditions or therapeutic needs of a cell can be taken into account or that the replication or expression can be controlled by external factors.

Preferred effectors code for certain substances, selected from proteins, peptides, ribozymes or antisense RNAs, or are antisense DNAs. Peptides are understood here as meaning a part of a protein, or an amino acid sequence, either of natural or synthetic type. The function of these effectors is extremely diverse and can be tailored to the particular therapeutic needs. In the widely diversified literature, many examples of this are available, coding sequences being known, in particular for therapeutic proteins. Without restricting the application possibilities of the vector according to the invention thereto, or this listing being intended to be complete, a few examples are mentioned here in which proteins, or genes coding for these proteins, can be used therapeutically in this connection: nitrogen monoxide synthase (see, for example, WO 95/27020), insulin (see, for example, EP-B 100 01 929), erythropoietin (see, for example, EP-B1-0 148 605), light and/or heavy chain of an antibody, or blood clotting factors, such as, for example, factor VII, interferons, cytokines, hormones, growth factors etc. The choice of the suitable effectors employed in the vector remains left to the knowledge of the person skilled in the art.

The nucleic acid molecules or expression vectors, respectively, of the invention may further comprise a selection marker. The selection marker may facilitate the cloning and amplification of the vector sequences in prokaryotic and eukaryotic organisms. In certain embodiments, the selection marker will confer resistance to a compound or class of compounds, such as an antibiotic. An exemplary selection marker that can be used with the nucleic acid molecules and expression systems of the present invention is one that confers resistance to puromycin. Alternatively, selection markers may be used that confer resistance to hygromycin, gpt, neomycin, zeocin, ouabain, blasticidin, kanamycin, geneticin, gentamicin, ampicillin, tetracycline, streptomycin, spectinomycin, nalidixic acid, rifampicin, chloramphenicol, zeocin or bleomycin, or markers such as DHRF, hisD, trpB, or glutamine synthetase.

In an alternative embodiment, the gene of interest of the inventive nucleic acid molecules and expression systems further comprise an inducible component, preferably a temperature sensitive component, more preferably a non-cytopathic temperature sensitive component. Such inducible components are well known in the art. One example is the pCytTS system as disclosed in WO 99/504332.

The invention may include as a further subject a composition which contains at least one of the nucleic acid molecule or expression vector according to the invention and/or a cell which contains such a vector, and suitable additives and/or auxiliaries.

The suitable additives and auxiliaries are to be understood as meaning, in particular, adjuvants, stabilizers and/or transfection-facilitating substances. Also covered are transfection systems including transfection vectors, which are combined or associated with the vector according to the invention and its penetration into cells, which facilitate or even allow transfection or alternatively transformation. Auxiliaries are in particular to be understood as also meaning general protease inhibitors, such as PMSF, and nuclease inhibitors, such as EDTA.

The nucleic acid molecules and expression systems of the invention may, in certain embodiments, further comprise genetic elements which confer additional functional characteristics such as selection markers.

Markers for the selection of prokaryotic and eukaryotic cells containing vectors the present invention are well known in the art and include puromycin, tetracycline, ampicillin, neomycin, hygromycin, gpt, zeocin, ouabain, blasticidin, bleomycin, and kanamycin resistance. Alternatively, selection markers such as DHRF, hisD, trpB, or glutamine synthetase may be used. Nucleotide sequences which result in high copy number amplification are also known in the art.

In a further aspect of the invention a composition is provided comprising either the nucleic acid molecule or the recombinant host cell of the invention, and a transfection system selected from the group consisting of those which comprise a lipid, a polymer, a peptide, or a porphyrin.

In further embodiments of the invention, recombinant host cells and in vitro cell cultures comprising recombinant host cells are provided. The recombinant host cells of the invention comprise (a) at least one, preferably one or two, genes of interest; (b) at least one scaffold/matrix attached region (S/MAR); (c) at least one, preferably one or two, origins of replication (ORI); and (d) at least one, preferably one or two, replication initiation factors capable of recognizing said origin of replications. In a preferred embodiment, the at least one gene of interest, the at least on S/MAR, the at least one origin of replication, and the at least one replication initiation factor are all present on a single nucleic acid molecule or expression vector, respectively, in the recombinant host cell. In another preferred embodiment, the at least one gene of interest, the at least one S/MAR, and the at least one origin of replication are present on a first nucleic acid molecule or expression vector, respectively, and the at least one replication initiation factor is present on a second nucleic acid molecule or expression vector, respectively, in the recombinant host cell. In yet another embodiment, the at least one gene of interest, the at least one S/MAR, and the at least one origin of replication are present on a single nucleic acid molecule or expression vector, respectively, and the at least one replication initiation factor is stably integrated into the genome of the recombinant host cell.

In yet another preferred embodiment, the at least one gene of interest, the at least one S/MAR, and the at least one first and/or second origin of replications are present on a first nucleic acid molecule or expression vector, respectively, and the at least one first and/or second replication initiation factors are present on a second nucleic acid molecule or expression vector, respectively, in the recombinant host cell. In yet another embodiment, the at least one gene of interest, the at least one S/MAR, and the at least one first and/or second origin of replications are present on a single nucleic acid molecule or expression vector, respectively, and the at least one first and/or second replication initiation factors are stably integrated into the genome of the recombinant host cell.

In a very preferred embodiment, the recombinant host cell of the invention comprises (a) at least one, preferably two genes of interest (A1, A2), (b) at least one S/MAR (B1), (c) a first and a second origin of replication (C1, C2), and (d) a first and second replication initiation factor (D1, D2), wherein the first replication initiation factor (D1) is capable of recognizing the first origin of replication (C1) and wherein the second replication initiation factor (D2) is capable of recognizing the second origin of replication (C2). Preferably, the first origin of replication is the EBV OriP, the first replication initiation factor is the EBNA1 gene, the second origin of replication is the SV40 ori, and the second replication initiation factor is SV40 large T-antigen. Preferably the at least one gene of interest, the at least one S/MAR, the first and second origin of replication, and the first replication initiation factor are present on a first nucleic acid molecule, and the second replication initiation factor, preferably the SV40 large T-antigen is stably integrated into the genome of the at least one recombinant host cell.

In a preferred embodiment, the recombinant host cell is a eukaryotic or prokaryotic cell and said nucleic acid molecule or expression vector, respectively, further contains one or more ORIs for propagation in a eukaryote and for propagation in a prokaryote.

The invention also provides methods for making recombinant host cells comprising introducing nucleic acid molecules or expression vector, respectively, of the invention into host cells. Further provided are recombinant host cells produced by the introduction of nucleic acid molecules or expression vector, respectively, of the invention. In one embodiment, one, some or all of these recombinant host cells contain one or more nucleic acid molecules or expression vector, respectively, that comprise at least one gene of interest, at least one S/MAR, at least one origin of replication (ORI), and at least one replication initiation factor. The at least one replication initiation factor, typically and preferably the first and/or second replication initiation factor, in certain embodiments, may be stably integrated into the genome of the one, some or all host cells.

Thus, the invention includes methods of making recombinant host cells and recombinant host cells produced using the methods of the invention. For example, the methods of the invention comprise introducing one or more nucleic acid molecules or expression systems described herein into a host cell Thus, numerous host cells can be used in the practice of the invention. Representative host cells that may be used with the invention include, but are not limited to, bacterial cells, yeast cells, plant cells and animal cells. Preferred bacterial host cells include *Escherichia* spp. cells (particularly *E. Coli* cells and most particularly *E. coli* strains DH10B, Stb12, DH5, DB3, DB3.1, DB4 and DB5), *Bacillus* spp. cells (particularly *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells). Preferred animal host cells include insect cells (most particularly *Drosophila melanogaster* cells, *Spodoptera frugiperda* Sf9 and Sf21 cells and Trichoplusa High-Five cells), nematode cells (particularly *C. elegans* cells), avian cells, amphibian cells (particularly *Xenopus laevis* cells), reptilian cells, and mammalian cells (most particularly human, simian, canine, rodent, bovine, or sheep cells, e.g. NIH3T3, CHO (Chinese hamster ovary cell), COS, VERO, BHK, HEK, and other rodent or human cells). Preferred yeast host cells include *Saccharomyces cerevisiae* cells and *Pichia pastoris* cells. In another embodiment, BHK, COS, Vero, HeLa and CHO cells are further preferred since they are particularly suitable for the production of heterologous polypeptides because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 47:476 (1995); Lee K. et al. *Biotech. Bioeng.* 50:336 (1996)) to grow in serum-free medium, as well as in suspension.

In a further preferred embodiment of the present invention, the recombinant host cell is an animal cell, preferably a mammalian cell. In another preferred embodiment, the mammalian cell expresses the genomically integrated replication initiation factor. Preferred replication initiation factors integrated into the genome of the host cell include without limitation the EBNA1 protein and/or the SV40 large T-antigen.

In one particularly preferred embodiment of the invention, the recombinant host cell is a rodent cell, more preferably a hamster cell, most preferably a CHO or a CHO derived cell. CHO derived cells can be e.g. cells obtained from originating CHO cell lines by genetic engineering, cell fusion, extended passaging and medium-adaptation process and the like. Preferred CHO cells and CHO derived cells suitable for the production of polypeptides include without limitation CHO-K1 (e.g. ACC-110 deposited at DSMZ, German depository acknowledged under Budapest Treaty), CHO-DUKX, CHO-DXB11, CHO-dhfr (e.g. ACC-126 deposited at DSMZ, German depository acknowledged under Budapest Treaty), CHO-F3B4, CHO-GD3, CHO-SSF3, B13-24, 35.6, 5/9m alpha 3-18 (e.g. CRL-10154 deposited at ATCC, U.S.A. depository acknowledged under Budapest Treaty), 6E6 (e.g. CRL-11398 deposited at ATCC, U.S.A. depository acknowledged under Budapest Treaty), AA8 cells, and CHO derived cells expressing the genomically integrated EBNA1 protein (CHO-EBNA cells) and/or SV40 large T-antigen (CHO-T cells, CHO-EBNA-T). Preferred host cells of the invention are CHO derived cells expressing the genomically integrated SV40 large T-antigen (CHO-T cells), CHO derived cells expressing the genomically integrated EBNA1 protein (CHO-EBNA cells) and CHO derived cells expressing the genomically integrated EBNA1 protein as well as the SV40 large T-antigen (CHO-EBNA-T). Other CHO derived cells known in the art can be used for the present invention, such as for example CHO derived cells adapted to serum-free growth conditions.

In a preferred embodiment of the invention, the recombinant host cell is a hamster cell, preferably a CHO cell or a CHO derived cell, even more preferably a CHOK1 cell, CHO-EBNA cell, a CHO-T cell, a CHO-EBNA-T cell or a cell derived thereof, and the at least one gene of interest (A1), the at least one S/MAR (B1), the at least one origin of replication (C1), and the at least one replication initiation factor (D1) are in the consecutive order of A1-C1-D1-B1, preferably promA1pa-C1-paD1prom on the inventive nucleic acid molecule or vector system, respectively. In a very preferred embodiment, the recombinant host cell is a CHOK1 cell, the nucleic acid molecule or expression vector comprises two genes of interest (A1 and A2) and the consecutive order on the inventive nucleic acid molecule or expression vector, respectively, is prom A1pa-promA2pa-C1-paD1prom-B1. In a further embodiment of the invention, the recombinant host cell is a CHOK1 cell and the nucleic acid molecule or expression vector, respectively, comprises at least one gene of interest (A1), at least one S/MAR (B1), at least one origin of replication (C1), at least one replication initiation factor (D1) and at least one further S/MAR (B2) and the consecutive order is A1-B2-C1-D1-B1, preferably promA1pa-B2-C1-paD1prom-B1, on the inventive nucleic acid molecule or vector system, respectively.

In another preferred embodiment of the present invention, the host cell is an animal cell, preferably a mammalian cell, more preferably a human cell, most preferably a 293 derived cell. Preferred cells for the production of polypeptides according to the invention are 293 HEK (human embryonic kidney) cells or 293 EBNA1 cells. Other 293 derived cells suitable for the present invention include without limitation 293c18 (e.g. CRL-10852 deposited at ATCC, U.S.A. depository acknowledged under Budapest Treaty), 293T/17 (e.g. CRL-11268 deposited at ATCC, U.S.A. depository acknowledged under Budapest Treaty), 293T, ANJOU 65 (e.g. CRL-11269 deposited at ATCC, U.S.A. depository acknowledged under Budapest Treaty), BOSC 23 (e.g. CRL-11270 deposited at ATCC, U.S.A. depository acknowledged under Budapest Treaty), PPA.6 (e.g. CRL-12006 deposited at ATCC, U.S.A. depository acknowledged under Budapest Treaty), PP-X36 (e.g. CRL-12007 deposited at ATCC, U.S.A. depository acknowledged under Budapest Treaty), 2A (e.g. CRL-12013 deposited at ATCC, U.S.A. depository acknowledged under Budapest Treaty), PP-A52 (e.g. CRL-12479 deposited at ATCC, U.S.A. depository acknowledged under Budapest Treaty), WSS-1 (e.g. CRL-2029 deposited at ATCC, U.S.A. depository acknowledged under Budapest Treaty), 293/CHE-FC (e.g. CRL-2368 deposited at ATCC, U.S.A. depository acknowledged under Budapest Treaty), 293 EcRShh (e.g. JHU-64 deposited at ATCC, U.S.A. depository acknowledged under Budapest Treaty), 293F, or 293 derived cells expressing the genomically integrated EBNA1 protein or large T-antigen, such as e.g. 293EBNA1 cells or 293T cells. Other 293 derived cells known in the art can be used for the present invention, such as for example 293 derived cells adapted to serum-free growth conditions.

In a preferred embodiment of the invention, the recombinant host cell is a human cell, more preferably a 293 derived cell, even more preferably 293 EBNA cell, and even more preferably 293 T cell. Preferably, the at least one gene of interest (A1), the at least one S/MAR (B1), the at least one origin of replication (C1), and the at least one replication initiation factor (D1) are in the consecutive order of A1-B1-C1-D1, preferably promA1pa-B1-C1-paD1prom, on the nucleic acid molecule or vector system, respectively, of the invention. In a further embodiment, the recombinant host cell is a 293 EBNA cell, comprising at least one gene of interest (A1), at least one S/MAR (B1), at least one origin of replication (C1), at least one replication initiation factor (D1) and at least one further S/MAR (B2) and the consecutive order is A1-B1-C1-D1-B2, preferably promA1pa-B1-C1-paD1prom-B2, on the inventive nucleic acid molecule or vector system, respectively.

The nucleic acid molecules and/or expression systems of the invention may be introduced into host cells using well known techniques of infection, transduction, electroporation, transfection, and transformation. Exemplary methods include DEAE-dextran mediated transfection, transient transfection, microinjection, cationic lipid-mediated transfection, scrape loading and ballistic introduction. Preferably, the nucleic acid molecule and/or expression system of the invention is introduced into the host cell by way of transfection. Methods for the introduction of exogenous DNA sequences into host cells are discussed in Felgner, P. et al., U.S. Pat. No. 5,580,859. The nucleic acid molecules and/or vectors of the invention may be introduced alone or in conjunction with other nucleic acid molecules and/or vectors and/or proteins, peptides or RNAs. Alternatively, the nucleic acid molecules and/or expression systems of the invention may be introduced into host cells as a precipitate, such as a calcium phosphate precipitate, or in a complex with a lipid. Electroporation also may be used to introduce the nucleic acid molecules and/or expression systems of the invention into a host. Likewise, such molecules may be introduced into chemically competent cells such as E. coli. If the vector is a virus, it may be packaged in vitro or introduced into a packaging cell and the packaged virus may be transduced into cells. Hence, a wide variety of techniques suitable for introducing the nucleic acid molecules and/or vectors of the invention into host cells are well known and routine to those of skill in the art. Such techniques are reviewed at length, for example, in Sambrook, J., et al., Molecular Cloning, a Laboratory Manual, 2nd Ed., Cold Spring Harbor, N.Y.: Cold Spring Harbor Laboratory Press, pp. 16.30-16.55 (1989), Ausubel, F. et al., eds., CURRENT PROTOCOLS IN MOLECULAR BIOLOGY, John H. Wiley & Sons, Inc. (1997), Chapter 16), Watson, J. D., et al., Recombinant DNA, 2nd Ed., New York: W. H. Freeman and Co., pp. 213-234 (1992), and Winnacker, E.-L., From Genes to Clones, New York: VCH Publishers (1987), which are illustrative of the many laboratory manuals that detail these techniques and which are incorporated by reference herein in their entireties for their relevant disclosures.

The invention is also directed to recombinant host cells comprising one or more nucleic acid molecules or expression systems of the invention. Also included within the present invention are in vitro cell cultures that comprise recombinant host cells of the invention. Methods for producing recombinant host cells and cell cultures comprising the same are well-known in the art.

In a preferred embodiment, the nucleic acid molecule or expression system, respectively, of the present invention does not integrate into the host genome.

The in-vitro expression of one or more genes is likewise important as a use of the vector according to the invention or its cells. The vector thus makes possible a strong expression of genes and thus, for example, the preparation of proteins and peptides in large amounts in various cells and cell systems of both eukaryotic and prokaryotic type, without continuously placing the cells under selection pressure, which adversely effects both the protein yield and increases the process costs. Using the vector, it is also possible to express genes which code for proteins or peptides and which until now it has not yet been possible to express without difficulty—in particular in sensitive cell systems.

A further aspect of the invention is also the use of a vector according to the invention for the transfection of cells. Transfection is understood as meaning the inclusion of the vector in the cell such as for example the transformation of prokaryotic cells, for example for the propagation of the vector. Otherwise, the invention also includes the use of the vectors according to the invention for the production of transgenic animals or stem cells, for example embryonic stem cells, since these vectors are suitable for use, in particular, in eukaryotic cells, and also for use for research purposes.

The invention in this case also includes as a further subject a composition which contains at least one of the vectors according to the invention and/or a cell which contains such a vector, and suitable additives and/or auxiliaries. The suitable additives and auxiliaries are to be understood as meaning, in particular, adjuvants, stabilizers and/or transfection-facilitating substances. Also covered are transfection systems including transfection vectors, which are combined or associated with the vector according to the invention and its penetration into cells, which facilitate or even allow transfection or alternatively transformation. Auxiliaries are in particular to be understood as also meaning general protease inhibitors, such as PMSF, and nuclease inhibitors, such as EDTA.

According to another aspect of the invention, methods are provided for producing the expression of a polypeptide or untranslated RNA molecule. The methods according to this aspect of the invention comprise: (a) introducing a nucleic acid molecule or an expression system of the invention into a host cell to produce a recombinant host cell; and (b) culturing said recombinant host cell under suitable conditions. The recombinant host cells may be cultured, e.g., in a serum-free or protein-free medium. The methods of the invention may further comprise recovering said polypeptide or untranslated RNA molecule.

The nucleic acid molecules, expression vectors, expression systems and recombinant host cells of the invention may be used for the production of proteins, polypeptides and RNA molecules, e.g., untranslated RNA molecules. The methods of the invention may comprise, e.g., introducing one or more nucleic acid molecules or expression systems of the present invention into host cells to produce recombinant host cells, culturing the recombinant host cells under conditions suitable for expression of the polypeptide or untranslated RNA molecule, and recovering the polypeptide or untranslated RNA molecule.

The invention also provides methods for producing a polypeptide or an untranslated RNA molecule. The methods of the invention may comprise, e.g., (a) introducing one or more nucleic acid molecules or expression systems of the invention into a host cell to produce a recombinant host cell, wherein said nucleic acid molecules or expression systems comprise at least one gene of interest, at least one scaffold/matrix attached region (S/MAR), at least one origin of replication (ORI), and at least one replication initiation factor capable of recognizing said origin of replication, and (b) growing said recombinant host cell under suitable culture conditions.

Depending on the molecule, which is expressed, it may be obtained either from the culture supernatant or by lysing the recombinant host cells.

Polypeptides produced using the nucleic acid molecules and expression systems of the invention can be recovered and purified from recombinant cell cultures by methods known in the art including ammonium sulfate precipitation, anion or cation exchange chromatography, phosphocellulose chromatography, hydrophobic interaction chromatography, affinity chromatography, hydroxylapatite chromatography, and high performance liquid chromatography. Methods for purifying proteins are described in numerous sources (see, e.g., Celis, J., ed., CELL BIOLOGY, Academic Press, $2^{nd}$ edition, (1998)).

Untranslated RNA molecules produced using the nucleic acid molecules and expression systems of the invention can be recovered and purified from recombinant cell cultures by methods known in the art (see, e.g., Celis, J., ed., CELL BIOLOGY, Academic Press, $2^{nd}$ edition, (1998)). Methods for recovering and/or purifying RNA molecules include phenol/chloroform extraction, digestion with DNAses followed by precipitation of the undigested RNA molecules, and column chromatography (e.g., oligo dT column chromatography).

Further, RNA molecules can be separated from other cellular material using the single-step guanidinium-thiocyanate-phenol-chloroform method described in Chomczynski and Sacchi, *Anal. Biochem.* 162:156-159 (1987).

The overall cell culture process employing nucleic acid molecules and expression systems of the invention for the production of polypeptides and/or untranslated RNA molecules can be implemented in a variety of bioreactor configurations (e.g., stirred-tank, perfused, membrane enclosed, encapsulated cell, fluidized bed, and air-lift reactors) and scales (from laboratory T-flasks to thousands of liters), chosen to accommodate the requirements of the host cell line utilized (e.g., anchorage dependency, $O_2$ concentrations), to maximize the production of expression product, and to facilitate subsequent recovery and purification of expression product.

The invention is also directed to the production of polypeptides or RNA molecules of interest using mammalian cells grown in serum-free or protein-free culture media. For example, by long-term culture under conditions restricting serum access or selecting for suspension growth, CHO cell lines are selected which are able to grow in serum-free medium and/or in suspension (Zang. M. et al., *Bio/Technology* 13:389 (1995)).

Further, a number of different bioprocess parameters can be varied in order to alter the glycosylation pattern of polypeptide products produced by the recombinant host cells of the invention. These factors include medium composition, pH, oxygen concentration, lack or presence of agitation, and, for the case of anchorage-dependent cells, the surface provided. Thus, the glycosylation pattern of glycoproteins may be altered by choosing the host cell in which these proteins are expressed in and the conditions under which the recombinant host cells are grown.

The invention further provides pharmaceutical compositions comprising nucleic acid molecules and/or expression systems and/or recombinant host cells of the invention. The pharmaceutical compositions of the invention may comprise nucleic acid molecules and/or expression systems and/or recombinant host cells of the invention in combination (e.g., in solution) with a physiologically acceptable carrier and in a therapeutically effective amount. The administration of these pharmaceutical compositions may, for example, result in expression of a polypeptide in tissues of an animal which is immunogenic and intended to function as a vaccination. Similarly, the nucleic acid molecules and/or expression systems and/or recombinant host cells of the invention may carry sequences that encode polypeptides or RNA molecules required for the treatment of an active affliction. The administration of a pharmaceutical composition of the invention will thus be intended to have a therapeutic effect in these instances.

The nucleic acid molecules and/or expression systems and/or recombinant host cells of the invention will normally be administered to an individual in a pharmacologically acceptable carrier. A composition is said to be "pharmacologically acceptable" if its administration can be tolerated by a recipient individual. Further, the composition of the invention will be administered in a "therapeutically effective amount" (e.g., an amount that produces a desired physiological effect).

As would be understood by one of ordinary skill in the art, when the nucleic acid molecules and/or expression systems and/or recombinant host cells of the invention are administered to an individual, they may be in a composition which contains salts, buffers, adjuvants, or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1980)).

The pharmaceutical compositions of the present invention can be administered by various art known means but will normally be administered by injection, infusion or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

When recombinant host cells are administered to an individual, the number of cells or nucleic acid molecules required to provide a therapeutically effective amount will vary with such factors as the individual's condition, the polypeptides or RNA molecules intended to be expressed, and the size of the individual.

The invention also provides kits comprising the isolated nucleic acid molecules, expression systems and/or recombinant host cells of the invention. The kits of the invention may optionally comprise one or more additional components selected from the group consisting of one or more containers (e.g., boxes, vials, tubes, jars ampules, etc.) one or more vectors, one or more nucleotides, one or more primers, one or more polypeptides having polymerase activity, one or more host cells (e.g., host cells that may be competent for uptake of nucleic acid molecules), and one or more buffers.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Generation of Expression Constructs

Cloning of Human Beta Interferon S/MAR

Manipulations and sequencing of DNA were carried out by standard procedures. The S/MAR (scaffold/matrix attached region) element from the 5'region of the human β-interferon gene (β-IFN) was obtained by PCR (polymerase chain reaction) amplification from human genomic DNA (Novagen, EMD Biosciences, Merck, Darmstadt, Germany). The 2.2 kb DNA fragment was amplified using an appropriate forward SMfwd (SEQ ID NO: 1) and reverse primer SMrev (SEQ ID NO: 2). SMfwd corresponds to nucleotides 6644-6670 and SMrev to nucleotides 8878-8852 of locus NT_023974 of *Homo sapiens* chromosome 9. Amplification was performed using KTLA polymerase (DNA polymerase technology, Inc.) according to manufacturer's recommendations. Reaction conditions were 21 cycles at following settings: 50sec at 94° C., 50sec at 60° C.

and 3 min at 68° C. The amplified DNA fragment (S/MAR, SEQ ID NO: 3) was then digested with EcoR1 and subcloned into the EcoR1 site of the pGem-T Easy vector (Promega). The resulting plasmid was named pGemT-S/MAR.

GOI—Expression Cassette

To test different expression constructs, a recombinant antibody was expressed. A schematic representation of the expression cassette is shown in FIG. 1A. Briefly the cassette contains a first CMV promoter, an intron, the cDNA sequence of the light chain of an antibody (A1), a polyadenylation signal sequence (pA), a second CMV promoter, a second intron and the genomic sequence of the heavy chain of the same antibody (A2) followed by a polyadenylation signal sequence (pA). This cassette contained blunt ends on both sides and was subcloned into the different expression vectors. The cassette was named A1A2. The resulting constructs expresses a functional antibody, which can be measured by sandwich ELISA.

Generation of pCB_A1A2, pCB_SM1_A1A2 and pCB_SM2_A1A2

As a control the A1A2 cassette was introduced into pCep-pu vector, (SEQ ID NO: 4) (Wuttke et al., J Biol Chem, 2001, 39, 36839-48). Briefly pCep-pu was digested with BglII and BamHI, and the ends were blunt ended using Klenow polymerase according to the manufacturer's recommendations. Then the A1A2 fragment was ligated into the vector. The resulting construct where the expression cassette was in the orientation shown in FIG. 1B was named pCB_A1A2. Two different types of expression vectors containing the β-IFN S/MAR element were generated in the following way. Briefly the S/MAR cassette was excised from pGemT-S/MAR by EcoRI digestion and the ends were filled in using T4 DNA polymerase. This cassette was then subcloned into pCB_A1A2 which had been digested with XbaI and blunted using T4 DNA polymerase. The resulting constructs was named pCB_A1A2_SM1.

Figure 1B:
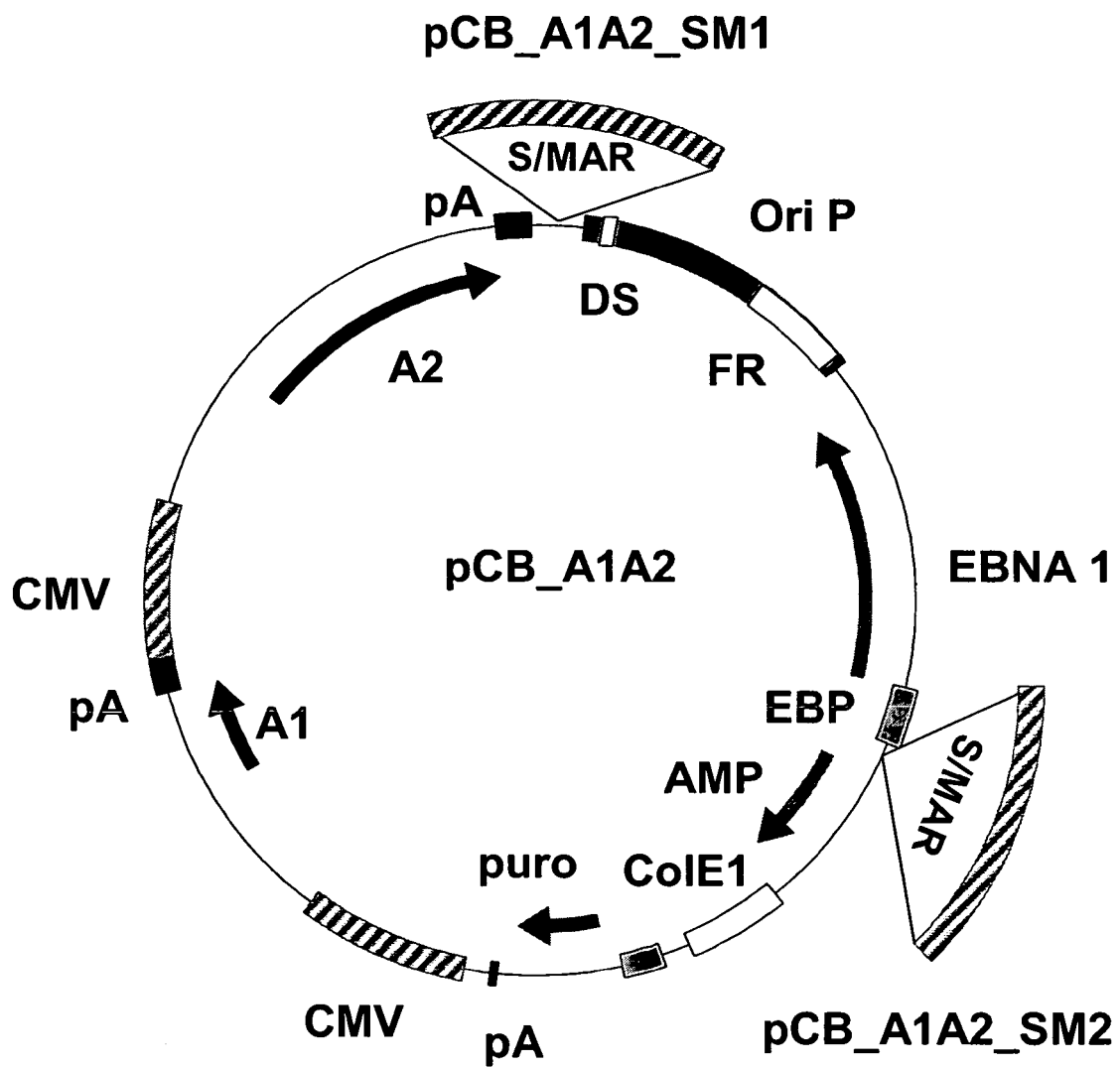
FIG. 1B shows a schematic representation of the expression vectors used. The control pCB_A1A2 expression vector with the different features is shown. The locations where the S/MAR element was introduced in pCB_A1A2_SM1 and pCB_A1A2_SM2 is shown outside of the circle with the name of the corresponding constructs. Used abbreviations are as follows: polyadenylation signal (pA), *cytomegalovirus* promoter (CMV), first gene of interest (A1), second gene of interest (A2), EBV origin of replication (Ori P), dyad symmetry (DS), family of repeats (FR), ampicilin resistance gene (AMP), bacterial origin of replication (Col E1), puromycin resistance gene (puro), EBNA1 promoter (EBP).

In order to introduce the β-IFN S/MAR element at different locations, a new polylinker was inserted into pCep-pu. Briefly the existing CMV promoter and poly A signals were removed by BglII and XbaI digestion and replaced by an annealed nucleotide pair (SEQ ID NO: 5 and SEQ ID NO: 6) which contains restriction sites for BglII, NheI, PvuII, HindIII and XbaI. The resulting vector was named pCB. The β-IFN S/MAR element was then introduced upstream of EBNA1 gene as follows: the S/MAR cassette was excised from pGemT-S/MAR by EcoRI digestion and cloned into the EcoRI site of pCB. The resulting constructs was named pCB_SM2. The antibody expression cassette (A1A2) was then inserted into the PvuII site of the polylinker of pCB_SM2 leading to construct pCB_A1A2_SM2. The general features of pCB_A1A2, pCB_A1A2$_{13}$SM1 and pCB_A1A2_SM2 are schematically shown in FIG. 1B.

Generation of pCep-LTBR-Fc and pCep-LTBR-Fc_SM1

In order to generate a construct which expresses the extracellular part of lymphotoxin-beta receptor (LTBR) fused to the constant region of human IgG (Fc), the extracellular part of the LTBR was amplified by PCR and cloned into pCep derived vector containing the constant part of human IgG. Briefly the extracellular part of LTBR was amplified by PCR from mouse spleen cDNA using primer pair LTBRfwd (SEQ ID NO: 7), which contains an additional BamHI site and LTBRrev (SEQ ID NO: 8) which contains an NheI site. The PCR fragment was then digested with BamHI and NheI and cloned into the previously described vector pCep-EK-Fc* (WO_02056905_A2, example 1). The resulting construct was named pCep$_{13}$LTBR-Fc. In order to generate a vector which expresses the same protein but contains a S/MAR element at position 1 (SM1), the 2.2 kb XbaI fragment from pCB_A1A2_SM1 containing the S/MAR element was introduced into pCep-LTBR-Fc partially digested with XbaI. The construct which contains the S/MAR element between the polyadenylation signal of the gene of interest and OriP was named pCep_LTBR-Fc_SM1.

Generation of pCB1, pCB2, pCB3 and pCB2- and pCB3-S/MAR Vectors

To improve the expression levels of EBNA1 in the novel expression vectors, the endogenous EBNA1 promoter, which has been shown to lead to weak expressions in certain cell types, was replaced by either the SV40 promoter or the promoter of human polypeptide chain elongation factor 1 alpha (EF-1a). Both these promoters are strong constitutive promoters which have been reported to display good expressions in a variety of cell lines. Briefly, the previously described plasmid pCep-MCS (WO-02056905, example 1) was digested with BglII and XbaI and the 8.2 kb fragment was ligated with the annealed oligonucleotides PH86 (SEQ ID NO: 9) and PH87 (SEQ ID NO: 10), the resulting construct was named pCep-D1. Then pCep-D1 was digested with BglII and the 700 bp fragment from pCep-MCS digested with BglII, containing the CMV promoter was introduced in the same orientation as in the original pCep-MCS plasmid, the construct was named pCep-D2. In order to introduce new polyadenylation sequence into the new vector a sequence containing part of the polylinker and the new polyadenylation signal was generated as follows; pcDNA-4-his-B (Invitrogen) was digested with Bsp120I and XhoI and ligated to the annealed oligonucleotides PH088 (SEQ ID NO: 11) and PH089 (SEQ ID NO: 12) leading to construct pcDNA-MCS. Then the 300 bp fragment of pcDNA-MCS digested with XhoI and PvuII was introduced into pCep-D2 digested with XhoI and PvuII leading to pCB1.

The EBNA1 promoter (EBP) was removed from pCB1 by digestion with AvrII and ClaI and replaced by the annealed oligonucleotides PH094 (SEQ ID NO: 23) and PH095 (SEQ ID NO: 24) leading to the plasmid pCB1_dEBP. The EF1-alpha promoter was amplified by PCR from pEF/myc/cyto (Invitrogen Life Technology), using primers LI17 (SEQ ID NO: 13) and LI118 (SEQ ID NO: 14). The PCR fragment was then digested with ClaI and cloned into the only ClaI site of pCB1_dEBP which is not blocked by methylation leading to construct pCB2. The SV40 promoter was amplified by PCR from pcDNA3.1 (Invitrogen Life Technology), using primers LI15 (SEQ ID NO: 15) and LI16 (SEQ ID NO: 16). The PCR fragment was then digested with ClaI and cloned into the only ClaI site of pCB1_dEBP which is not blocked by methylation leading to construct pCB3. For the new constructs, pCB2 and pCB3, the orientation of the promoters was chosen, which leads to expression of EBNA1 open reading frame. The S/MAR element at position 1 and position 2 respectively is introduced into pCB1 and pCB2 as follows: the 2.2 kb EcoRI fragment from pGemT-S/MAR is introduced into the EcoRI sites of pCB2 and pCB3 leading to constructs pCB2_SM2 and pCB3_SM2 respectively, which contain the S/MAR element upstream of the promoter driving the expression of the EBNA1 open reading frame. To generate vectors which contain the S/MAR element between the gene of interest and OriP, the 2.2 kb Xba I fragment of pCB_A1A2_SM1 is introduced into the XbaI sites of pCB2 and pCB3 leading to pCB2_SM1 and pCB3_SM1. In order to perform some stability and expression tests with these vectors, a model gene of interest (LTBR-Fc) is introduced into the vectors as follows. The ends of the 1.4 kb fragment of pCep-LTBR-Fc partially digested with BamHI and XhoI are filled in using T4 DNA polymerase and the blunt ended fragment containing the extracellular domain of LTBR fused to the Fc part of human IgG is introduced into the PmeI sites of pCB2_SM2, pCB3_SM2, pCB2_SM1 and pCB3_SM1 leading to constructs pCB2_LTBR-Fc_SM2, pCB3_LTBR-Fc_SM2, pCB2_LTBR-Fc_SM1 and pCB3_LTBR-Fc_SM1 respectively. respectively.

Generation of Vectors with Functional Variants of EBNA1

Further vectors which contain OriP and β-IFN S/MAR element at position 1 (SM1) or 2 (SM2) and variants of EBNA1 are generated as follows. Briefly, the vector pCep4 was digested with DraIII and ClaI. The resulting 4651 bp fragment was purified and blunt ends were generated by T4 DNA polymerase treatment. This fragment was then subcloned into pGEMTeasy vector (Promega), which had previously been digested with EcoRI and treated with Klenow polymerase in order to get blunt ends. The resulting construct was termed pGemT-OPE. The different EBNA1 mutants are generated using QuickChange mutagenesis kit (Stratagene, La Jolla, Calif.) following the manufacturers' recommendations and using indicated complementary oligonucleotides and indicated plasmid templates. Briefly, the indicated primers are annealed to the template plasmid DNA and extended using proof reading Pfu DNA polymerase (Promega), and then the reaction is treated with DpnI to digests the methylated parental DNA. The remaining mutagenized DNA is then transformed into E. coli competent cells. Positive clones are confirmed by sequencing for presence of the deletion. To generate EBNA1 containing a deletion of amino acids 61-83 (EBNA1-d1), primer pair LI19 (SEQ ID NO: 17) and LI20 (SEQ ID NO: 18) is used on pGem-OPE as a template leading to construct pGem-OPE_EBNA1-d1. To generate EBNA1 containing a deletion of amino acids 395-450 (EBNA1-d2), primer pair LI21 (SEQ ID NO: 19) and LI22 (SEQ ID NO: 20) is used on pGem-OPE as a template leading to construct pGem-OPE_EBNA1-d2. Finally to generate the mutant which contains a deletion of amino acids 61-83 and a deletion of amino acids 395-450, primer pair LI21 (SEQ ID NO: 19) and LI22 (SEQ ID NO: 20) is used on pGem-OPE_EBNA1-d1 leading to construct pGem-OPE_EBNA1-d3. From these three vectors, the mutated part of EBNA1 gene can be excised by BlnI/SgrAI digestion and introduced into the different S/MAR containing expression vectors. The 1.5 kb BlnI/SgrAI fragment of pGem-OPE_EBNA1-d1 is inserted into the BlnI/SgrAI sites of pCB_A1A2_SM1 and pCB_A1A2_SM2 leading to pCB_A1A2_SM1_EB-d1 and pCB_A1A2_SM2_EB-d1, The 1.5 kb BlnI/SgrAI fragment of pGem-OPE_EBNA1-d2 is inserted into the BlnI/SgrAI sites of pCB_A1A2_SM1 and pCB_A1A2_SM2 leading to pCB_A1A2_SM1_EB-d2 and pCB _A1A2_SM2_EB-d2. And the 1.5 kb Bln I/SgrAI fragment of pGem-OPE_EBNA1-d3 is inserted into the BlnI/SgrAI sites of pCB_A1A2_SM1 and pCB_A1A2_SM2 leading to pCB_A1A2_SM1_EB-d3 and pCB_A1A2_SM2_EB-d3.

Generation of S/MAR OriP Vectors Without EBNA1

In order to evaluate the importance of EBNA1 protein in plasmid replication and maintenance in the presence of OriP and β-IFN S/MAR element, the promoter driving EBNA1 expression and the majority of the open reading frame of EBNA1 was removed. Briefly, pCep_LTBR-Fc_SM1 was digested with SgrA1 and ClaI, DNA ends were blunted with the help of Klenow polymerase and the 11.6 kb fragment was purified and self-ligated, leading to construct pCep_dEB_LTBR-Fc_SM1. This construct does no longer express EBNA1.

Generation of S/MAR Vectors with Extended OriP

Further vectors containing an extended OriP covering base pairs 4948 to 9520 of Epstein-Barr virus B95-8 strain (NCBI: NC_001345) in conjunction with β-IFN S/MAR element are generated. Briefly, the fragment covering nucleotides 4948-9007 from B95-8 is amplified by PCR from Raji cells using primers EoriFwd (SEQ ID No. 21) and EoriRev (SEQ ID No. 22). Primer EoriFwd is located in the region of the endogenous EcoRV site, whereas EoriRev contains an additional MunI site. The 4.1 kb PCR fragment is then digested with EcoRV and MunI and introduced into pCB 1 digested with EcoRV/MunI leading to pCB4. To generated constructs which express a gene of interest in presence of β-IFN S/MAR element and extended OriP, the Xba I fragment of pCB_A1A2_SM1 containing the S/MAR element is introduced into the Xba I site of pCB4 leading to pCB4_SM1 or as an EcoRI fragment from pGemT-S/MAR into the EcoRI site of pCB4 partially digested with EcoRI leading to pCB4_SM2. In pCB4_SM2 the S/MAR element is located upstream of the EBNA1 promoter. In order to perform stability and expression tests with these vectors, a model gene of interest (LTBR-Fc) is introduced into the vectors as follows. The ends of the 1.4 kb fragment of pCep-LTBR-Fc partially digested with BamHI and XhoI are filled in using T4 DNA polymerase and the blunt ended fragment containing the extracellular domain of LTBR fused to the Fc part of human IgG are introduced into the PmeI sites of pCB4_SM1 and pCB4_SM2 leading to constructs pCB4_LTBR-Fc_SM1 and pCB4_LTBR-Fc_SM2.

Example 2

Quantification of the Produced Proteins by ELISA

Antibody Production by ELISA

The productivity of the transfected cells with regard to the assembled antibody was assessed using a sandwich ELISA (Enzyme Linked Immono Sorbent assay) method. Microtiter polystyrene plates (#442404, Nalge-Nunc International) were pre-coated overnight at 4° C. with goat anti-human IgG Fc (#109-006-098, Jackson Immunoresearch Labs Inc.) at a concentration of 5 µg/ml in 0.1M sodium carbonate, pH 9.6.

The plates were then washed and incubated with blocking buffer supplemented with casein for 1 h at room temperature. Appropriate dilutions of the samples were then made, added to the plates and incubated for 1 h at RT. The plates were then washed several times with washing buffer in order to remove unbound proteins. The plates were then stained with a goat anti-human IgG kappa horseradish peroxidase conjugate (#H16007, Caltag) at a dilution of 1:5000 for 45 minutes at room temperature. After extensive washing, the bound complexes were visualized using the chromogenic substrate tetramethylbenzidine (TMB, #T0440, Sigma-Aldrich Chemie GmbH). Levels of assembled antibody were estimated based on a standard with known concentration.

Fc ELISA

The productivity of the transfected cells with regard to the LTBR-Fc fusion protein was assessed using a sandwich ELISA specific for the Fc part of the protein. Briefly microtiter polystyrene plates (#442404, Nalge-Nunc International) with anti-human-IgG at 1.8 mg/ml (Jackson ImmunoResearch laboratories, No. 109-005-098) overnight at 4° C., then the plates were washed with washing buffer (PBS/ 0.05% Tween). The plates were then blocked with 4% milk powder in PBS for 1 h at room temperature. After three washes with washing buffer, serial dilutions of supernatants in PBS supplemented with 1% BSA were applied to the plates and incubated for 2h at room temperature. Unbound proteins were removed by 5 washes with washing buffer. To detect bound fusion protein, the plates were incubated with a peroxidase conjugated goat anti human IgG antibody (Jackson ImmunoResearch laboratories, No. 109-035-098) diluted 1/10 000 in PBS supplemented with 1% BSA. After extensive washing the bound complexes were visualized using the chromogenic substrate tetramethylbenzidine (TMB, No. T0440, Sigma-Aldrich Chemie GmbH). Absolute values were then calculated based on a standard with known concentration.

Example 3

Figure 2:
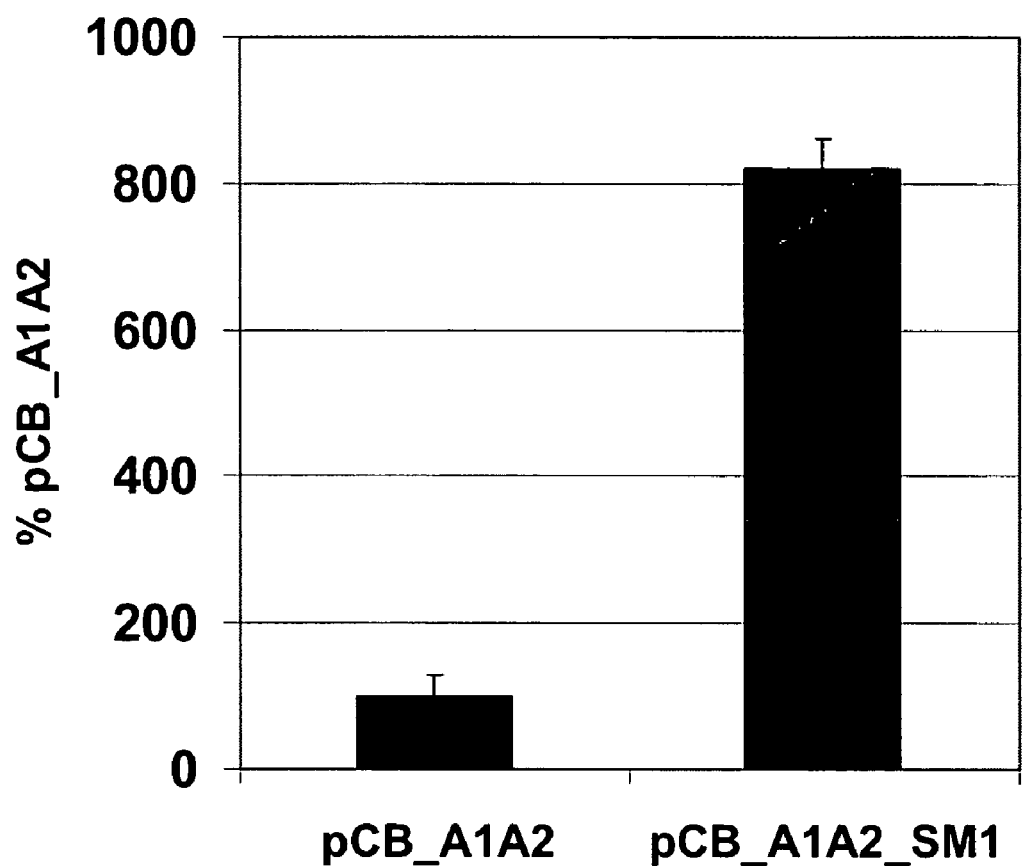
FIG. 2: Drastically increased expression levels in 293-EBNA cells with pCB_A1A2SM1. 293-EBNA cells were transfected with pCB_A1A2 and pCB_A1A2_SM1 and passaged under selective medium. After all the non transfected cells had died, the cells were seeded for production. After the cells had reached confluence, medium was changed to production medium. 5 days later the supernatants were harvested and the antibody production was measured by ELISA. The productivity relative to the control vector (pCB_A1A2) is shown. The error bars correspond to the standard deviation of three independent transfections. pCB_A1A2_SM1 showed a roughly 8 fold improvement of productivity compared to the control vector.

Substantially Improved Expression Levels in 293-EBNA Cells with S/MAR Containing Constructs To asses the productivities, of the new constructs, 293-EBNA cells were transfected with the antibody expressing constructs. Briefly, 293-EBNA cells were propagated in DMEM supplemented with 10% FCS. The cells were seeded the day before transfection and transfected with pCB_A1A2 and pCB_A1A2_SM1 using Lipofectamin 2000 (Invitrogen) according to the manufacturer's recommendations. 24-36 h after transfection the cells were passaged under puromycin selection (1 µg/ml). After 2-3 days all non transfected cells had died and the surviving cells were seeded on poly-L-Lysine coated plates. Once the cells had attached and reached confluence, the medium was changed to serum free production medium (DMEM/F12, reduced glutathione 10 mg/l, N-Acetyl-L-Cysteine 161 mg/ml, puromycin 1 mg/l). Five days after medium change supernatants were harvested and the antibody production was monitored by ELISA (see example 2). As shown in FIG. 2, the construct pCB_A1A2_SM1 which contains the S/MAR element downstream of the gene of interest (position 1, see also FIG. 1B) showed a roughly 8 fold improvement of the productivities compared to the control vector which does not contain any S/MAR element. In conclusion, a vector containing an EBV origin of replication (Ori P), the EBV replication initiation and maintenance factor EBNA1 and a S/MAR element between the gene of interest and Ori P leads to a drastic improvement of the expression levels. This high productivity achieved by the combination of the three elements is of great value for the rapid generation of large quantities of recombinant proteins.

Substantially Improved Expression Levels in 293-EBNA Cells with pCB_LTBR-Fc_SM1

To asses the productivities of the new vector with another gene of interest, 293-EBNA cells were transfected with the new construct expressing LTBR-Fc. Briefly, 293-EBNA cells were transfected with pCep-LTBR-Fc and pCep-LTBR-Fc_SM1 using Lipofectamin 2000 according to the manufacturer's recommendations (Invitrogen). One day after transfection the cells were split under puromycin selection (1 µg/ml). After 2-3 days of selection all non transfected cells had died and detached from the plates. Resistant cells were then passaged under selective pressure on poly-L-lysine coated plates for production. Once the cells had reached confluence the medium was changed to serum free production medium (DMEM/F12, reduced glutathione 10 mg/l, N-Acetyl-L-Cysteine 161 mg/ml, puromycin 1 mg/l). After 6 days supernatants were harvested and analyzed by an Fc specific ELISA (see example 2) for the productivities.

As shown in table 1, the S/MAR containing vector showed a 6.3× improved expression levels as compared to the pCep control vector. Hence similar improvement of the expression levels was observed with the LTBR-Fc fusion molecule as with the antibody expression cassette shown in example 3. In conclusion, the improved expression levels with the S/MAR containing vectors are independent of the expressed gene of interest.

TABLE 1

Improved productivities with pCep-LTBR-Fc_SM1 compared to pCep-LTBR-Fc

| Construct | mg/l |
| --- | --- |
| pCep-LTBR-Fc | 3.2 |
| pCep-LTBR-Fc_SM1 | 20 |

Example 4

Substantially Improved Proliferation Rates in 293-EBNA Cells with S/MAR Containing Constructs In order to asses the proliferation rates of the S/MAR containing vectors under selective pressure, 293-EBNA cells were transfected with pCB_A1A2_SM1 and as a control with pCB_A1A2 using Lipofectamin 2000 according to the manufacturer's recommendations (Invitrogen). One day after transfection the cells were passaged under puromycin selection (1 µg/ml). After 2-3 days all nontransfected cells had died, the resistant cells were from pCB_A1A2 and pCB_A1A2_SM1 transfected cells were then harvested by trypsinisation and counted. $5 \times 10^6$ cells of each construct were seeded into a T75 tissue culture flask. Every two days the cells were harvested and counted in order to determine the proliferation rates of the two cell populations. At each time point defined amount of cells was transferred to a new T75 tissue culture flask in order to monitor the long term effect of the S/MAR element on cell proliferation rates compared to cells transfected with a plasmid that does not contain S/MAR element under selective pressure. The results are shown in Table 2. The respective constructs are shown in the first row, the days in the second row, the amount of seeded cells in the third row, the cell number at the indicated time point in the fourth row the cumulative cell number in the fifth row and the amounts of doublings are shown in the sixth row.

TABLE 2

Improved proliferation rates with S/MAR containing vectors

|  | day | seeded cells | cell number | total cell number | doublings |
|---|---|---|---|---|---|
| pCB-A1A2 | 0 | 5.5E+06 | | | |
|  | 2 | 5.0E+06 | 1.4E+07 | 1.4E+07 | 1.4 |
|  | 5 | 5.0E+06 | 8.0E+06 | 2.2E+07 | 2.0 |
|  | 7 | 7.0E+06 | 8.4E+06 | 3.8E+07 | 2.8 |
|  | 9 | 5.0E+06 | 1.3E+07 | 7.0E+07 | 3.7 |
| pCB_A1A2 SM1 | 0 | 5.50E+06 | | | |
|  | 2 | 5.00E+06 | 1.9E+07 | 2.3E+07 | 1.5 |
|  | 5 | 5.00E+06 | 1.9E+07 | 8.8E+07 | 3.5 |
|  | 7 | 5.00E+06 | 2.1E+07 | 3.7E+08 | 5.5 |
|  | 9 | 4.00E+06 | 1.5E+07 | 1.1E+09 | 7.1 |

As documented by the substantially increased amounts of cells in the pCB_A1A2_SM1 transfected cells, the additional S/MAR element included in the expression vectors, significantly improved the proliferation rates under selective conditions. In fact 9 days after the starting of the experiments the cumulative amount of cells in the pCB_A1A2_SM1 transfected population was about 16 times greater than the ones obtained from pCB_A1A2 transfected cells. Visual observation of the cells also suggested, that the pCB_A1A2_SM1 appeared much healthier than the CB_A1A2 transfected cells, where a proportion of dead cells was found after each passage (data not shown). Thus, in the standard pCep system some cells lose the plasmids at each cell division even under selective pressure. Hence the additional S/MAR element also improves the plasmid maintenance under selective pressure.

Example 5

Figure 3:
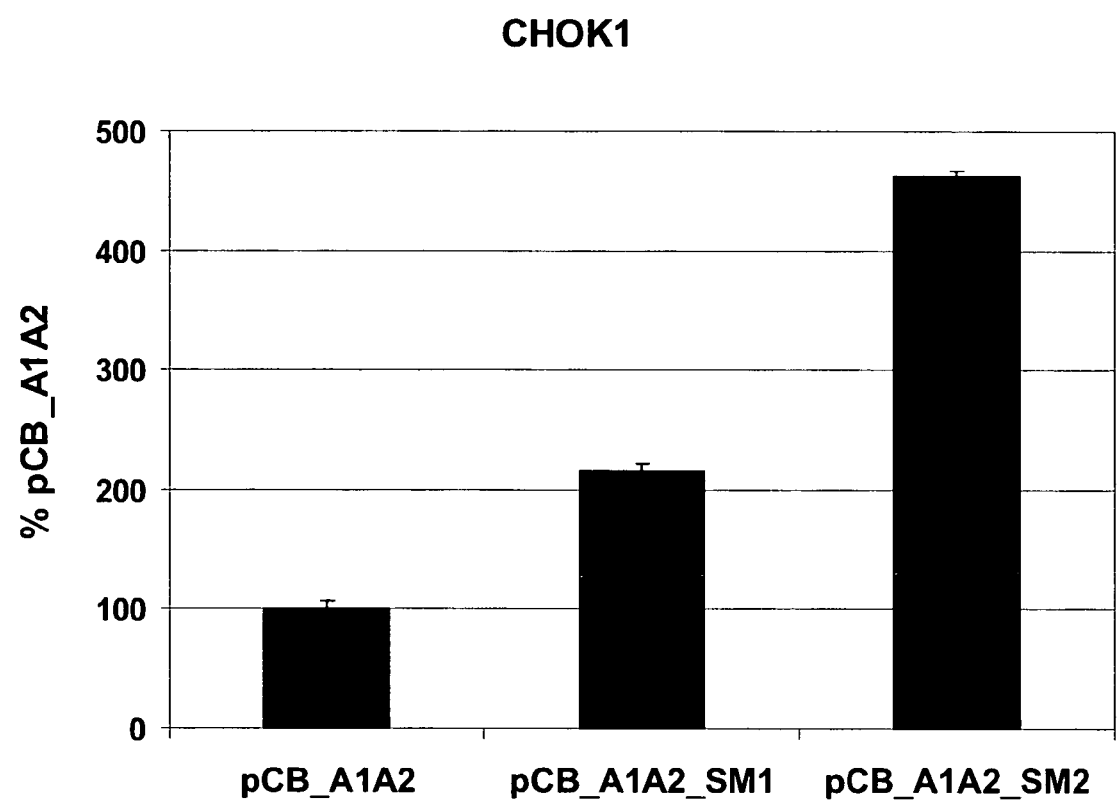
FIG. 3: Substantially improved expression levels in CHOK1 cells with pCB_A1A2_SM1 and pCB_SM2. CHOK1 cells were transfected with pCB_A1A2, pCB_A1A2_SM1 and pCB_A1A2_SM2 and passaged under selective medium. The cells were propagated for two weeks under selection and then seeded for production. Once the cells had reached confluence, the medium was changed and the cells were shifted to 29° C. 13 days later the supernatants were harvested and the antibody production was measured by ELISA. The productivities relative to the control vector (pCB_A1A2) are shown. The error bars correspond to the average deviation of two independent transfections. Both S/MAR containing constructs showed improved expression levels compared to pCB_A1A2. Whereas pCB_A1A2_SM1 displayed a two fold increase, pCB_A1A2_SM2 showed a 4.5 fold increase in expression levels.

Substantially Improved Expression Levels in CHOK1 cells with S/MAR Containing Constructs CHOK1 cells were propagated in DMEM supplemented with 5% FCS. The cells were seeded the day before transfection and transfected with pCB_A1A2, pCB_A1A2_SM1 and pCB_A1A2_SM2 using Lipofectamin 2000 (Invitrogen) according to the manufacturer's recommendations. 24-36 h after transfection the cells were passaged under puromycin selection (10 µg/ml). The cells were propagated under selective pressure for 2 weeks. Then the cells were seeded for production. Once they had reached confluence the medium was changed (DMEM supplemented with 5% FCS) and the cells were shifted to 29° C. After 13 days the medium was harvested and the antibody production was measured by ELISA. As shown in FIG. 3, whereas pCB_A1A2_SM1 showed 2-fold improved expression level, pCB_A1A2_SM2 showed even 4,5-fold improved expression level compared to the control vector pCB_A1A2. Hence, combination of an EBV origin of replication (OriP), the EBV replication initiation and maintenance factor (EBNA1) and S/MAR element leads to improved expression levels in CHOK1 cells. Moreover positioning of S/MAR element upstream of EBNA1 gene showed even higher expression levels than if the S/MAR element is positioned between the gene of interest and the OriP.

Example 6

The β-IFN S/MAR Element Together with the EBV OriP is not Sufficient for Efficient Replication and/or Maintenance of Plasmids in 293 Cells To test whether S/MAR element can functionally supplement the replication initiation and maintenance factor (EBNA1), as has been shown in the context of SV40 origin of replication in conjunction with S/MAR element (Bode et al., Gene therapy and Molecular Biology, January 2000, Vol 6, 33-46), constructs were generated which contain the gene of interest under the control of CMV promoter, the EBV OriP in presence of EBNA1 (pCep_LTBR-Fc_SM1) or the absence of EBNA1 (pCep_dEB_LTBR-Fc_SM1). In a first set of experiments the two constructs were tested in 293-EBNA1 cells which provide EBNA1 protein in trans. Briefly 293-EBNA cells were transfected with pCep_dEB_LTBR-Fc_SM1 and pCep_LTBR-Fc_SM1 using Lipofectamin 2000 according to the manufacturer's recommendations. One day after transfection cells were passaged under puromycin selection (1 µg/ml). After 2-3 days all non transfected cells had died and detached from the plates. Similar amounts of cells survived the selection with both constructs (data not shown). After puromycin selection the resistant cells were seeded on poly-lysine coated plates and re-fed next day with a serum free production medium (DMEM/F12, reduced glutathione 10 mg/l, N-Acetyl-L-Cysteine 161 mg/ml, puromycin 1 mg/l). Nine days later samples were collected and protein production was monitored by an Fc specific ELISA (example 2). As shown in table 3, both constructs displayed similar expression levels. Hence the fact that similar survival rates are observed after selection and similar protein production is observed with the two constructs demonstrates that the newly generated construct which does not contain the EBNA1 gene is functional in terms of replication if the EBNA1 protein is provided in trans from the integrated copy of EBNA1 gene in 293-EBNA cells.

TABLE 3

Productivities in 293-EBNA1 cells

| construct | mg/L |
|---|---|
| pCB_SM1_LTBR-Fc | 40 |
| pCB_SM1_dEB_LTBR-Fc | 38 |

The constructs were further tested in 293 cells, which do not provide EBNA1 protein in trans. Briefly, 293 cells were transfected with pCep_dEB_LTBR-Fc_SM1 and pCep_LTBR-Fc_SM1 using Lipofectamin 2000 according to the manufacturer's recommendations. One day after transfection, the cells were passaged under puromycin selection (1 µg/ml). After 2-3 days all non transfected cells had died and detached from the plates. Whereas a large proportion of the cells survived in pCep_LTBR-Fc_SM1, virtually all cells transfected with pCep_dEB_LTBR-Fc_SM1 died. These results demonstrate that the β-IFN S/MAR element together with OriP is not sufficient to lead to efficient replication or maintenance of the plasmid. Hence in contrast to the situation with an SV40 origin of replication, where the β-IFN S/MAR element is capable of functionally supplementing large T, the element is not sufficient to supplement for EBNA1.

Example 7

Testing of New Vector Variants for Efficient Replication and/Maintenance of Plasmids and Gene of Interest Expression in Eukaryotic Cells To test the different new constructs containing either mutants of EBNA1, stronger promoters for EBNA1 expression or an extended OriP in presence of the β-IFN S/MAR element 293, 293-EBNA and CHOK1 cells are transfected with the different plasmids. To test the effect of different EBNA1 mutants 293, 293-EBNA and CHOK1 cells are transfected with pCB_A1A2_SM1_EB-d1, pCB_A1A2_SM2_EB-d1, pCB_A1A2_SM1_EB-d2, pCB_A1A2_SM2_EB-d2 pCB _A1A2_SM1_EB-d3, pCB_A1A2_SM2_EB-d3, pCB_A1A2_SM1, pCB_A1A2_SM2 using Lipofectamin 2000 according to the manufacturer's recommendation. One day after transfection cells are passaged under selective conditions in the presence of puromycin (293 and 293-EBNA cells 1 µg/ml, CHO cells 10 µg/ml). 2 to 3 days later all nontransfected cells are dead and the resistant cells are passaged under selective conditions over several months and subjected to the different tests described below.

To test the constructs with different promoters and the ones with an extended OriP 293, 293-EBNA and CHOK cells are transfected with pCB-LTBR-Fc-SM1 pCB-LTBR-Fc-SM2, pCB2_LTBR-Fc_SM2, pCB3_LTBR-Fc_SM2, pCB2_LTBR-Fc_SM 1, pCB3_LTBR-Fc_SM1, pCB4_LTBR-Fc_SM1 and pCB4_LTBR-Fc_SM2 using lipofectamine 2000 according to the manufacturer's recommendation. One day after transfection cells are passaged under selective conditions in the presence of puromycin (293 and 293-EBNA cells 1 µg/ml, CHO cells 10 µg/ml). 2 to 3 days later all the nontransfected cells are dead and the resistant cells are passaged under selective conditions over several months and subjected to the different tests described below.

For further characterisation of the different new constructs, the resistant cells are passaged under selective conditions in regular intervals over several months and different parameters are evaluated. Particularly expression of the gene of interest, episome copy number and proliferation rates at different time points are determined. To measure the productivities of the different constructs a defined amount of cells is seeded as described in example 3 (293 and 293-EBNA cells) or as described in example 5 (CHO cells). Depending on the gene of interest, either Fc specific or antibody specific ELISA is performed as outlined in example 2. To asses the proliferation rates, at each splitting the cells are counted and defined amounts of cells are passaged to new plates as described briefly in example 4. Finally to monitor the maintenance and copy number of the episome a procedure described previously is used (Wu et al.; Journal of virology, 76, 5, 2480-2490). Briefly, $5 \times 10^6$ cells from each plate are harvested at each time point and lysed by the method of Hirt (Hirt, B., J. Mol. Biol. 1967, 26:365-369). Low-molecular weight DNA is then isolated as described by Ceccarelli and Frappier (Ceccarelli, D. F. J., and L. Frappier, J. Virol. 2000, 74:4939-4948), digested with XhoI and DpnI, separated by agarose gel electrophoresis, Southern blotted, and probed with $^{32}P$-labeled probes specific for the vectors. Linearized plasmid bands are visualized by autoradiography and quantified by phosphor-imager analysis using ImageQuant software (Molecular Dynamics).

Example 8

Improved Long Term Expression and Expression Levels by Second Replication Elements Derived from SV40

We further tested various constructs in 293-EBNA cells which constitutively express the EBNA1 gene and in 293-T cells which constitutively express the SV40 large T antigen. Please note hereby that all constructs derived from pCep-pu do contain the SV40 origin of replication. Briefly, 293-EBNA and 293-T cells were propagated in DMEM supplemented with 10% FCS. The cells were seeded the day before transfection and transfected with pCB_A1A2_SM1 and pCB2_A1A2_SM1 (see Example 1) using Lipofectamin 2000 (Invitrogen) according to the manufacturer's recommendations. 24-36 h after transfection the cells were passaged under puromycin selection (1 µg/ml). After 2-3 days all non transfected cells had died and the surviving cells were either seeded for a first round of production (production 1) or further propagated under selective pressure for an additional week and then seeded for a second round of production (production). Whilst the cells analyzed in production 1 had undergone roughly 6,5 doublings after transfection, cells that were seeded for production 2 had undergone roughly 10-12 doublings since transfection.

For production purposes cells were seeded onto poly-L_lysine coated plates and once the cells had attached and reached confluence, the medium was changed to serum free production medium (DMEM/F12, reduced glutathione 10 mg/l, N-Acetyl-L-Cysteine 161 mg/ml, puromycin 1 mg/l). Thirteen days after medium change supernatants were harvested and the antibody production was monitored by ELISA as described in Example 2. The obtained productivities in the different cell lines with the different constructs at the different time points are summarized in table 4. The constructs used are shown in the first column, the productivities during production 1 in the second column, the number of doublings after transfection for production 1 in the third column, productivities during production 2 in the fourth column, the number of doublings after transfection for production 2 in the sixth column an the cell line used in the seventh column. For production 2, the percentage of production one was calculated as follows (mg/l production 2/mg/l production 1)×100 and is indicated in the fifth column.

TABLE 4

Improved expression/stability with SV40 large T. The obtained values at the indicated time points are indicated including the standard deviations (pCB2_A1A2_SM1; n = 4, pCB_A1A2_SM1; n = 2) . . .

| Construct | Production 1 (mg/l) | doubl. | Production 2 (mg/l) | % of production 1 | doubl. | Cells |
|---|---|---|---|---|---|---|
| pCB_A1A2_SM1  | 129 +/− 2  | 6.3 | 131 +/− 4  | 101 | 12.1 | 293-T |
| pCB2_A1A2_SM1 | 167 +/− 19 |     | 151 +/− 17 | 90  |      |       |
| pCB_A1A2_SM1  | 89 +/− 14  | 6.6 | 28 +/− 2   | 31  | 10.4 | 293-EBNA |
| pCB2_A1A2_SM1 | 131 +/− 4  |     | 54 +/− 3   | 42  |      |       |

As shown in Table 4, we surprisingly found that the levels of expression are maintained significantly better in 293 T cells as compared to 293-EBNA cells. In fact, whereas the expression levels dropped by a factor of 2.5-3 in 293 EBNA cells between production 1 and production 2, the levels remained roughly the same for both constructs in 293-T cells. We additionally observed that the expression levels during production 1 are roughly 30-45% higher in 293-T cells compared to 293-EBNA cells. Hence, the presence of the SV40 large T antigen improves the productivities at early time points and also leads to improved long term expression after extensive propagation of the cells. Moreover, we surprisingly found that constructs which drive the EBNA-1 expression from the EF1α promoter (pCB2_A1A2_SM1) showed significantly higher antibody expression levels in both 293T and 293EBNA cells as compared to constructs expressing EBNA-1 from the EBV derived EBNA-1 promoter (pCB_A1A2_SM 1).

Example 9

Constructs Comprising Replication Elements from MHV68

Generation of Constructs

Several constructs containing replication elements form the mouse herpes virus 68 (MHV68) are generated and tested in different cell lines. First, the origin of replication of MHV68 and the replication initiation factor LANA1 are cloned from viral episomes. Briefly, episomal DNA is extracted from MHV 68 infected BHK cells by Hirt extraction (Hirt, B., J. Mol. Biol. 1967, 26:365-369) and used as a template to amplify the origin of replication and the replication initiation factor by PCR. The different PCR primers are generated based on the published DNA sequence of MHV68 (Accession number: U97553). In order to map the minimal cis sequence required for episomal replication fragments of different length containing the terminal repeats in the centre are amplified with primers M1-M8 (SEQ ID NO: 25-34). The LANA1 open reading frame is amplified with the primer pair M9 and M10. All PCR amplifications are performed using standard techniques. The primers used, the names of the PCR fragments and the size of the PCR fragments are shown in table 5.

TABLE 5

Primers and PCR fragments

| No. | Primers | Fragment Name | Fragment Size |
|---|---|---|---|
| 1 | M1/M2  | MHVoriA | 9.2 kb  |
| 2 | M3/M4  | MHVoriB | 7.2 kb  |
| 3 | M5/M6  | MHVoriC | 4.2 kb  |
| 4 | M7/M8  | MHVoriD | 1.2 kb  |
| 5 | M9/M10 | LANA1   | 0.97 kb |

Sequences of the Primers M1-M8:

```
                                        (SEQ ID NO: 25)
M1: TGGCGGGGGCGGTTCCATCTGCAGTTG (SEQ ID NO: 26)
M2: TTTCTTTAAACACGCCTGGAAGGAGAAGC (SEQ ID NO: 27)
M3: TTCAATCTCTGCACCACGGCGACCGCTC (SEQ ID NO: 28)
M4: TTCAACATTAACATCAGATGAACCAAAATA (SEQ ID NO: 29)
M5: GTCCGCCAAGGGGCTATCCTCCAGGGATC (SEQ ID NO: 30)
M6: TACATAAGCGGCTGTGCGCTGCTTGAAAG (SEQ ID NO: 31)
M7: CAGGCACCAACAGCGGCCCAGGGCTCGGG (SEQ ID NO: 32)
M8: TGGTCGGCCGCCCTGAACTCCTGAACCC (SEQ ID NO: 33)
M9: AAAGGATCCACCATGCCCACATCCCCACCGACTA (SEQ ID NO: 34)
M10: TTCTCGAGCTTTATGTCTGAGACCCTTGTCCC
```

The different PCR fragments (Table 5, number 1-4) containing the terminal repeat and the origin of replication of MHV68 are then either cloned into pCB_A1A2_SM1 which had previously been digested with BamHI and blunt ended with Klenow polymerase, into pCB_A1A2_SM2 which had previously been digested with BamHI and blunt ended with klenow polymerase or into pCB_A1A2_SM2, which had previously been digested with BamHI/BlnI and blunt ended with Klenow polymerase. The vectors backbone, the inserts used and the resulting construct names are depicted in Table 6. As shown in the table, for all the inserts, both, the sense (SE) and antisense (AS) orientation are generated. Whereas constructs 9-24 contain the antibody expression cassette, S/MAR at position 1 or position 2, OriP, EBNA1, SV40 promoter and SV 40 origin of replication as well as MHV 68 origin of replication, the constructs 1-8 do not contain OriP and EBNA1.

TABLE 6

MHV expression constructs

| No.: | Vector | Insert (PCR fragment) | Name |
|---|---|---|---|
| 1 | pCB_A1A2_SM2 | MHVoriA | pMHV_A-SE_SM |
| 2 | | MHVoriA | pMHV_A-AS_SM |
| 3 | | MHVoriB | pMHV_B-SE_SM |
| 4 | | MHVoriB | pMHV_B-AS_SM |
| 5 | | MHVoriC | pMHV_C-SE_SM |
| 6 | | MHVoriC | pMHV_C-AS_SM |
| 7 | | MHVoriD | pMHV_D-SE_SM |
| 8 | | MHVoriD | pMHV_D-AS_SM |
| 9 | pCB_A1A2_SM1 | MHVoriA | pMHV_A-SE_SM1 |
| 10 | | MHVoriA | pMHV_A-AS_SM1 |
| 11 | | MHVoriB | pMHV_B-SE_SM1 |
| 12 | | MHVoriB | pMHV_B-AS_SM1 |
| 13 | | MHVoriC | pMHV_C-SE_SM1 |
| 14 | | MHVoriC | pMHV_C-AS_SM1 |
| 15 | | MHVoriD | pMHV_D-SE_SM1 |
| 16 | | MHVoriD | pMHV_D-AS_SM1 |
| 17 | pCB_A1A2_SM2 | MHVoriA | pMHV_A-SE_SM2 |
| 18 | | MHVoriA | pMHV_A-AS_SM2 |
| 19 | | MHVoriB | pMHV_B-SE_SM2 |
| 20 | | MHVoriB | pMHV_B-AS_SM2 |
| 21 | | MHVoriC | pMHV_C-SE_SM2 |
| 22 | | MHVoriC | pMHV_C-AS_SM2 |
| 23 | | MHVoriD | pMHV_D-SE_SM2 |
| 24 | | MHVoriD | pMHV_D-AS_SM2 |

In order to be able to generate cell lines over expressing the replication initiation factor LANA1, the PCR fragment containing the LANA1 open reading frame is cloned into the lentiviral vector pLenti 6 (Invitrogen). Briefly, the PCR fragment LANA1 (Table 5, number 5) is digested with BamH/XhoI and cloned into the BamHI/XhoI sites of pLenti6 (Invitrogen) and the resulting construct is named pLE_LANA. Then, recombinant lentiviruses encoding LANA1 are generated according to the manufacturer's instruction (Invitrogen). Similarly an expression construct which encodes the SV40 large T antigen is generated. Briefly, the large T open reading frame is amplified by RT-PCR from 293T cells using primers LI53 (SEQ ID NO: 35) and LI54 (SEQ ID NO: 36). The PCR fragment is then digested with BamHI/XhoI and cloned into pcDNA3.1(−) (Invitrogen) digested with BamHI/XhoI. The resulting construct is named pcDNA_T.

The sequences of the primers LI53 and LI54:

(SEQ ID NO: 35)
LI53: CTAGAGGATCCGCCACCATGGATAAAGTTTTAAACAG (SEQ ID NO: 36)
LI54: CGACTAGACTCGAGTTTTATGTTTCAGGTTCAGGG

Generation of Cell Lines and Cell Populations

Different cell lines or cell populations expressing one or more different replication initiation factors are then generated as follows. To generate 293T, 293 and CHO cells that express the LANA1 protein, 293T, 293 and CHO cells are infected with pLN_LANA viruses and selected with blasticidin according to the manufacturers recommendation (Invitrogen). Stable cell population expressing the LANA protein are named 293T_LANA, 293_LANA and CHO_LANA. To generate CHO cells which either express the SV40 large T antigen alone or together with the LANA protein, CHO cells are transfected with pcDNA_T using lipofecatmine 2000 according to the manufacturers recommendation. One day after transfection the cell are passaged in the presence of G414. 4-7 days later all the non transfected cells have died and the surviving cells are single cell sorted into 96 well plates using a flow cytometer. Individual cell clones are then expanded and a fixed amount of cells is lysed in SDS-PAGE loading buffer and separated on polyacrylamid gels. Gels are then blotted onto nitrocellulose and large T expression is monitored with a large T specific antibody. A clone which expresses high levels of large T is then selected for further experiments. This new cell line is named CHO_T. Then a cell population which expresses large T and LANA is generated by infection of CHO-T cells with pLN_LANA as described above.

Whereas 293T and CHO_T cells express the SV40 large T, 293T_LANA and CHO_T_LANA cells express both the SV40 large T and MHV68 LANA1 protein.

Testing of Constructs

All the different constructs shown in Table 6 (number 1-24) are then tested for their ability to replicate in different cell lines and cell populations Briefly, 293T, 293_LANA, 293EBNA, 293T_LANA, CHO, CHO-T, CHO_LANA, CHO_T_LANA cells are transfected with constructs 1-24 shown in Table 6 using lipofectamine 2000 according to the manufacturer's recommendation. One day after transfection cells are passaged under selective conditions in the presence of puromycin (293 derived cells 1 µg/ml, CHO derived cells 10 µg/ml). 2 to 3 days later all the non-transfected cells are dead and the resistant cells are subjected to different tests as described below.

For further characterisation of the different new constructs, the resistant cells are passaged under selective pressure in regular intervals over several months and different parameters are evaluated. Particularly expression of the gene of interest, episome copy number and proliferation rates at different time points are determined. To measure the productivities of the different constructs a defined amount of cells is seeded as described in Example 3 (293 derived cells) or as described in Example 5 (CHO derived cells). To asses the production levels an antibody specific ELISA is performed as outlined in Example 2. To asses the proliferation rates, at each splitting the cells are counted and defined amounts of cells are passaged to new plates as described briefly in Example 4. Finally to monitor the maintenance and copy number of the episome a procedure described previously is used (Wu et al.; Journal of virology, 76, 5, 2480-2490). Briefly, $5 \times 10^6$ cells from each plate are harvested at each time point and lysed by the method of Hirt (Hirt, B., J. Mol. Biol. 1967, 26:365-369). Low-molecular weight DNA is then isolated as described by Ceccarelli and Frappier (Ceccarelli, D. F. J., and L. Frappier, J. Virol. 2000, 74:4939-4948), digested with XhoI and DpnI, separated by agarose gel electrophoresis, Southern blotted, and probed with $^{32}$P-labeled probes specific for the vectors. Linearized plasmid bands are visualized by autoradiography and quantified by phosphor-imager analysis using ImageQuant software (Molecular Dynamics).

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A nucleic acid molecule comprising:
   (a) at least one gene of interest;
   (b) at least one scaffold/matrix attached region (S/MAR), wherein said at least one S/MAR originates from the 5' region of the interferon beta gene (SEQ ID NO: 3);
   (c) at least one origin of replication (ORI); and
   (d) at least one nucleic acid sequence encoding a replication initiation factor capable of recognizing said at least one origin of replication;
   wherein the first of said at least one origin of replication is OriP, and wherein the first of said at least one nucleic acid sequence encoding a replication initiation factor comprises the coding sequence for the EBNA-1 protein.

2. The nucleic acid molecule of claim 1, wherein the first of said at least one gene of interest (A1), the first of said at least one scaffold/matrix attached region (S/MAR) (B1), the first of said at least one origin of replication (ORI) (C1), and the first of said at least one nucleic acid sequence encoding a replication initiation factor (D1) are positioned on said nucleic acid molecule in a consecutive order selected from
   (a) the consecutive order of A1-B1-C1-D1; and
   (b) the consecutive order of A1-C1-D1-B1.

3. The nucleic acid molecule of claim 2, wherein said consecutive order is A1-B1-C1-D1.

4. The nucleic acid molecule of claim 3, wherein said first gene of interest (A1) comprises a promoter (prom) and a polyadenylation signal sequence (pa), and wherein said consecutive order is promA1pa-B1-C1-D1.

5. The nucleic acid molecule of claim 4, wherein the distance between said first S/MAR element (B1) and said polyadenylation signal sequence (pa) of said first gene of interest (A1) is less than 500 bp.

6. The nucleic acid molecule of claim 3, wherein the distance between said first S/MAR element (B1) and said first origin of replication (ORI) (C1) is less than 1000 bp.

7. The nucleic acid molecule of claim 4, wherein said first nucleic acid sequence encoding a replication initiation factor (D1) comprises a promoter (prom) and a polyadenylation signal sequence (pa), and wherein said consecutive order is promA1pa-B1-C1-paD1 prom.

8. The nucleic acid molecule of claim 2, wherein said consecutive order is A1-C1-D1-B1.

9. The nucleic acid molecule of claim 8, wherein said first nucleic acid sequence encoding a replication initiation factor (D1) comprises a promoter (prom) and a polyadenylation signal sequence (pa), and wherein said consecutive order is A1-C1-paD1prom-B1.

10. The nucleic acid molecule of claim 9, wherein the distance between said first S/MAR element (B1) and said promoter of said first nucleic acid sequence encoding a replication initiation factor (D1) is less than 500.

11. The nucleic acid molecule of claim 10, wherein the distance between said first S/MAR element (B1) and said first origin of replication (C1) is less than 8000 bp.

12. The nucleic acid molecule of claim 9, wherein said first gene of interest (A1) comprises a promoter (prom) and a polyadenylation signal sequence (pa), and wherein said consecutive order is promA1pa-C1-paD1prom-B1.

13. The nucleic acid molecule of claim 1, wherein said nucleic acid molecule is an episomally replicating expression vector.

14. The nucleic acid molecule of claim 2, wherein said nucleic acid molecule comprises at least a first gene of interest (A1) and a second gene of interest (A2), and wherein said consecutive order is selected from
   (a) the consecutive order of A1-A2-B1-C1-D1; and
   (b) the consecutive order of A1-A2-C1-D1-B1.

15. The nucleic acid molecule of claim 14, wherein said first gene of interest and said second gene of interest are selected from
   (a) a gene encoding the light chain of an antibody; and
   (b) a gene encoding the heavy chain of an antibody.

16. The nucleic acid molecule of claim 14, wherein said first gene of interest (A1) comprises a nucleic acid sequence encoding the light chain of an antibody and wherein said second gene of interest (A2) comprises a nucleic acid sequence encoding the heavy chain of said antibody.

17. The nucleic acid molecule of claim 14, wherein said consecutive order is A1-A2-B1-C1-D1.

18. The nucleic acid molecule of claim 17, wherein said first gene of interest (A1) comprises a promoter (prom) and a polyadenylation signal sequence (pa), wherein said second gene of interest (A2) comprises a promoter (prom) and a polyadenylation signal sequence (pa), and wherein said consecutive order is promA1pa-promA2pa-B1-C1-D1.

19. The nucleic acid molecule of claim 18, wherein the distance between said first S/MAR element (B1) and said polyadenylation signal sequence (pa) of said second gene of interest (A2) is less than 500 bp.

20. The nucleic acid molecule of claim 18, wherein the distance between said first S/MAR element (B1) and said first origin of replication (ORI) (C1) is less than 1000 bp.

21. The nucleic acid molecule of claim 18, wherein said first nucleic acid sequence encoding a replication initiation factor (D1) comprises a promoter (prom) and a polyadenylation signal sequence (pa), and wherein said consecutive order is promA1pa-promA2pa-B1-C1-paD1prom.

22. The nucleic acid molecule of claim 14, wherein said consecutive order is A1-A2-C1-D1-B1.

23. The nucleic acid molecule of claim 22, wherein said first nucleic acid sequence encoding a replication initiation factor (D1) comprises a promoter (prom) and a polyadenylation signal sequence (pa), and wherein said consecutive order is A1-A2-C1-paD1prom-B1.

24. The nucleic acid molecule of claim 23, wherein the distance between said first S/MAR element (B1) and the promoter of said first nucleic acid seciuence encoding a replication initiation factor (D1) is less than 500 bp.

25. The nucleic acid molecule of claim 24, wherein the distance between said first S/MAR element (B1) and said first origin of replication (C1) is less than 8000 bp.

26. The nucleic acid molecule of claim 23, wherein said first gene of interest (A1) comprises a promoter (prom) and a polyadenylation signal sequence (pa), wherein said second gene of interest (A2) comprises a promoter (prom) and a polyadenylation signal sequence (pa), and wherein said consecutive order is promA1pa-promA2pa-C1-paD1prom-B1.

27. The nucleic acid molecule of claim 1, wherein the second and/or third of said at least one origin of replication, if present, is derived from a DNA virus.

28. The nucleic acid molecule of claim 1, wherein the second and/or third of said at least one origin of replication, if present, is derived from a DNA virus selected from the group consisting of Herpesvirus, Papovavirus, Papillomavirus, Polyomavirus, Adenovirus, and Hepadnavirus.

29. The nucleic acid molecule of claim 1, wherein said at least one origin of replication comprises at least one first and at least one second origin of replication.

30. The nucleic acid molecule of claim 29, wherein said second origin of replication is SV40 ori.

31. The nucleic acid molecule of claim 1, wherein said at least one nucleic acid sequence encoding a replication initiation factor comprises at least one first and at least one second nucleic acid sequence each encoding a replication initiation factor.

32. The nucleic acid molecule of claim 1, wherein the second and/or third of said at least one nucleic acid sequence encoding a replication initiation factor, if present, is derived from a DNA virus.

33. The nucleic acid molecule of claim 1, wherein the second and/or third of said at least one nucleic acid sequence encoding a replication initiation factor, if present, is derived from a DNA virus selected from the group consisting of Herpesvirus, Papovavirus, Papillomavirus, Polyomavirus, Adenovirus, and Hepadnavirus.

34. The nucleic acid molecule of claim 31, wherein said second nucleic acid sequence encoding a replication initiation factor is a nucleic acid sequence comprising the coding sequence for the SV40 large T-antigen.

35. The nucleic acid molecule of claim 1, further comprising at least one selection marker.

36. The nucleic acid molecule of claim 35, wherein said selection marker confers resistance to puromycin.

37. The nucleic acid molecule of claim 1, wherein said nucleic acid molecule further comprises a promoter selected from the group of promoters consisting of a constitutive or engineered hybrid promoter, cell cycle-specific promoter, tissue-specific promoter, metabolically regulated promoter, and an inducible promoter.

38. The nucleic acid molecule of claim 37, wherein said promoter is a CMV promoter, an EF1α promoter or a SRα promoter.

39. The nucleic acid molecule of claim 1, wherein said nucleic acid molecule further comprises an activator sequence selected from the group consisting of a constitutive activator, cell cycle-specific activator, tissue-specific activator, metabolically regulated activator, and an inducible activator.

40. An expression system comprising at least one nucleic acid molecule of claim 1.

41. An expression system comprising
   (a) at least one gene of interest;
   (b) at least one scaffold/matrix attached region (S/MAR), wherein said at least one S/MAR originates from the 5' region of the interferon beta gene (SEQ ID NO: 3);
   (c) at least one origin of replication (ORI); and
   (d) at least one nucleic acid sequence encoding a replication initiation factor capable of recognizing said at least one origin of replication;

wherein the first of said at least one origin of replication is OriP, and wherein the first of said at least one nucleic acid sequence encoding a replication initiation factor comprises the coding sequence for the EBNA-1 protein.

42. The expression system of claim 41, wherein said at least one gene of interest, said at least one S/MAR, said at least one origin of replication (ORI), and said at least one nucleic acid sequence encoding a replication initiation factor are all present on a single nucleic acid molecule.

43. The expression system of claim 41 wherein said at least one gene of interest, said at least one S/MAR, and said at least one origin of replication (ORI) are present on a first nucleic acid molecule, and wherein said at least one nucleic acid sequence encoding a replication initiation factor is present on at least one separate nucleic acid molecule.

44. The expression system of claim 43, wherein said at least one nucleic acid sequence encoding a replication initiation factor comprises at least one first and at least one second nucleic acid sequences each encoding a replication initiation factor, and wherein said first and/or second nucleic acid sequence encoding a replication initiation factor is present on a second nucleic acid molecule, or wherein said first nucleic acid sequence encoding a replication initiation factor is present on a second nucleic acid molecule and wherein said second nucleic acid sequence encoding a replication initiation factor is present on a third nucleic acid molecule.

45. A process for the preparation of a nucleic acid molecule of claim 1, comprising inserting at least one scaffold/matrix attached regions (S/MAR) into a nucleic acid construct comprising at least one origin of replication (ORI), at least one gene of interest, and at least one nucleic acid sequence encoding a replication initiation factor;
wherein said at least one S/MAR originates from the 5' region of the interferon beta gene (SEQ ID NO: 3);
wherein the first of said at least one origin of replication is OriP; and wherein the first of said at least one nucleic acid sequence encoding a replication initiation factor comprises the coding seciuence for the EBNA-1 protein.

46. The process of claim 45, wherein at least one gene mediating antibiotic resistance is further inserted into said nucleic acid molecule.

47. A method of making a recombinant host cell comprising introducing the nucleic acid molecule of claim 1 or introducing the expression system of claim 41 into a host cell.

48. The method of claim 47, wherein said nucleic acid molecule or said expression system is introduced by way of transfection.

49. A recombinant host cell produced by the method of claim 47.

50. A recombinant host cell comprising at least one nucleic acid molecule of claim 1.

51. A recombinant host cell comprising
(a) at least one gene of interest;
(b) at least one scaffold/matrix attached region (S/MAR), wherein said at least one S/MAR originates from the 5' region of the interferon beta gene (SEQ ID NO: 3);
(c) at least one origin of replication (ORI); and
(d) at least one nucleic acid sequence encoding a replication initiation factor capable of recognizing said at least one origin of replication;
wherein the first of said at least one origin of replication is OriP, and wherein the first of said at least one nucleic acid sequence encoding a replication initiation factor comprises the coding sequence for the EBNA-1 protein.

52. The recombinant host cell of claim 51, wherein said at least one gene of interest, said at least one S/MAR, said at least one origin of replication (ORI), and said at least one nucleic acid sequence encoding a replication initiation factor are all present on a single nucleic acid molecule.

53. The recombinant host cell of claim 51 wherein said at least one gene of interest, said at least one S/MAR, and said at least one origin of replication (ORI) are present on a first nucleic acid molecule, and wherein said at least one nucleic acid sequence encoding a replication initiation factor is present on a second nucleic acid molecule.

54. The recombinant host cell of claim 51, wherein the first and/or the second and/or the third of said at least one nucleic acid sequence encoding a replication initiation factor, if present, is stably integrated into the genome of said host cell.

55. The recombinant host cell of claim 51, wherein said host cell comprises more than one copy of said at least one nucleic acid sequence encoding a replication initiation factor.

56. The recombinant host cell of claim 55, wherein at least one copy of said at least one nucleic acid sequence encoding a replication initiation factor is stably integrated into the genome of said host cell.

57. The recombinant host cell of claim 51, further comprising a selection marker.

58. The recombinant host cell of claim 57, wherein said selection marker is glutamine synthetase.

59. The recombinant host cell of claim 51, wherein the second and/or the third of said at least one origin of replication, if present, is derived from a DNA virus.

60. The recombinant host cell of claim 51, wherein said at least one origin of replication comprises at least one first and at least one second origin of replication.

61. The recombinant host cell of claim 60, wherein said second origin of replication is SV40 ori.

62. The recombinant host cell of claim 51, wherein the second and/or third of said at least one nucleic acid sequence encoding a replication initiation factor, if present, is derived from a DNA virus.

63. The recombinant host cell of claim 51, wherein said at least one nucleic acid sequence encoding a replication initiation factor comprises at least one first and at least one second nucleic acid sequences each encoding a replication initiation factor.

64. The recombinant host cell of claim 63, wherein said second nucleic acid sequence encoding a replication initiation factor comprises the coding sequence for the SV40 large T-antigen.

65. The recombinant host cell of claim 64, wherein said second nucleic acid sequence encoding a replication initiation factor is stably integrated into the genome of said recombinant host cell.

66. The recombinant host cell of claim 51, further comprising a nucleotide element capable of promoting the replication of the first and/or the second and/or the third of said at least one origin of replication.

67. The recombinant host cell of claim 51, wherein said at least one replication initiation factor comprises at least one first, at least one second, and at least one third nucleic acid sequence each encoding a replication initiation factor.

68. The recombinant host cell of claim 67, wherein said second nucleic acid sequence encoding a replication initiation factor comprises the coding sequence for the SV40 large T-antigen, and wherein said third nucleic acid sequence encoding a replication initiation factor is derived from a herpesvirus.

69. The recombinant host cell of claim 68, wherein said second and/or said third of said at least one nucleic acid sequence encoding a replication initiation factor, if present, is stably integrated into the genome of said recombinant host cell.

70. The recombinant host cell of claim 51, wherein said recombinant host cell is a mammalian cell.

71. The recombinant host cell of claim 70, wherein said mammalian cell is selected from the group consisting of a human cell, a primate cell and a rodent cell.

72. The recombinant host cell of claim 70, wherein said mammalian cell is a human cell selected from the group consisting of a 293 HER cell, a 293 EBNA cell, a 293 T cell and a 293 derived cell.

73. The recombinant host cell of claim 70, wherein said mammalian cell is a rodent cell selected from the group consisting of a CHO cell, a CHOK1 cell and a CHO derived cell.

74. A recombinant host cell comprising at least one nucleic acid molecule of claim 3.

75. The recombinant host cell of claim 74, wherein said host cell is a human cell.

76. The recombinant host cell of claim 74, wherein said host cell is a 293 EBNA cell.

77. A recombinant host cell comprising the nucleic acid molecule of claim 22.

78. The recombinant host cell of claim 77, wherein said host cell is a rodent cell.

79. The recombinant host cell of claim 77, wherein said host cell is a CHO, CHOK1 or CHO derived cell.

80. A method for producing a polypeptide or untranslated RNA molecule, said method comprising:
   (a) introducing the nucleic acid molecule of claim 1 into a host cell to produce a recombinant host cell; and
   (b) culturing said recombinant host cell under conditions suitable for expression of said polypeptide or untranslated RNA molecule.

81. The method of claim 80, wherein said host cell is a 293 EBNA cell.

82. The method of claim 80, wherein said host cell is a CHOK1 cell.

83. A method for producing a polypeptide or untranslated RNA molecule, said method comprising:
   (a) introducing the expression system of claim 41 into a host cell to produce a recombinant host cell; and
   (b) culturing said recombinant host cell under conditions suitable for expression of said polypeptide or untranslated RNA molecule.

84. A kit comprising the nucleic acid molecule of claim 1 or the recombinant host cell of claim 51, and a transfection system comprising a component selected from the group consisting of a lipid, a polymer, a peptide, and a porphyrin.

85. The nucleic acid molecule of claim 35, wherein said selection marker is glutamine synthetase, or wherein said selection marker confers resistance to an antibiotic selected from the group of antibiotics consisting of puromycin, kanamycin, geneticin, gentamicin, ampicillin, tetracycline, streptomycin, spectinomycin, nalidixic acid, rifampicin, chloramphenicol, and zeocin.

86. The expression system of claim 43, wherein said at least one nucleic acid seciuence encoding a replication initiation factor is present on at least one separate second nucleic acid molecule.

87. The recombinant host cell of claim 55, wherein said host cell comprises more than one copy of the first and/or the second and/or the third of said at least one nucleic acid sequence encoding a replication initiation factor.

88. The recombinant host cell of claim 56, wherein the first and/or the second and/or the third copy of said at least one nucleic acid seciuence encoding a replication initiation factor, if present, is stably integrated into the genome of said host cell.

89. The recombinant host cell of claim 59, wherein the second and/or third of said at least one origin of replication is derived from a DNA virus selected from the group consisting of Herpesvirus, Papovavirus, Papillomavirus, Polyomavirus, Adenovirus, and Hepadnavirus.

90. The recombinant host cell of claim 62, wherein the second and/or third of said at least one nucleic acid sequence encoding a replication initiation factor, if present, is derived from a DNA virus selected from the group consisting of Herpesvirus, Papovavirus, Papillomavirus, Polyomavirus, Adenovirus, and Hepadnavirus.

91. The recombinant host cell of claim 68, wherein said second nucleic acid seciuence encoding a replication initiation factor comprises the coding sequence for the SV40 large T-antigen and wherein said third nucleic acid sequence encoding a replication initiation factor is derived from a herpesvirus.

92. The recombinant host cell of claim 91, wherein said third nucleic acid sequence encoding a replication initiation factor is derived from Murine Gammaherpesvirus 68 (MHV 68).

93. The recombinant host cell of claim 92, wherein said third nucleic acid sequence encoding a comprises the coding sequence for LANA.

94. A method for producing a polypeptide or untranslated RNA molecule, said method comprising:
   (a) introducing the nucleic acid molecule of claim 3 into a host cell to produce a recombinant host cell; and
   (b) culturing said recombinant host cell under conditions suitable for expression of said polypeptide or untranslated RNA molecule.

95. The method of claim 94, wherein said host cell is a 293 EBNA cell.

96. A method for producing a polypeptide or untranslated RNA molecule, said method comprising:
   (a) introducing the nucleic acid molecule of claim 22 into a host cell to produce a recombinant host cell; and
   (b) culturing said recombinant host cell under conditions suitable for expression of said polypeptide or untranslated RNA molecule.

97. The method of claim 96, wherein said host cell is a CHOK1 cell.

98. The nucleic acid molecule of claim 14, wherein said first gene of interest and said second gene of interest are selected from:
   (a) a gene encoding the light chain of an antibody; and
   (b) a gene encoding the heavy chain of said antibody.

* * * * *

SEQUENCE LISTING

<160> NUMBER OF SEQ ID NOS: 36

<210> SEQ ID NO 1
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 1
atagataaac gattagaatt cagcaag                                        27

<210> SEQ ID NO 2
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 2
gatgggttca ctagtgaatt ctatcaa                                        27

<210> SEQ ID NO 3
<211> LENGTH: 2200
<212> TYPE: DNA
<213> ORGANISM: homo sapiens

<400> SEQUENCE: 3
aattcagcaa ggtcgccacg cacaagatca atattaacaa tcagtcatct ctctttagca    60 ataaaaggt gaaaattac attttaaaaa tgacaccata gacgatgtat gaaaataatc     120
tacttggaaa taaatctagg caagaagtg caagactgtt acccagaaaa cttacaaatt    180
gtaaatgaga ggttagtgaa gatttaaatg aatgaagatc taaataaact tataaattgt    240
gagagaaatt aatgaatgtc taagttaatg cagaaacgga gagacatact atattcatga    300
actaaaagac ttaatattgt gaaggtatac tttcttttca cataaatttg tagtcaatat    360 gttcaccca aaaaagctgt ttgttaactt gtcaacctca tttcaaaatg tatatagaaa    420
gcccaaagac aataacaaaa atattcttgt agaacaaaat gggaaagaat gttccactaa    480
atatcaagat ttagagcaaa gcatgagatg tgtgggata gacagtgagg ctgataaaat     540
agagtagagc tcagaaacag acccattgat atatgtaagt gacctatgaa aaaaatatgg    600
cattttacaa tgggaaaatg atgatctttt tcttttttag aaaaacaggg aaatatattt    660
atatgtaaaa aataaaaggg aacccatatg tcataccata cacacaaaaa aattccagtg    720
aattataagt ctaaatggag aaggcaaaac tttaaatctt ttagaaaata atatagaagc    780
atgccatcat gacttcagtg tagagaaaaa tttcttatga ctcaaagtcc taaccacaaa    840
gaaaagattg ttaattagat tgcatgaata ttaagactta ttttttaaaat taaaaaacca    900

| | | | | |
|---|---|---|---|---|
| ttaagaaaag | tcaggccata | gaatgacaga | aaatatttgc | aacacccccag taaagagaat | 960 |
| tgtaatatgc | agattataaa | aagaagtctt | acaaatcagt | aaaaaataaa actagacaaa | 1020 |
| aatttgaaca | gatgaaagag | aaactctaaa | taatcattac | acatgagaaa ctcaatctca | 1080 |
| gaaatcagag | aactatcatt | gcatatacac | taaattagag | aaatattaaa aggctaagta | 1140 |
| acatctgtgg | caatattgat | ggtatataac | cttgatatga | tgtgatgaga acagtacttt | 1200 |
| accccatggg | cttcctcccc | aaaccttac | cccagtataa | atcatgacaa atatacttta | 1260 |
| aaaaccatta | ccctatatct | aaccagtact | cctcaaaact | gtcaaggtca tcaaaaataa | 1320 |
| gaaaagtctg | aggaactgtc | aaaactaaga | ggaacccaag | gagacatgag aattatatgt | 1380 |
| aatgtggcat | tctgaatgag | atcccagaac | agaaaaagaa | cagtagctaa aaaactaatg | 1440 |
| aaatataaat | aaagtttgaa | ctttagtttt | ttttaaaaaa | gagtagcatt aacacggcaa | 1500 |
| agtcattttc | atattttct | tgaacattaa | gtacaagtct | ataattaaaa atttttaaa | 1560 |
| tgtagtctgg | aacattgcca | gaaacagaag | tacagcagct | atctgtgctg tcgcctaact | 1620 |
| atccatagct | gattggtcta | aaatgagata | catcaacgct | cctccatgtt ttttgttttc | 1680 |
| ttttaaatg | aaaaacttta | tttttaaga | ggagtttcag | gttcatagca aaattgagag | 1740 |
| gaaggtacat | tcaagctgag | gaagttttcc | tctattccta | gtttactgag agattgcatc | 1800 |
| atgaatgggt | gttaaatttt | gtcaaatgct | ttttctgtgt | ctatcaatat gaccatgtga | 1860 |
| tttcttctt | taacctgttg | atgggacaaa | ttacgttaat | tgattttcaa acgttgaacc | 1920 |
| acccttacat | atctggaata | aattctactt | ggttgtggtg | tatattttt gatacattct | 1980 |
| tggattcttt | ttgctaatat | tttgttgaaa | atgtttgtat | ctttgttcat gagagatatt | 2040 |
| ggtctgttgt | tttcttttct | tgtaatgtca | tttttctagtt | ccggtattaa ggtaatgctg | 2100 |
| gcctagttga | atgatttagg | aagtattccc | tctgcttctg | tcttctgaaa gagattgtag | 2160 |
| aaagttgata | caatttttt | ttctttaaat | atcttgatag | | 2200 |

<210> SEQ ID NO 4
<211> LENGTH: 9482
<212> TYPE: DNA
<213> ORGANISM: Artificial Sequence
<220> FEATURE:
<223> OTHER INFORMATION: vector pCepPU

<400> SEQUENCE: 4

| | | | | |
|---|---|---|---|---|
| ggatcgatcc | ccgccgccgg | acgaactaaa | cctgactacg | gcatctctgc cccttcttcg | 60 |
| cggggcagtg | catgtaatcc | cttcagttgg | ttggtacaac | ttgccaactg ggccctgttc | 120 |
| cacatgtgac | acggggggggg | accaaacaca | aagggggttct | ctgactgtag ttgacatcct | 180 |
| tataaatgga | tgtgcacatt | tgccaacact | gagtggcttt | catcctggag cagactttgc | 240 |
| agtctgtgga | ctgcaacaca | acattgcctt | tatgtgtaac | tcttggctga agctcttaca | 300 |
| ccaatgctgg | gggacatgta | cctcccaggg | gcccaggaag | actacgggag gctacaccaa | 360 |
| cgtcaatcag | aggggcctgt | gtagctaccg | ataagcggac | cctcaagagg gcattagcaa | 420 |
| tagtgtttat | aaggccccct | tgttaaccct | aaacgggtag | catatgcttc ccgggtagta | 480 |
| gtatatacta | tccagactaa | ccctaattca | atagcatatg | ttacccaacg ggaagcatat | 540 |
| gctatcgaat | tagggttagt | aaaagggtcc | taaggaacag | cgatatctcc caccccatga | 600 |
| gctgtcacgg | ttttatttac | atggggtcag | gattccacga | gggtagtgaa ccatttagt | 660 |
| cacaagggca | gtggctgaag | atcaaggagc | gggcagtgaa | ctctcctgaa tcttcgcctg | 720 |

```
cttcttcatt ctccttcgtt tagctaatag aataactgct gagttgtgaa cagtaaggtg      780
tatgtgaggt gctcgaaaac aaggtttcag gtgacgcccc cagaataaaa tttggacggg      840
gggttcagtg gtggcattgt gctatgacac aatataacc ctcacaaacc ccttgggcaa       900
taaatactag tgtaggaatg aaacattctg aatatcttta acaatagaaa tccatggggt      960
ggggacaagc cgtaaagact ggatgtccat ctcacacgaa tttatggcta tgggcaacac     1020
ataatcctag tgcaatatga tactggggtt attaagatgt gtcccaggca gggaccaaga     1080
caggtgaacc atgttgttac actctatttg taacaagggg aaagagagtg gacgccgaca     1140
gcagcggact ccactggttg tctctaacac ccccgaaaat taaacggggc tccacgccaa     1200
tggggcccat aaacaaagac aagtggccac tcttttttt gaaattgtgg agtggggca       1260 cgcgtcagcc cccacacgcc gccctgcggt tttggactgt aaaataaggg tgtaataact     1320
tggctgattg taaccccgct aaccactgcg gtcaaaccac ttgcccacaa aaccactaat     1380
ggcaccccgg ggaatacctg cataagtagg tgggcgggcc aagatagggg cgcgattgct     1440
gcgatctgga ggacaaatta cacacacttg cgcctgagcg ccaagcacag ggttgttggt     1500
cctcatattc acgaggtcgc tgagagcacg gtgggctaat gttgccatgg gtagcatata     1560
ctacccaaat atctggatag catatgctat cctaatctat atctgggtag cataggctat     1620
cctaatctat atctgggtag catatgctat cctaatctat atctgggtag tatatgctat     1680
cctaatttat atctgggtag cataggctat cctaatctat atctgggtag catatgctat     1740
cctaatctat atctgggtag tatatgctat cctaatctgt atccgggtag catatgctat     1800
cctaatagag attagggtag tatatgctat cctaatttat atctgggtag catatactac     1860
ccaaatatct ggatagcata tgctatccta atctatatct gggtagcata tgctatccta     1920
atctatatct gggtagcata ggctatccta atctatatct gggtagcata tgctatccta     1980
atctatatct gggtagtata tgctatccta atttatatct gggtagcata ggctatccta     2040
atctatatct gggtagcata tgctatccta atctatatct gggtagtata tgctatccta     2100
atctgtatcc gggtagcata tgctatcctc atgcatatac agtcagcata tgatacccag     2160
tagtagagtg ggagtgctat cctttgcata tgccgccacc tcccaagggg gcgtgaattt     2220
tcgctgcttg tccttttcct gcatgctggt tgctcccatt cttaggtgaa tttaaggagg     2280
ccaggctaaa gccgtcgcat gtctgattgc tcaccaggta aatgtcgcta atgttttcca     2340
acgcgagaag gtgttgagcg cggagctgag tgacgtgaca acatgggtat gcccaattgc     2400
cccatgttgg gaggacgaaa atggtgacaa gacagatggc cagaaataca ccaacagcac     2460
gcatgatgtc tactggggat ttattcttta gtgcggggga atacacggct tttaatacga     2520
ttgagggcgt ctcctaacaa gttacatcac tcctgccctt cctcaccctc atctccatca     2580
cctccttcat ctccgtcatc tccgtcatca ccctccgcgg cagccccttc caccataggt     2640
ggaaaccagg gaggcaaatc tactccatcg tcaaagctgc acacagtcac cctgatattg     2700
caggtaggag cgggctttgt cataacaagg tccttaatcg catccttcaa aacctcagca     2760
aatatatgag tttgtaaaaa gaccatgaaa taacagacaa tggactccct tagcgggcca     2820
ggttgtgggc cgggtccagg ggccattcca aaggggagac gactcaatgg tgtaagacga     2880
cattgtggaa tagcaagggc agttcctcgc cttaggttgt aaagggaggt cttactacct     2940
ccatatacga acacaccggc gacccaagtt ccttcgtcgg tagtcctttc tacgtgactc     3000
ctagccagga gagctcttaa accttctgca atgttctcaa atttcgggtt ggaacctcct     3060
tgaccacgat gctttccaaa ccaccctcct tttttgcgcc tgcctccatc accctgaccc     3120
```

-continued

```
cggggtccag tgcttgggcc ttctcctggg tcatctgcgg ggccctgctc tatcgctccc    3180
gggggcacgt caggctcacc atctgggcca ccttcttggt ggtattcaaa ataatcggct    3240
tcccctacag ggtggaaaaa tggccttcta cctggagggg gcctgcgcgg tggagacccg    3300
gatgatgatg actgactact gggactcctg ggcctctttt ctccacgtcc acgacctctc    3360
cccctggctc tttcacgact tcccccctg gctctttcac gtcctctacc ccggcggcct    3420
ccactacctc ctcgaccccg gcctccacta cctcctcgac cccggcctcc actgcctcct    3480
cgacccggc ctccacctcc tgctcctgcc cctcctgctc ctgccctcc tcctgctcct     3540
gcccctcctg cccctcctgc tcctgcccct cctgcccctc ctgctcctgc cctcctgcc    3600
cctcctgctc ctgcccctcc tgcccctcct gctcctg cccctcctgc cctcctcct      3660
gctcctgccc ctcctgcccc tcctgctcct gcccctcctg cccctcctgc tcctgcccct    3720
cctgcccctc ctgctcctgc cccctcctgct ctgcccctc ctgctcctgc cctcctgct    3780
cctgcccctc ctgcccctcc tgcccctcct gctcctg cccctcctgc tcctgcccct      3840
cctgcccctc ctgcccctcc tgctcctgcc cctcctctg ctcctgcccc tcctgcccct    3900
cctgcccctc ctcctgctcc tgcccctcct gcccctcctc ctgctcctgc cctcctcct    3960
gctcctgccc ctcctgcccc tcctgcccct cctcctgctc ctgcccctcc tgcccctcct    4020
cctgctcctg cccctcctcc tgctcctgcc cctcctgccc ctcctgcccc tcctcctgct    4080
cctgcccctc ctcctgctcc tgcccctcct gcccctcctg cccctcctgc cctcctcct    4140
gctcctgccc ctcctcctgc tcctgcccct cctgctcctg cccctcccgc tcctgctcct    4200
gctcctgttc caccgtgggt ccctttgcag ccaatgcaac ttggacgttt ttggggtctc    4260
cggacaccat ctctatgtct tggccctgat cctgagccgc ccggggctcc tggtcttccg    4320
cctcctcgtc ctcgtcctct tcccgtcct cgtccatggt tatcaccccc tcttctttga    4380
ggtccactgc cgccggagcc ttctggtcca gatgtgtctc ccttctctcc taggccattt    4440
ccaggtcctg tacctggccc ctcgtcagac atgattcaca ctaaaagaga tcaatagaca    4500
tctttattag acgacgctca gtgaatacag ggagtgcaga ctcctgcccc ctccaacagc    4560
cccccaccc tcatccctt catggtcgct gtcagacaga tccaggtctg aaaattcccc     4620
atcctccgaa ccatcctcgt cctcatcacc aattactcgc agcccggaaa actcccgctg    4680
aacatcctca agatttgcgt cctgagcctc aagccaggcc tcaaattcct cgtccccctt    4740
tttgctggac ggtagggatg gggattctcg ggacccctcc tcttcctctt caaggtcacc    4800
agacagagat gctactgggg caacggaaga aaagctgggt gcggcctgtg aggatcagct    4860
tatcgatgat aagctgtcaa acatgagaat tcttgaagac gaaagggcct cgtgatacgc    4920
ctattttat aggttaatgt catgataata atggtttctt agacgtcagg tggcacttt      4980
cggggaaatg tgcgcggaac ccctatttgt ttattttct aaatacattc aaatatgtat     5040
ccgctcatga gacaataacc ctgataaatg cttcaataat attgaaaaag gaagagtatg    5100
agtattcaac atttccgtgt cgcccttatt cccttttttg cggcattttg ccttcctgtt    5160
tttgctcacc cagaaacgct ggtgaaagta aaagatgctg aagatcagtt gggtgcacga    5220
gtgggttaca tcgaactgga tctcaacagc ggtaagatcc ttgagagttt cgccccgaa    5280
gaacgttttc caatgatgag cacttttaaa gttctgctat gtggcgcggt attatcccgt    5340
gttgacgccg ggcaagagca actcggtcgc cgcatacact attctcagaa tgacttggtt    5400
gagtactcac cagtcacaga aaagcatctt acggatggca tgacagtaag agaattatgc    5460
```

-continued

```
agtgctgcca taaccatgag tgataacact gcggccaact tacttctgac aacgatcgga   5520
ggaccgaagg agctaaccgc ttttttgcac aacatggggg atcatgtaac tcgccttgat   5580
cgttgggaac cggagctgaa tgaagccata ccaaacgacg agcgtgacac cacgatgcct   5640
gcagcaatgg caacaacgtt gcgcaaacta ttaactggcg aactacttac tctagcttcc   5700
cggcaacaat taatagactg gatggaggcg gataaagttg caggaccact tctgcgctcg   5760
gcccttccgg ctggctggtt tattgctgat aaatctggag ccgtgagcg tgggtctcgc    5820
ggtatcattg cagcactggg gccagatggt aagccctccc gtatcgtagt tatctacacg   5880
acggggagtc aggcaactat ggatgaacga aatagacaga tcgctgagat aggtgcctca   5940
ctgattaagc attggtaact gtcagaccaa gtttactcat atatacttta gattgattta   6000
aaacttcatt tttaatttaa aaggatctag gtgaagatcc ttttgataa tctcatgacc    6060
aaaatccctt aacgtgagtt tcgttccac tgagcgtcag accccgtaga aagatcaaa     6120
ggatcttctt gagatccttt ttttctgcgc gtaatctgct gcttgcaaac aaaaaaacca   6180
ccgctaccag cggtggtttg tttgccggat caagagctac caactctttt tccgaaggta   6240
actggcttca gcagagcgca gataccaaat actgtccttc tagtgtagcc gtagttaggc   6300
caccacttca agaactctgt agcaccgcct acatacctcg ctctgctaat cctgttacca   6360
gtggctgctg ccagtggcga taagtcgtgt cttaccgggt tggactcaag acgatagtta   6420
ccggataagg cgcagcggtc gggctgaacg gggggttcgt gcacacagcc cagcttggag   6480
cgaacgacct acaccgaact gagataccta cagcgtgagc tatgagaaag cgccacgctt   6540
cccgaaggga gaaaggcgga caggtatccg gtaagcggca gggtcggaac aggagagcgc   6600
acgagggagc ttccagggg aaacgcctgg tatctttata gtcctgtcgg gtttcgccac    6660
ctctgacttg agcgtcgatt tttgtgatgc tcgtcagggg ggcggagcct atggaaaaac   6720
gccagcaacg cggccttttt acggttcctg gccttttgct gcgccgcgtg cggctgctgg   6780
agatggcgga cgcgatggat atgttctgcc aagggttggt ttgcgcattc acagttctcc   6840
gcaagaattg attggctcca attcttggag tggtgaatcc gttagcgagg ccatccagcc   6900
tcgcgtcgaa ctagatgatc cgctgtggaa tgtgtgtcag ttagggtgtg gaaagtcccc   6960
aggctcccca gcaggcagaa gtatgcaaag catgcatctc aattagtcag caaccaggtg   7020
tggaaagtcc ccaggctccc cagcaggcag aagtatgcaa agcatgcatc tcaattagtc   7080
agcaaccata gtcccgcccc taactccgcc catcccgccc ctaactccgc ccagttccgc   7140
ccattctccg ccccatggct gactaatttt ttttatttat gcagaggccg aggccgcctc   7200
ggcctctgag ctattccaga agtagtgagg aggcttttt ggagggtgac cgccacgagg    7260
tgccgccacc atccctgac ccacgcccct gaccctcac aaggagacga ccttccatga    7320
ccgagtacaa gcccacggtg cgcctcgcca cccgcgacga cgtccccgg gccgtacgca    7380
ccctcgccgc cgcgttcgcc gactacccg ccacgcgcca caccgtcgac cccgaccgcc    7440
acatcgaacg cgtcaccgag ctgcaagaac tcttcctcac gcgcgtcggg ctcgacatcg   7500
gcaaggtgtg gtcgcggac gacggcgccg cggtggcggt ctggaccacg ccggagagcg    7560
tcgaagcggg ggcggtgttc gccgagatcg gcccgcgcat ggccgagttg agcggttccc   7620
ggctggccgc gcagcaacag atggaaggcc tcctggcgcc gcaccggccc aaggagcccg   7680
cgtggttcct ggccaccgtc ggcgtctcgc ccgaccacca gggcaagggt ctgggcagcg   7740
ccgtcgtgct cccccggagtg gaggcggccg agcgcgccgg ggtgcccgcc ttcctggaga   7800
cctccgcgcc ccgcaaccte cccttctacg agcggctcgg cttcaccgtc accgccgacg   7860
```

```
tcgagtgccc gaaggaccgc gcgacctggt gcatgacccg caagcccggt gcctgacgcc      7920
cgccccacga cccgcagcgc ccgaccgaaa ggagcgcacg acccggtccg acggcggccc      7980
acgggtccca gggggtcga cctcgaaact tgtttattgc agcttataat ggttacaaat       8040
aaagcaatag catcacaaat ttcacaaata aagcattttt ttcactgcat tctagttgtg      8100
gtttgtccaa actcatcaat gtatcttatc atgtctggat cgatccgaac cccttcctcg      8160
accaattctc atgtttgaca gcttatcatc gcagatccgg gcaacgttgt tgcattgctg      8220
caggcgcaga actggtaggt atggaagatc tatacattga atcaatattg gcaattagcc      8280
atattagtca ttggttatat agcataaatc aatattggct attggccatt gcatacgttg      8340
tatctatatc ataatatgta catttatatt ggctcatgtc caatatgacc gccatgttga      8400
cattgattat tgactagtta ttaatagtaa tcaattacgg ggtcattagt tcatagccca      8460
tatatggagt tccgcgttac ataacttacg gtaaatggcc cgcctggctg accgcccaac      8520
gacccccgcc cattgacgtc aataatgacg tatgttccca tagtaacgcc aatagggact      8580
ttccattgac gtcaatgggt ggagtattta cggtaaactg cccacttggc agtacatcaa      8640
gtgtatcata tgccaagtcc gcccctatt gacgtcaatg acggtaaatg gcccgcctgg       8700
cattatgccc agtacatgac cttacgggac tttcctactt ggcagtacat ctacgtatta     8760
gtcatcgcta ttaccatggt gatgcggttt tggcagtaca ccaatgggcg tggatagcgg      8820
tttgactcac ggggatttcc aagtctccac cccattgacg tcaatgggag tttgttttgg      8880
caccaaaatc aacgggactt tccaaaatgt cgtaataacc ccgccccgtt gacgcaaatg      8940
ggcggtaggc gtgtacggtg ggaggtctat ataagcagag ctcgtttagt gaaccgtcag      9000
atctctagaa gctgggtacc ttaaggcgcc agctgatcaa gcttgctagc ggccgctcga      9060
ggccggcaag gccggatcca gacatgataa gatacattga tgagtttgga caaaccacaa      9120
ctagaatgca gtgaaaaaaa tgctttattt gtgaaatttg tgatgctatt gctttatttg      9180
taaccattat aagctgcaat aaacaagtta acaacaacaa ttgcattcat tttatgtttc      9240
aggttcaggg ggaggtgggg aggttttta aagcaagtaa aacctctaca aatgtggtat      9300
ggctgattat gatccggctg cctcgcgcgt ttcggtgatg acggtgaaaa cctctgacac      9360
atgcagctcc cggagacggt cacagcttgt ctgtaagcgg atgccgggag cagacaagcc      9420
cgtcagggcg cgtcagcggg tgttggcggg tgtcgggggcg cagccatgag gtcgactcta      9480
ga                                                                    9482

<210> SEQ ID NO 5
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 5
gatctgctag cgagcagctg tggaagcttg gt                                    32

<210> SEQ ID NO 6
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 6
```
ctagaccaag cttccacagc tgctcgctag ca            32

<210> SEQ ID NO 7
<211> LENGTH: 28
<212> TYPE: DNA
<213> ORGANISM: Artificial Sequence
<220> FEATURE:
<223> OTHER INFORMATION: LTBRFwd primer

<400> SEQUENCE: 7
ccgggatccg atgcgcctgc cccgggcc                 28

<210> SEQ ID NO 8
<211> LENGTH: 30
<212> TYPE: DNA
<213> ORGANISM: Artificial Sequence
<220> FEATURE:
<223> OTHER INFORMATION: LTBRRev primer

<400> SEQUENCE: 8
tcccgctagc attgctcctg gctctggggg               30

<210> SEQ ID NO 9
<211> LENGTH: 38
<212> TYPE: DNA
<213> ORGANISM: Artificial Sequence
<220> FEATURE:
<223> OTHER INFORMATION: PH086 primer

<400> SEQUENCE: 9
gatctgggta ccgggatcca aaactcgagc ccagctgt      38

<210> SEQ ID NO 10
<211> LENGTH: 38
<212> TYPE: DNA
<213> ORGANISM: Artificial Sequence
<220> FEATURE:
<223> OTHER INFORMATION: PH087 primer

<400> SEQUENCE: 10
acagctgggc tcgagttttg gatcccggta cccagatc      38

<210> SEQ ID NO 11
<211> LENGTH: 23
<212> TYPE: DNA
<213> ORGANISM: Artificial Sequence
<220> FEATURE:
<223> OTHER INFORMATION: PH088 primer

<400> SEQUENCE: 11
tcgaggtgct agcggaaagc ttg                      23

<210> SEQ ID NO 12
<211> LENGTH: 23
<212> TYPE: DNA
<213> ORGANISM: Artificial Sequence
<220> FEATURE:
<223> OTHER INFORMATION: PH089 primer

<400> SEQUENCE: 12
ggcccaagct ttccgctagc acc                      23

<210> SEQ ID NO 13
<211> LENGTH: 40
<212> TYPE: DNA
<213> ORGANISM: Artificial Sequence

```
<220> FEATURE:
<223> OTHER INFORMATION: LI17 primer

<400> SEQUENCE: 13
tcccccgggc catcgatggt accgaattca agcttcgtga                40

<210> SEQ ID NO 14
<211> LENGTH: 40
<212> TYPE: DNA
<213> ORGANISM: Artificial Sequence
<220> FEATURE:
<223> OTHER INFORMATION: LI18 primer

<400> SEQUENCE: 14
tcccccggga ccatcgatgg ccatggtggc cacgtgttca                40

<210> SEQ ID NO 15
<211> LENGTH: 40
<212> TYPE: DNA
<213> ORGANISM: Artificial Sequence
<220> FEATURE:
<223> OTHER INFORMATION: LI15 primer

<400> SEQUENCE: 15
tcccccgggc catcgataac tgtggaatgt gtgtcagtta                40

<210> SEQ ID NO 16
<211> LENGTH: 40
<212> TYPE: DNA
<213> ORGANISM: Artificial Sequence
<220> FEATURE:
<223> OTHER INFORMATION: LI16 primer

<400> SEQUENCE: 16
tcccccgggc catcgatagc tttttgcaaa agcctaggcc                40

<210> SEQ ID NO 17
<211> LENGTH: 32
<212> TYPE: DNA
<213> ORGANISM: Artificial Sequence
<220> FEATURE:
<223> OTHER INFORMATION: LI19 primer

<400> SEQUENCE: 17
agccccgggc ggctcaggga cccacggtgg aa                        32

<210> SEQ ID NO 18
<211> LENGTH: 32
<212> TYPE: DNA
<213> ORGANISM: Artificial Sequence
<220> FEATURE:
<223> OTHER INFORMATION: 19

<400> SEQUENCE: 18
ttccaccgtg ggtccctgag ccgcccgggg ct                        32

<210> SEQ ID NO 19
<211> LENGTH: 32
<212> TYPE: DNA
<213> ORGANISM: Artificial Sequence
<220> FEATURE:
<223> OTHER INFORMATION: LI21 primer

<400> SEQUENCE: 19
catcatccgg gtctccacgg ggtcagggtg at                        32
```

<210> SEQ ID NO 20
<211> LENGTH: 32
<212> TYPE: DNA
<213> ORGANISM: Artificial Sequence
<220> FEATURE:
<223> OTHER INFORMATION: LI22

<400> SEQUENCE: 20
atcaccctga ccccgtggag acccggatga tg                              32

<210> SEQ ID NO 21
<211> LENGTH: 25
<212> TYPE: DNA
<213> ORGANISM: Artificial Sequence
<220> FEATURE:
<223> OTHER INFORMATION: EoriFwd (7349-7320) primer

<400> SEQUENCE: 21
aaggaacagc gatatctccc acccc                                      25

<210> SEQ ID NO 22
<211> LENGTH: 33
<212> TYPE: DNA
<213> ORGANISM: Artificial Sequence
<220> FEATURE:
<223> OTHER INFORMATION: EoriRev (4948-4967) primer

<400> SEQUENCE: 22
acttcaattg cgaggttagg gacaacacgt tcc                             33

<210> SEQ ID NO 23
<211> LENGTH: 50
<212> TYPE: DNA
<213> ORGANISM: Artificial Sequence
<220> FEATURE:
<223> OTHER INFORMATION: PH094 primer

<400> SEQUENCE: 23
ctaggccatt tccaggtcct gtacctggcc cctcgtcaga catggtaaat            50

<210> SEQ ID NO 24
<211> LENGTH: 48
<212> TYPE: DNA
<213> ORGANISM: Artificial Sequence
<220> FEATURE:
<223> OTHER INFORMATION: PH095 primer

<400> SEQUENCE: 24
cgatttacca tgtctgacga ggggccaggt acaggacctg gaaatggc              48

<210> SEQ ID NO 25
<211> LENGTH: 27
<212> TYPE: DNA
<213> ORGANISM: Artificial Sequence
<220> FEATURE:
<223> OTHER INFORMATION: Primer M1

<400> SEQUENCE: 25
tggcgggggc ggttccatct gcagttg                                    27

<210> SEQ ID NO 26
<211> LENGTH: 29
<212> TYPE: DNA
<213> ORGANISM: Artificial Sequence
<220> FEATURE:
<223> OTHER INFORMATION: Primer M2

<400> SEQUENCE: 26
tttctttaaa cacgcctgga aggagaagc                              29

<210> SEQ ID NO 27
<211> LENGTH: 28
<212> TYPE: DNA
<213> ORGANISM: Artificial Sequence
<220> FEATURE:
<223> OTHER INFORMATION: Primer M3

<400> SEQUENCE: 27
ttcaatctct gcaccacggc gaccgctc                               28

<210> SEQ ID NO 28
<211> LENGTH: 30
<212> TYPE: DNA
<213> ORGANISM: Artificial Sequence
<220> FEATURE:
<223> OTHER INFORMATION: Primer M4

<400> SEQUENCE: 28
ttcaacatta acatcagatg aaccaaaata                             30

<210> SEQ ID NO 29
<211> LENGTH: 29
<212> TYPE: DNA
<213> ORGANISM: Artificial Sequence
<220> FEATURE:
<223> OTHER INFORMATION: Primer M5

<400> SEQUENCE: 29
gtccgccaag gggctatcct ccagggatc                              29

<210> SEQ ID NO 30
<211> LENGTH: 29
<212> TYPE: DNA
<213> ORGANISM: Artificial Sequence
<220> FEATURE:
<223> OTHER INFORMATION: Primer M6

<400> SEQUENCE: 30
tacataagcg gctgtgcgct gcttgaaag                              29

<210> SEQ ID NO 31
<211> LENGTH: 29
<212> TYPE: DNA
<213> ORGANISM: Artificial Sequence
<220> FEATURE:
<223> OTHER INFORMATION: Primer M7

<400> SEQUENCE: 31
caggcaccaa cagcggccca gggctcggg                              29

<210> SEQ ID NO 32
<211> LENGTH: 28
<212> TYPE: DNA
<213> ORGANISM: Artificial Sequence
<220> FEATURE:
<223> OTHER INFORMATION: Primer M8

<400> SEQUENCE: 32
tggtcggccg ccctgaactc ctgaaccc                               28

<210> SEQ ID NO 33

```
<211> LENGTH: 34
<212> TYPE: DNA
<213> ORGANISM: Artificial Sequence
<220> FEATURE:
<223> OTHER INFORMATION: Primer M9

<400> SEQUENCE: 33
aaaggatcca ccatgcccac atccccaccg acta                              34

<210> SEQ ID NO 34
<211> LENGTH: 32
<212> TYPE: DNA
<213> ORGANISM: Artificial Sequence
<220> FEATURE:
<223> OTHER INFORMATION: Primer M10

<400> SEQUENCE: 34
ttctcgagct ttatgtctga gacccttgtc cc                                32

<210> SEQ ID NO 35
<211> LENGTH: 37
<212> TYPE: DNA
<213> ORGANISM: Artificial Sequence
<220> FEATURE:
<223> OTHER INFORMATION: Primer LI53

<400> SEQUENCE: 35
ctagaggatc cgccaccatg gataaagttt taaacag                           37

<210> SEQ ID NO 36
<211> LENGTH: 35
<212> TYPE: DNA
<213> ORGANISM: Artificial Sequence
<220> FEATURE:
<223> OTHER INFORMATION: Primer LI54

<400> SEQUENCE: 36
cgactagact cgagttttat gtttcaggtt caggg                             35
```